US012760277B2

(12) United States Patent
Ben et al.

(10) Patent No.: US 12,760,277 B2
(45) Date of Patent: Oct. 13, 2026

(54) STABILIZED AMORPHOUS CALCIUM CARBONATE AS A SUPPLEMENT FOR CELL CULTURE MEDIA

(71) Applicant: Amorphical Ltd., Ness Ziona (IL)

(72) Inventors: Yosef Ben, Moshav Zofer (IL); Yigal Dov Blum, San Jose, CA (US); Sara Neuman, Ness Ziona (IL); Orit Ecker, Rishon Le-Zion (IL)

(73) Assignee: AMORPHICAL LTD., Ness Ziona (IL)

( * ) Notice: Subject to any disclaimer, the term of this patent is extended or adjusted under 35 U.S.C. 154(b) by 601 days.

(21) Appl. No.: 18/200,938

(22) Filed: May 23, 2023

(65) Prior Publication Data

US 2023/0365935 A1 Nov. 16, 2023

Related U.S. Application Data

(63) Continuation-in-part of application No. 16/069,774, filed as application No. PCT/IL2017/050058 on Jan. 17, 2017, now Pat. No. 12,060,573.

(60) Provisional application No. 63/433,491, filed on Dec. 19, 2022, provisional application No. 63/346,926, filed on May 30, 2022, provisional application No. 62/434,453, filed on Dec. 15, 2016, provisional application No. 62/376,428, filed on Aug. 18, 2016, provisional application No. 62/279,844, filed on Jan. 18, 2016, provisional application No. 62/279,845, filed on Jan. 18, 2016, provisional application No. 62/279,843, filed on Jan. 18, 2016.

(51) Int. Cl.
*C12N 5/077* (2010.01)
*A61P 21/00* (2006.01)

(52) U.S. Cl.
CPC ............ *C12N 5/0658* (2013.01); *A61P 21/00* (2018.01); *C12N 2500/14* (2013.01)

(58) Field of Classification Search
CPC .................................................... C12N 5/0018
See application file for complete search history.

(56) References Cited

U.S. PATENT DOCUMENTS

| | | | | |
|---|---|---|---|---|
| 4,757,017 | A | 7/1988 | Cheung | |
| 5,460,803 | A | 10/1995 | Tung | |
| 5,562,895 | A | 10/1996 | Tung | |
| 7,666,673 | B2 | 2/2010 | Shinohara | |
| 8,492,140 | B2 | 7/2013 | Smith | |
| 10,758,566 | B2 | 9/2020 | Ben | |
| 11,048,230 | B2 | 6/2021 | Flitsch | |
| 2015/0056306 | A1* | 2/2015 | Sagi | A61K 35/612 424/687 |

FOREIGN PATENT DOCUMENTS

| | | | |
|---|---|---|---|
| CN | 102604895 | A | 7/2012 |
| EP | 0628017 | A1 | 12/1994 |
| RU | 94022264 | A | 5/1996 |
| WO | 2005115414 | A2 | 12/2005 |
| WO | 2008041236 | A2 | 4/2008 |
| WO | 2009053967 | A1 | 4/2009 |
| WO | 2013088440 | A1 | 6/2013 |
| WO | 2014024191 | A1 | 2/2014 |
| WO | 2014122658 | A1 | 8/2014 |
| WO | 2016016893 | A1 | 2/2016 |
| WO | 2016016895 | A1 | 2/2016 |
| WO | 2016193982 | A1 | 12/2016 |
| WO | 2016193983 | A1 | 12/2016 |
| WO | 2017125917 | A1 | 7/2017 |
| WO | 2017125918 | A1 | 7/2017 |
| WO | 2021181372 | A1 | 9/2021 |

OTHER PUBLICATIONS

Ulbrich et al. The Impact of Simulated and Real Microgravity on Bone Cells and Mesenchymal Stem Cells. BioMed Research International 2014, Article ID 928507:1-15. (Year: 2014).*

Ackerman et al., (1985) Toxicity testing for human in vitro fertilization programs. J In Vitro Fert Embryo Transf 2(3): 132-137.

Agarwal and Sekhon (2010) The role of antioxidant therapy in the treatment of male infertility. Hum Fertil (Camb) 13(4): 217-225.

Ahdjoudj et al., (2002) Transforming growth factor beta2 inhibits adipocyte differentiation induced by skeletal unloading in rat bone marrow stroma. J Bone Miner Res 17(4): 668-677.

Amann and Waberski (2014) Computer-assisted sperm analysis (CASA): capabilities and potential developments. Theriogenology 81(1): 5-17.

Amselem (2019) Remote Controlled Autonomous Microgravity Lab Platforms for Drug Research in Space. Pharm Res 36(12): 183; pp. 1-15.

Ankrum et al., (2014) Mesenchymal stem cells: immune evasive, not immune privileged. Nat Biotechnol. Author manuscript; available in PMC Mar. 1, 2015. Published in final edited form as: Nat Biotechnol. Mar. 2014; 32(3): 252-260.

Bentov et al., (2010) Stabilization of amorphous calcium carbonate by phosphate rich organic matrix proteins and by single phosphoamino acids. J Struct Biol 171(2): 207-215.

Bhoumik et al., (2014) Optimum calcium concentration: a crucial factor in regulating sperm motility in vitro. Cell Biochem Biophys 70(2): 1177-1183.

Bisserier et al., (2021) Cell-Free Mitochondrial DNA as a Potential Biomarker for Astronauts' Health. J Am Heart Assoc 10(21): e022055. With correction.

Brusentsev et al., (2014) Traditional and Modern Approaches to Culture of Preimplantation Mammalian Embryos In Vitro. Russian Journal of Developmental Biology 45(2): 73-88; English abstract on p. 88.

(Continued)

*Primary Examiner* — Christopher M Babic
*Assistant Examiner* — Jennifer S Spence
(74) *Attorney, Agent, or Firm* — Ballard Spahr LLP

(57) ABSTRACT

Stabilized amorphous calcium carbonate (ACC) as a supplement of cell culture media and the cell culture medium supplements comprising stabilized ACC are provided. In particular the stabilized ACC is useful for enhancing the growth of cell and tissue cultures, gametes and embryos in vitro and particularly in microgravity.

19 Claims, 24 Drawing Sheets

(56) References Cited

OTHER PUBLICATIONS

Burnier et al., (1999) Pharmacokinetic and pharmacodynamic effects of YM087, a combined V1/V2 vasopressin receptor antagonist in normal subjects. Eur J Clin Pharmacol 55(9): 633-637. Abstract.
Bursac et al., (2015) Synergizing Engineering and Biology to Treat and Model Skeletal Muscle Injury and Disease. Annu Rev Biomed Eng 17: 217-242.
Caglar Aytac et al., (2015) Can calcium ionophore "use" in patients with diminished ovarian reserve increase fertilization and pregnancy rates? A randomized, controlled study. Fertil Steril 104(5): 1168-1174.
Culligan and Ohlendieck (2002) Abnormal Calcium Handling in Muscular Dystrophy. Basic Appl Myol 12(4): 147-157.
Datta et al., (2015) Add-ons in IVF programme—Hype or Hope? Facts Views Vis Obgyn 7(4): 241-250.
Decaux (2001) Long-term treatment of patients with inappropriate secretion of antidiuretic hormone by the vasopressin receptor antagonist conivaptan, urea, or furosemide. Am J Med 110(7): 582-584. Abstract.
Dubey et al., (2020) Correction of metabolic acidosis improves muscle mass and renal function in chronic kidney disease stages 3 and 4: a randomized controlled trial. Nephrol Dial Transplant 35(1): 121-129.
Durand-Smet et al., (2014) A comparative mechanical analysis of plant and animal cells reveals convergence across kingdoms. Biophys J 107(10): 2237-2244. With correction.
Eftekhar et al., (2013) Effect of oocyte activation with calcium ionophore on ICSI outcomes in teratospermia: A randomized clinical trial. Iran J Reprod Med 11(11): 875-882.
Fleetham et al., (1993) The mouse embryo culture system: improving the sensitivity for use as a quality control assay for human in vitro fertilization. Fertil Steril 59(1): 192-196.
Flinck et al., (2018) Roles of pH in control of cell proliferation. Acta Physiol (Oxf) 223(3): e13068; 17 pages.
Fried and Palevsky (1997) Hyponatremia and hypernatremia. Med Clin North Am 81(3): 585-609. Abstract.
Gheorghiade et al., (2007) Efficacy of Vasopressin Antagonism in Heart Failure Outcome Study With Tolvaptan (EVEREST) Investigators. Short-term clinical effects of tolvaptan, an oral vasopressin antagonist, in patients hospitalized for heart failure: the EVEREST Clinical Status Trials. JAMA 297(12): 1332-1343.
Glacken et al., (1986) Reduction of waste product excretion via nutrient control: Possible strategies for maximizing product and cell yields on serum in cultures of mammalian cells. Biotechnol Bioeng 28(9): 1376-1389.
Gridley et al., (2008) Long-term changes in rat hematopoietic and other physiological systems after high-energy iron ion irradiation. Int J Radiat Biol 84(7): 549-559.
Grimm et al., (2016) The impact of microgravity on bone in humans. Bone 87: 44-56. Abstract.
Hentemann et al., (2011) Differential pH in embryo culture. Fertil Steril 95(4): 1291-1294.
Hernández-Aguilera et al., (2013) Mitochondrial dysfunction: a basic mechanism in inflammation-related non-communicable diseases and therapeutic opportunities. Mediators Inflamm 2013: 135698, 13 pages.
Homa et al., (1993) The role of calcium in mammalian oocyte maturation and egg activation. Hum Reprod 8(8): 1274-1281.
Hughes-Fulford and Lewis (1996) Effects of microgravity on osteoblast growth activation. Exp Cell Res 224(1): 103-109.
Ivashkiv (2020) The hypoxia-lactate axis tempers inflammation. Nat Rev Immunol. Author manuscript; available in PMC Aug. 1, 2020. Published in final edited form as: Nat Rev Immunol. Feb. 2020; 20(2): 85-86.
Johnson et al., (1999) Maintenance of motility in mouse sperm permeabilized with streptolysin O. Biol Reprod 60(3): 683-690.
Joyce et al., (2012) Bone health and associated metabolic complications in neuromuscular diseases. Phys Med Rehabil Clin N Am 23(4): 773-799.
Juhl et al., (2021) Update on the effects of microgravity on the musculoskeletal system. NPJ Microgravity 7(1): 28.
Kasperk et al., (1995) Human bone cell phenotypes differ depending on their skeletal site of origin. J Clin Endocrinol Metab 80(8): 2511-2517. Abstract.
Kevenaar and Hoogenraad (2015) The axonal cytoskeleton: from organization to function. Front Mol Neurosci 8: 44; 12 pages.
Ko et al., (2020) Dose-dependent skeletal deficits due to varied reductions in mechanical loading in rats. NPJ Microgravity 6: 15.
Kostenuik et al., (1997) Skeletal unloading inhibits the in vitro proliferation and differentiation of rat osteoprogenitor cells. Am J Physiol 273(6 Pt 1): E1133-E1139.
Kostenuik et al., (1999) Skeletal unloading causes resistance of osteoprogenitor cells to parathyroid hormone and to insulin-like growth factor-I. J Bone Miner Res 14(1): 21-31.
Krieger et al., (2004) Mechanism of acid-induced bone resorption. Curr Opin Nephrol Hypertens 13(4): 423-436.
Kumar and Singh (2015) Trends of male factor infertility, an important cause of infertility: A review of literature. J Hum Reprod Sci 8(4): 191-196.
Lane et al., (2013) The role of nutritional research in the success of human space flight. Adv Nutr 4(5): 521-523.
Lang et al., (2017) Towards human exploration of space: the THESEUS review series on muscle and bone research priorities. NPJ Microgravity 3: 8.
Lee et al., (2020) Targeting myostatin/activin A protects against skeletal muscle and bone loss during spaceflight. Proc Natl Acad Sci U S A 117(38): 23942-23951.
Mahla (2016) Stem Cells Applications in Regenerative Medicine and Disease Therapeutics. Int J Cell Biol 2016: 6940283, 24 pages.
Marín-Briggiler et al., (2003) Calcium requirements for human sperm function in vitro. Fertil Steril 79(6): 1396-1403.
Meiron et al., (2011) Solubility and bioavailability of stabilized amorphous calcium carbonate. J Bone Miner Res 26(2): 364-372.
Michl et al., (2019) Evidence-based guidelines for controlling pH in mammalian live-cell culture systems. Commun Biol 2: 144; 12 pages.
Mitch (2006) Metabolic and clinical consequences of metabolic acidosis. J Nephrol 19 Suppl 9: S70- S75. Abstract.
Naciri et al., (2008) Monitoring pH and dissolved oxygen in mammalian cell culture using optical sensors. Cytotechnology 57(3): 245-250.
Nagaraja and Risin (2013) The current state of bone loss research: data from spaceflight and microgravity simulators. J Cell Biochem 114(5): 1001-1008.
Nasiri and Eftekhari-Yazdi (2015) An overview of the available methods for morphological scoring of pre-implantation embryos in in vitro fertilization. Cell J 16(4): 392-405.
Natan et al., (2023) Amorphous Calcium Carbonate Shows Anti-Cancer Properties That are Attributed to Its Buffering Capacity. Cancers (Basel) 15(15): 3785.
Orwoll et al., (2013) Skeletal health in long-duration astronauts: nature, assessment, and management recommendations from the NASA Bone Summit. J Bone Miner Res 28(6): 1243-1255.
Popper and Batra (1993) Calcium mobilization and cell proliferation activated by extracellular ATP in human ovarian tumour cells. Cell Calcium 14(3): 209-218.
Pradhan et al., (2012) In situ pH maintenance for mammalian cell cultures in shake flasks and tissue culture flasks. Biotechnol Prog 28(6): 1605-1610.
Qi et al., (2014) ATP-stabilized amorphous calcium carbonate nanospheres and their application in protein adsorption. Small 10(10): 2047-2056.
Rahman et al., (2014) Calcium influx and male fertility in the context of the sperm proteome: an update. Biomed Res Int 2014: 841615; 13 pages.
Rossi et al., (2019) Calcium, mitochondria and cell metabolism: A functional triangle in bioenergetics. Biochim Biophys Acta Mol Cell Res 1866(7): 1068-1078.
Sfontouris et al., (2015) Artificial oocyte activation to improve reproductive outcomes in women with previous fertilization failure: a systematic review and meta-analysis of RCTs. Hum Reprod 30(8): 1831-1841.

(56) References Cited

OTHER PUBLICATIONS

Shaltiel et al., (2013) Bone loss prevention in ovariectomized rats using stable amorphous calcium carbonate. Health 5 (7A2): 18-29.
Shechter et al., (2008) A gastrolith protein serving a dual role in the formation of an amorphous mineral containing extracellular matrix. Proc Natl Acad Sci U S A 105(20): 7129-7134.
Shin et al., (2013) Wasting mechanisms in muscular dystrophy. Int J Biochem Cell Biol 45(10): 2266-2279.
Sibonga et al., (2019) Resistive exercise in astronauts on prolonged spaceflights provides partial protection against spaceflight-induced bone loss. Bone 128: 112037.
Smith (2020) Microgravity, bone homeostasis, and insulin-like growth factor-1. Appl Sci 10(13): 4433.
Smith et al., (2012) Benefits for bone from resistance exercise and nutrition in long-duration spaceflight: Evidence from biochemistry and densitometry. J Bone Miner Res 27(9): 1896-1906.
Smith et al., (2015) Bone metabolism and renal stone risk during International Space Station missions. Bone 81: 712-720.
Smith SM, Zwart SR and Heer M (2014) Human Adaptation to Spaceflight: The Role of Nutrition. National Aeronautics and Space Administration (NASA). Lyndon B. Johnson Space Center, Houston, Texas, USA. NP 2014-10-018-JSC. 151 pages.
Smith SM, Zwart SR, Douglas GL and Heer M (2021) Human Adaptation to Spaceflight: The Role of Food and Nutrition. Second Edition. National Aeronautics and Space Administration (NASA). Lyndon B. Johnson Space Center, Houston, Texas, USA. NP-2021-03-003-JSC. 135 pages.
Stein and Blanc (2011) Does protein supplementation prevent muscle disuse atrophy and loss of strength? Crit Rev Food Sci Nutr 51(9): 828-834. Abstract.
Tarantino et al., (2020) Effects of Simulated Microgravity on Muscle Stem Cells Activity. Cell Physiol Biochem 54(4): 736-747.
Thor Christensen; Spaceflight caused DNA to leak out of astronauts' cell powerhouse. American Heart Association News, Oct. 20, 2021. MedicalXpress. Retrieved from: from https://medicalxpress.com/news/2021-10-spaceflight-dna-leakastronauts-cell.html on Aug. 15, 2023. 4 pages.
Tolba et al., (2016) High biocompatibility and improved osteogenic potential of amorphous calcium carbonate/vaterite. J Mater Chem B 4: 376-386.
Turner et al., (2013) Acute exposure to high dose $\gamma$-radiation results in transient activation of bone lining cells. Bone. Author manuscript; available in PMC Nov. 1, 2014. Published in final edited form as: Bone. Nov. 2013; 57(1): 164-173.
Vaisman et al., (2014) Increased calcium absorption from synthetic stable amorphous calcium carbonate: double-blind randomized crossover clinical trial in postmenopausal women. J Bone Miner Res 29(10): 2203-2209.
Van der Valk et al., (2010) Optimization of chemically defined cell culture media—replacing fetal bovine serum in mammalian in vitro methods. Toxicol In Vitro 24(4): 1053-1063.
Vogel et al., (2019) Expression of Hypoxia-Inducible Factor 1$\alpha$ (HIF-1$\alpha$) and Genes of Related Pathways in Altered Gravity. Int J Mol Sci 20(2): 436.
Wagner et al., (2007) Current treatment of adult Duchenne muscular dystrophy. Biochim Biophys Acta 1772(2): 229-237.
Willey et al., (2011) Ionizing Radiation and Bone Loss: Space Exploration and Clinical Therapy Applications. Clin Rev Bone Miner Metab. Author manuscript; available in PMC Jul. 21, 2012. Published in final edited form as: Clin Rev Bone Miner Metab. Mar. 2011; 9(1): 54-62.
Willey et al., (2011) Space Radiation and Bone Loss. Gravit Space Biol Bull. Author manuscript; available in PMC Jul. 21, 2012. Published in final edited form as: Gravit Space Biol Bull. 2011; 25(1): 14-21.
Williams et al., (2009) Acclimation during space flight: effects on human physiology. CMAJ 180(13): 1317-1323.
Willmann et al., (2012) Enhancing translation: guidelines for standard pre-clinical experiments in mdx mice. Neuromuscul Disord. Author manuscript; available in PMC Jan. 1, 2013. Published in final edited form as: Neuromuscul Disord. Jan. 2012; 22(1): 43-49.
Yuan et al., (2016) The Roles of Acidosis in Osteoclast Biology. Front Physiol 7: 222.
Zwart et al., (2006) Reduction of Dietary Acid Load as a Potential Countermeasure for Bone Loss Associated with Spaceflight. Preprint, Jan. 1, 2006. Retrieved from: https://ntrs.nasa.gov/citations/20060048264. 9 pages.
ACC in Space with NASA. Sep. 29, 2022. Retrieved from: https://web.archive.org/web/20220929200934/https://www.amorphical.com/density-in-space-with-nasa/ on Aug. 15, 2023. 1 page.
"Animal Reproduction Biotechnology", Sang Yun Zi editor. China Agriculture Press, Jul. 31, 2006. pp. 343-344. Machine translation.
Calcium in Cell Culture; Importance and uses of calcium in serum-free eucaryotic, including hybridoma and Chinese Hamster Ovary (CHO) cell cultures. Sigma-Aldrich. Retrieved from: https://web.archive.org/web/20150524020552/https:/www.sigmaaldrich.com/life-science/cell-culture/learning-center/media-expert/calcium.html May 24, 2015. 2 pages.
ClinicalTrials.gov Identifier: NCT01815021. A Study Comparing Amorphous Calcium Carbonate (ACC) Versus Crystalline Calcium (CCS) in Hypoparathyroidism Patients (AMCS009). First Posted: Mar. 20, 2013; Last Update Posted: Mar. 31, 2015. Retrieved from: https://classic.clinicaltrials.gov/ct2/show/NCT01815021 on Aug. 15, 2023. 8 pages.
DMD_M.2.1.005 (SOP (ID) Number): "The use of four limb hanging tests to monitor muscle strength and condition over time"; George Carlson (Author), Maaike van Putten (Official reviewer). Issued: Aug. 3, 2011 and Last reviewed: Jun. 29, 2016; 11 pages.
"Testing the Effect of Crustacean's Gastrolith Nutraceutical on Mineralization Rate During Distraction Osteogenesis"; Amorfical (Collaborator), Ron Lamdan, Hadassah Medical Organization (Responsible Party). Study NCT01087437, last updated Mar. 30, 2014 (v6). Retrieved from https://clinicaltrials.gov/ct2/history/NCT01087437?V_6=View#StudyPageTop on Jan. 24, 2019; 4 pages.
World Health Organization's Expanded Immunization Program and Communicable Diseases Department, 2000 Global Poliomyelitis Eradication Poliovirus Inspection Manual, published by the Ministry of Health of the People's Republic of China on Dec. 31, 1992, p. 62. Machine translation of p. 62.

* cited by examiner

Fig. 23B1 Fig. 23B2
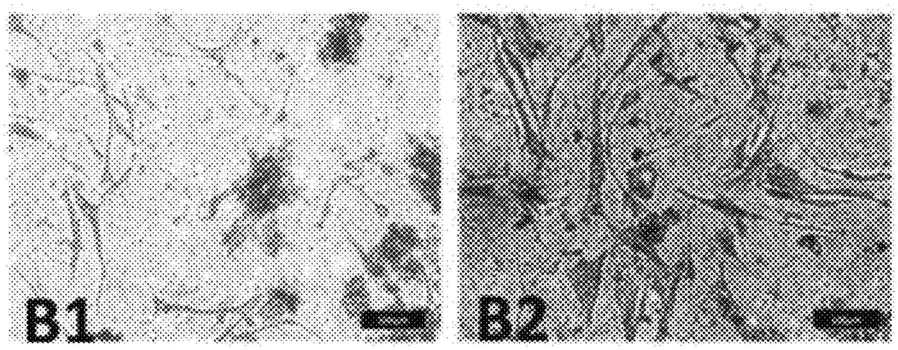
Fig. 23C
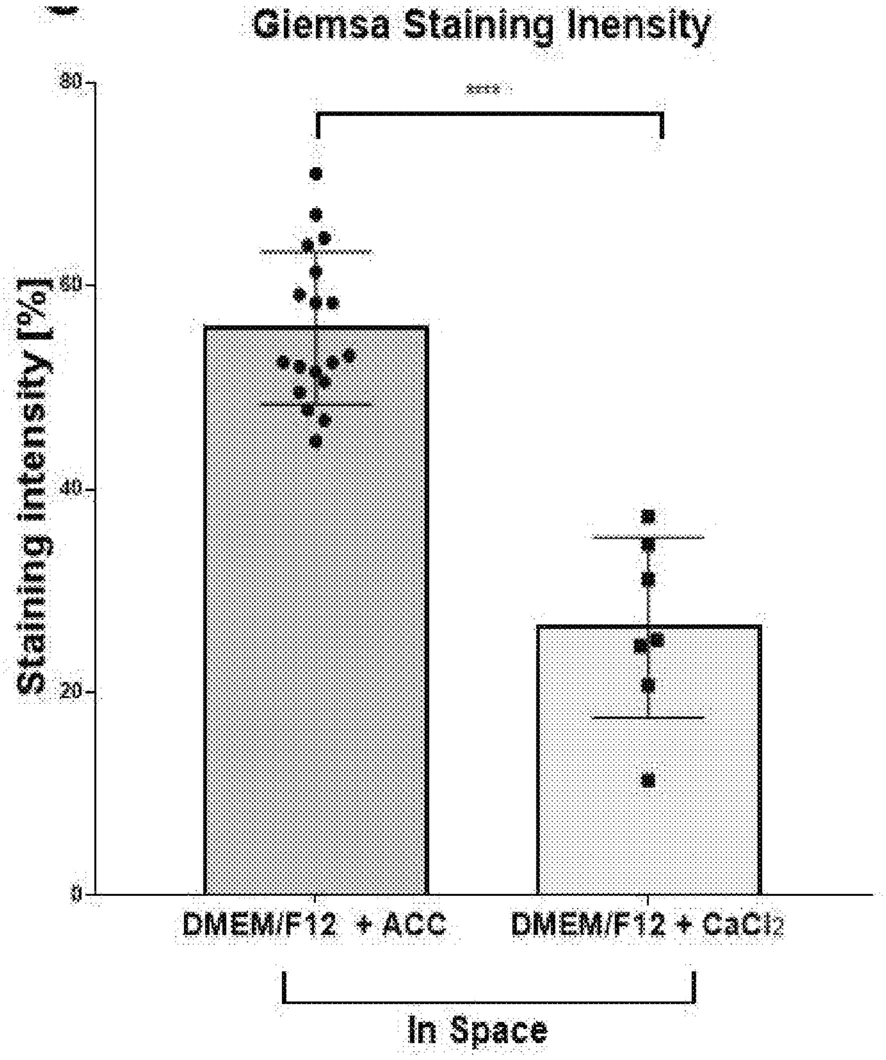

STABILIZED AMORPHOUS CALCIUM CARBONATE AS A SUPPLEMENT FOR CELL CULTURE MEDIA

FIELD OF THE INVENTION

The present invention provides stabilized amorphous calcium carbonate as a supplement of cell culture media. In particular the ACC is useful for enhancing the growth of cell and tissue cultures in vitro. In additional aspects of the invention, cell culture media supplement comprising stabilized ACC are provided.

BACKGROUND OF THE INVENTION

Cell culture techniques allow growing in vitro animal, plant or insect cells removed from tissues, when supplying the appropriate nutrients and conditions. Cell culture techniques have a number of applications including investigation of cellular processes, assessing the effect of various chemical compounds or drugs on specific cell types, synthesizing valuable biologics in the industrial scale and generation of expanded cells for transplantation purposes. Cell culture techniques are used for in vitro fertilization, stem cell research and vaccine production.

One of the most important uses of cell culture techniques is mass production of biologics including specific proteins such as monoclonal antibodies. The number of such commercially valuable biologics has increased rapidly over the last decades and has led to the present widespread interest in mammalian cell culture technology.

The composition of media used to culture cells is of a great importance because of its influence on cell survival, proliferation and production of the biologics of interest. Many different cell culture media, having different levels of specificity to cell cultures, were developed. While some of the media are basal media that may be supplemented according to the requirements of different cell cultures, other are more complex media. Hundreds of individual compounds can be added to cell culture media so as to obtain the desired effect. But the concept of media supplementation is usually limited to addition of materials that generally promote establishment and maintenance of a cell culture. Among most used supplements are minerals, vitamins, amino acids, hormones and serum, most often fetal bovine serum, horse serum or human serum. However, since the use of serum may be undesirable in many cases, growth media with reduced content of serum or serum-free media are used.

There is an ongoing research and development of media and in particular supplements to media allowing supporting and proliferation of cell and tissue cultures, particularly providing beneficial large-scale manufacturing culture conditions.

SUMMARY OF THE INVENTION

It has been surprisingly found that cell culture media supplemented with stabilized amorphous calcium carbonate (ACC) provide enhanced growth of various cells, in comparison to cells grown in media supplemented with other sources of calcium. In particular it has been observed that stabilized ACC enhanced myotubes formation in mdx cells, being a model of Duchenne muscular dystrophy. In addition, an enhanced in-vitro development of embryos was observed in the media comprising stabilized ACC, either a monoculture medium of "one step" or to the "sequential" (Cleavage medium). It has been surprisingly found that embryos, that were grown in cleavage medium supplemented with stabilized ACC showed a rapid cleavage and higher hatching rate. In other cases, neural cells grown in the media supplemented with ACC showed an enhance neural filaments regeneration, and stem cells grown in ACC supplemented media demonstrated faster expansion and differentiation. It was further surprisingly found, that sperm, incubated in the presence of ACC, demonstrated much higher motility following swim-up procedure, and the concentration of sperm cell incubated with ACC in the upper phase (the motile sperm) was up to 7 times higher than the concentration in the untreated sample. Moreover, it has been shown that ACC did not have the bi-phasic effect on sperm motility which has been observed upon addition of $Ca^{2+}$ ions to sperm samples. All these observations indicate that stabilized ACC being a supplement to a cell culture media enhance and promotes cells growth and provides better functionality.

In one aspect the present invention provides a cell culture medium, wherein the cell culture medium is supplemented with amorphous calcium carbonate (ACC) stabilized by at least one stabilizing agent and wherein said cell culture medium is suitable for growth of a biological culture. According to some embodiments, the medium is suitable for growing culture of cells, tissue culture, organ culture or organs. According to other embodiments, the cell culture medium supplemented with stabilized ACC is capable of enhancing or promoting the growth, e.g., enhancing the proliferation, maturation, propagation, regeneration, development, preservation such as cryopreservation and/or differentiation of cells, tissues and organs. According to one embodiment, the cells are animal, plant or insect cells. According to one embodiment, the cell culture medium supplemented with stabilized ACC is suitable for growth and optionally capable of enhancing the growth of cell culture, tissue culture, organ culture, wherein said cultures are animal, plant or insect cell, tissue, or organ culture. According to one embodiment, the cell culture medium supplemented with stabilized ACC is suitable for growth of stem cell such as embryonic, chorionic, amniotic, hematopoietic, mesenchymal, neural, glial, Nasal Olfactory Mucosa (NOM), adult tissue specific and induced pluripotent stem cells or for growth of embryos, such as human or non-human mammal embryos. In other embodiments, such cell culture medium is capable of enhancing stem cells proliferation, expansion and/or differentiation, capable of enhancing gametes maturation or capable of enhancing development of embryos. According to some embodiments, the cell culture medium supplemented with stabilized ACC is suitable for growth and optionally capable of enhancing the growth of yeast or bacteria. In some embodiments, the bacteria is *E. coli* or probiotic bacteria such bacteria of *Bifidobacterium* and *Lactobacillus* genera. According to any one of the above embodiments, the cell culture medium of the present invention may be any medium suitable for growth of cells, e.g. natural medium comprising biological fluid or artificial medium such as balanced salt solution, basal medium or complex medium. The cell culture medium of the present invention may be further supplemented as known in art. According to the present invention, the cell culture medium is supplemented with ACC stabilized by at least one stabilizing agent. The stabilizing agent may be any agent known in art. In particular embodiments, the stabilizer is selected from a polyphosphate, such as inorganic polyphosphate, phosphorylated amino acid, bisphosphonate, organic acid and any combination thereof. According to some embodiments, the stabilizing agent is a combination of said stabilizers, e.g. combination of inorganic polyphosphate with organic acid such as citric acid or a combination of a phosphorylated amino acid with an organic acid.

According to another aspect the present invention provides amorphous calcium carbonate (ACC) stabilized by at least one stabilizing agent, for use as a supplement to a cell culture medium. According to one embodiment, the stabilized ACC is added to the medium during the preparation of the medium. According to another embodiment, the ACC is added to the medium before use.

According to yet another aspect, the present invention provides a cell culture medium supplement comprising amorphous calcium carbonate (ACC) stabilized by at least one stabilizing agent. According to one embodiment, the cell culture medium supplement comprising the stabilized ACC is added to the medium during the preparation of the medium. According to another embodiment, the supplement is added to the medium prior use. The cell culture medium supplement may be a solid, liquid or semi-liquid supplement. According to any one of the above embodiments, the ACC is stabilized by at least one stabilizing agent. Such cell culture medium supplement is capable of enhancing growth e.g. enhancing the proliferation, maturation, propagation, regeneration, development and/or differentiation of cells, tissues and organs.

According to a further aspect, the present invention provides amorphous calcium carbonate (ACC) stabilized by at least one stabilizer and formulated as a supplement for cell culture medium, wherein said ACC is stabilized by at least one stabilizing agent.

According to another aspect, the present invention provides a method for enhancing cell growth of a biological culture, comprising exposing the biological culture to ACC stabilized by at least one stabilizer. According to some embodiments, the biological culture is selected from a culture of cells, cell culture, tissue culture, organ culture and bacterial culture. In one embodiment, the method comprises enhancing cell growth and in particular enhancing formation of myotubes, enhancing embryo development, enhancing nerve cells regeneration and enhancing maturation and/or preservation of gametes.

According to one aspect, the present invention provides a kit comprising ACC for use as a supplement for cell culture medium of the present invention, or a cell culture medium supplement comprising stabilized ACC, and instructions for use of said ACC or said supplement in combination with cell culture medium. According to certain aspects, the present invention provides a kit comprising amorphous calcium carbonate (ACC) stabilized by at least one stabilizer and instructions for use of said ACC in combination with cell culture medium. According to one embodiment, the ACC is for use as a cell culture medium supplement. According to some embodiments, the kit comprises cell culture medium supplement comprising ACC stabilized by at least one stabilizer and instruction for use of said ACC in combination with cell culture medium. The kit of the present invention may further comprise any know medium suitable for growth of cells, tissues, or organs.

According one aspect, the present invention provides a method for enhancing and/or supporting growth of a biological culture in microgravity conditions, comprising growing the biological culture in a cell culture medium comprising an amorphous calcium carbonate (ACC) stabilized by at least one stabilizer, wherein the growth of the biological culture is performed in microgravity conditions. According to some examples, method composes enhancing growth of the biological culture, wherein enhancing growth of the biological culture is selected from the group consisting of enhancing proliferation, enhancing maturation, enhancing propagation, enhancing regeneration, enhancing differentiation, enhancing development, enhancing the biological culture survival in space microgravity, enhancing the biological culture survival in radiation environment, and a combination thereof. In some examples, the biological culture is selected from a culture of eukaryote or prokaryote cells. In some examples, the culture of eukaryote cells is selected from a culture of animal, plant, and insect cells. In some examples, at least one of the following exists: (i) the culture of animal cells is selected from a cell culture, tissue culture, organ culture, stem cells, gametes, embryos, and an organ of human or non-human mammal; (ii) the mammal cell culture is selected from a nerve, muscle, epithelial, bone, adipose, stem cell, and blood cell culture; and (iii) the mammal tissue culture is selected from epithelial, connective, muscular and nervous tissue culture; and the organ culture is selected from an ovary. In some examples, the cell culture is a primary cell culture or a cell line selected from a finite and continuous cell line. In some examples, at least one of the following exists (i) the cell culture is a primary cell culture or a cell line selected from a finite and continuous cell line, optionally wherein said cell line is selected from bone-marrow derived MSC, MBA-13, MDX, FM3, HeLa, 293, A-549, ALC, CHO, HB54, HL60, COS-7, HEK293, VERO, BHK, CV1, MDCK, 3T3, C127 MRC-5, BAE-1, SH-SY5Y, L-929, HEP G2, NSO, U937, NAMALWA, WEHI 231, YAC 1, and U 266B1 cell line; and (ii) the epithelial tissue culture is selected from skin, stomach and intestinal lining, kidney and glands tissue culture, the muscular tissue culture is selected from smooth, skeletal and cardiac muscle tissue culture, the nervous tissue culture is selected from brain, spinal cord and nerves tissue. In some examples, the stem cells are selected from embryonic, chorionic, amniotic, hematopoietic, mesenchymal, neural, NOM, glial, adult and induced pluripotent stem cells. In any one of the above examples, the stabilizing agent is selected from the group consisting of a polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides, and derivatives thereof, proteins, phosphorylated proteins, natural and synthetic biopolymers and derivatives thereof, and any combinations thereof. In some examples, the stabilizing agent is selected from the group consisting of phosphoserine, triphosphate, adenosine triphosphate, adenosine diphosphate, phytic acid, citric acid, etidronic acid, pyrophosphate, ethanol, hexametaphosphate, chitin, and any combination thereof. In some examples, the method comprises enhancing at least one of (i) nerve cells regeneration; (ii) muscle cells formation and growth; (iii) stem cells differentiation; (iv) oocytes or sperm cells maturation; (v) embryos development; (vi) embryo or gamete cryopreservation; (vii) myotubes formation; (viii) onset for muscle cell contraction; (ix) cell culture survival in space microgravity; (x) cell culture survival in radiation environment; (xi) osteocytes formation; and (xii) cell fusion and conversion into fiber cells.

According to another aspect, the present invention provides a method of preventing the loss in the mass of a musculoskeletal system in space microgravity, in a subject in need thereof, comprising administering to said subject an amorphous calcium carbonate stabilized by at least one stabilizing agent. According to some embodiments, the method comprises preventing the loss of the mass of a bone and/or muscle.

According to one aspect, the present invention provide a method of treating damages caused by exposure to microgravity conditions in a subject in need thereof, comprising administering to said subject an amorphous calcium carbonate stabilized by at least one stabilizing agent. According to some examples, the exposure comprises a long exposure. According to certain embodiments, the damage comprises loss of the mass of a bone and/or muscle.

BRIEF DESCRIPTION OF THE FIGURES

FIG. 1A-FIG. 1E show the effect of different calcium sources on neuronal sprouting from cultured spinal cord-dorsal root ganglia (SC-DRG) slices. Immunofluorescent staining (anti neurofilament antibody) of nerve fibers grown from SC-DRG slices exposed to the following calcium compounds ($Ca^{2+}$ concentration of 2 mM): (FIG. 1A) ACC-Etidronic Acid; (FIG. 1B) ACC-phosphoserine; (FIG. 1C) gastrolith; (FIG. 1D) crystalline calcium carbonate (CCC); and (FIG. 1E) $CaCl_2$) solution (control). Original magnification ×100.

FIG. 2A and FIG. 2B show the effect of (FIG. 2A) ACC-stabilized by Etidronic Acid and (FIG. 2B) $CaCl_2$) solution (control) on neuronal sprouting from brain cells cultured on chitosan microcarriers (MCs). Immunofluorescent staining of nerve fibers (anti neurofilament antibody) grown from brain cells-chitosan MCs aggregates, after 30 days in culture in the presence of 2 mM of either ACC-Etidronic Acid or $CaCl_2$ is presented.

FIG. 9A-FIG. 9C show Alizarin red staining of osteoblasts following 10 days in culture as a function of various medium treatments. The media was supplemented with additional 1 mM $Ca^{2+}$ from: FIG. 9A—ACC, FIG. 9B—$CaCl_2$, or FIG. 9C—control, no $Ca^{2+}$ addition.

FIG. 10A-FIG. 10C show Alkaline phosphatase staining of osteoblasts following 10 days in culture as a function of various medium treatments. The media c was supplemented with additional 1 mM $Ca^{2+}$ from: FIG. 10A—ACC, FIG. 10B—$CaCl_2$, or FIG. 10C—control, no $Ca^{2+}$ addition.

FIG. 11A and FIG. 11D—ACC, FIG. 11B and FIG. 11E—$CaCl_2$, or FIG. 11C and FIG. 11F—control (without additional supplement with calcium).

FIG. 13E and FIG. 13F present the quantitative analyses, performed by the ImageJ software Pixel Counter application.

FIG. 17A-FIG. 17C show the phase-contrast microscope images illustrating the effect of ACC on human bone marrow-derived mesenchymal stem cells (BM-MSC) in space, stained with Alizarin Red. BM-MSC growing in differentiation medium with: (FIG. 17A) ACC and (FIG. 17B) without ACC (with $CaCl_2$)). FIG. 17C shows a statistical analysis of staining intensity, determined by ImageJ software Pixel Counter.

(FIG. 18A) BM-MSCs growing with ACC and (FIG. 18B) without ACC. FIG. 18C shows the staining intensity that was analyzed by ImageJ software Pixel Counter application, as indicated in the Materials and Methods. Significant differences were obtained between the control group ($CaCl_2$)) (7 images) and the ACC-treated group (8 images).

(FIG. 19A) Apr. 7, 2022; (FIG. 19B) Apr. 11, 2022; (FIG. 19C) Apr. 15, 2022. Slot 7: BM-MSC with ACC: (FIG. 19D) Apr. 5, 2022; (FIG. 19E) Apr. 11, 2022; (FIG. 19F) Apr. 15, 2022. On the first day, the concentration of the cells was similar in both groups. In space, the number of cells decreased. The reduction in the group without ACC (FIG. 19B and FIG. 19C) is higher than that of the ACC group (FIG. 19E and FIG. 19F), demonstrating that cells with ACC survived better in space in comparison to the control group. BM-MSCs survived better than the muscle cells.

FIG. 21B shows the fluorescence intensity that was determined using the ImageJ software Pixel Counter application. All relative changes were calculated from the $CaCl_2$) fluorescent intensity on day 2 (FC=1). Higher fluorescence intensity was obtained in the ACC group.

FIG. 23A1-FIG. 23C show the phase-contrast microscope images illustrating the effect of ACC on humanmuscle cells in space with Giemsa staining. FIG. 23A1 and FIG. 23A2 represent muscle cells growing in differentiation (fusion) medium with ACC; FIG. 23B1 and FIG. 23B2 capture muscle cells growing in differentiation (fusion) medium with $CaCl_2$). FIG. 23C illustrates the significant difference ($P<0.0001$) between the intensity of the staining in the cultures with and without the ACC.

FIG. 24A represents muscle cells growing in differentiation (fusion) medium with ACC; FIG. 24B captures muscle cells growing in differentiation (fusion) medium with $CaCl_2$). FIG. 24C illustrates the significant difference ($P<0.0001$) between the intensity of the staining in the cultures with and without the ACC.

(FIG. 25A) 4th; (FIG. 25B) 13th; and (FIG. 25C) 15th. Slot 3 shows muscle cells cultured with ACC: (FIG. 25D) 4th; (FIG. 25E) 13th; and (FIG. 25F) 15th. On the first day, the concentration of the cells in both groups was similar. In space, the number of cells decreased.

DETAILED DESCRIPTION OF THE INVENTION

Figure 1:
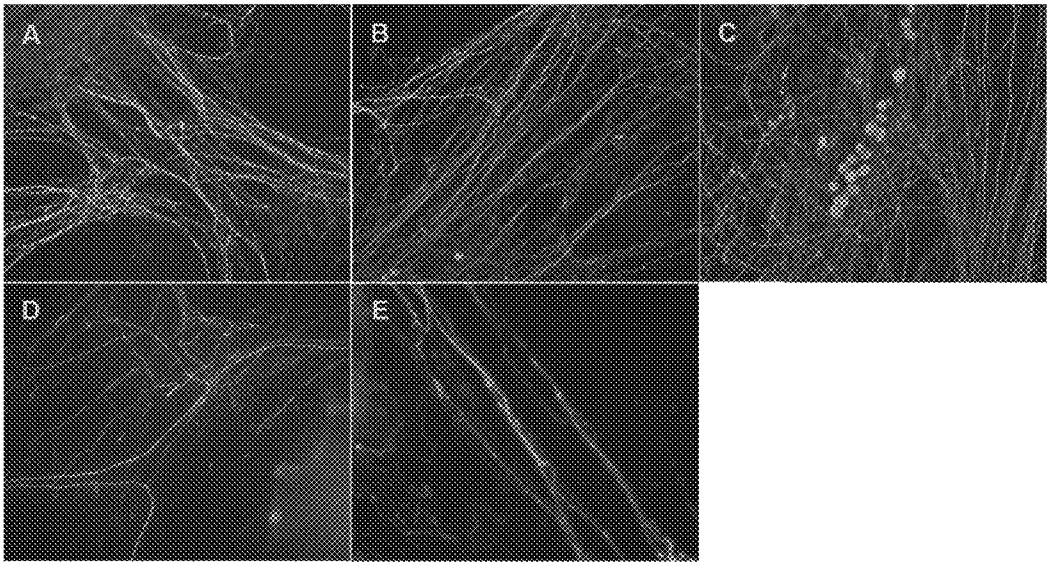

It has been surprisingly found that addition of ACC to cell culture medium enhances growth of various types of cells. Further, it was surprisingly found that cells grown in space microgravity conditions in cell culture media supplemented with ACC showed a better proliferation, differentiation, and survival rate than in control media comprising an alternative source of calcium. This was specifically shown for the differentiation of primary skeletal muscle cells into muscle fibers; and similarly, bone marrow-derived MSC that differentiated into mature osteoblasts and osteocytes, compared to media containing the typical highly soluble calcium chloride. Moreover, the survival rate of osteocytes was comparable to that seen on earth. This is especially unexpected considering that typically muscle cells suffer from increased mortality in microgravity conditions. According to one aspect, the present invention provides a cell culture medium supplemented with amorphous calcium carbonate (ACC), wherein said ACC is stabilized by at least one stabilizing agent. According to other aspects, the present invention provides stabilized ACC for use as a supplement to a cell culture medium. In certain aspects, the present invention provides a cell culture supplement comprising stabilized ACC. In other aspects, the present invention provides stabilized ACC for use as a supplement to a cell culture medium in microgravity conditions, i.e., in space. In certain examples, the cell culture is muscle cell culture. In some examples, the cell culture is a bone cell culture. According to other aspects, the stabilized ACC supplemented to a biological culture enhances the growth, fusion, proliferation, and differentiation of muscle and/or bone cell culture in microgravity.

For each aspect of the present invention individually and collectively the following terminology is used and the specific parameters are as defined hereinbelow:

The term "cell culture medium", "growth medium" and "culture medium" are used herein interchangeably and refer to a medium used for, suitable for or capable of supporting the growth of a biological culture such as cells, tissues or organs and providing said cells, tissue or organ with a proper environment. Different cell culture media may have different properties and comprise different components, however almost all media are isotonic media and have an osmotic pressure suitable for cell growth. Thus, the cell culture medium is an isotonic cell culture medium. The term "isotonic" as used herein refers a cell culture medium having the osmolality of an aqueous solution at 37° C. is in the range of 270-300 mOsmol/kg. Thus, in one embodiment, water or more particular de-ionized water per se is not considered as a cell culture medium. According to some embodiments, the tissue culture comprises sodium chloride, potassium chloride and a source of phosphorous such as sodium phosphate mono or di basic. According to some embodiments, the medium is suitable for growing cell culture, tissue culture, organ culture or organs. The cells may be eukaryotic or prokaryotic. In particular the cell culture medium refers to a medium suitable for growth eukaryotic culture of cell, tissue culture or organ culture. In some particular embodiments, the medium may be a complete medium, a basal medium, a basal medium supplemented with cell culture medium supplement, medium with various amounts of serum or chemically defined medium.

The term "supplemented" as used herein refers to a medium to which the ACC stabilized with at least one stabilizer is added, thus the medium comprises ACC stabilized with at least one stabilizer. The term encompasses the medium prepared with ACC and medium to which the ACC is added before use.

Thus in one embodiment, the present invention provides a cell culture medium, wherein the cell culture medium is supplemented with amorphous calcium carbonate (ACC) stabilized by at least one stabilizing agent and wherein said cell culture medium is suitable for growth of a biological culture.

The terms "culture", "biological culture" and "culture of cells" are used herein interchangeably and refer to cells, tissues, organs culture or organ grown in vitro in a pre-defined condition. In some embodiments, the biological culture is selected from a animal, plant or insect cell culture; animal, plant or insect tissue culture, animal, plant or insect organ culture, yeast culture and bacterial culture.

The term "cell culture" as used herein refers to cells of a multicellular eukaryote which are maintained, cultivated or grown in an artificial in vitro environment. The cell culture may be a suspension culture, in which the cells are cultured in a liquid medium by constant agitation or on micro carriers, or an adherent or monolayer culture.

The term "tissues culture" as used herein refers to a tissue maintained or grown in vitro.

The term "organ culture" as used herein refers to part(s) of an organ or a whole organ cultured in vitro.

The term "stem cells" refers to cells which have the capacity to proliferate and differentiate into different cell types.

The term "amorphous calcium carbonate" and "ACC" are used herein interchangeably and refer to non-crystalline form of calcium carbonate stabilized by at least one stabilizing agent. ACC may be obtained from a natural source or chemically synthesized. The terms also include naturally stabilized ACC such as ACC obtained from gastrolith.

The term "natural ACC" as used herein refers to any ACC isolated or derived from a natural source. Non-limiting examples of natural sources of ACC include gastroliths of freshwater crustaceans.

The term "synthetic ACC" as used herein refers to any ACC produced and/or derived by man ex-vivo.

According to some embodiments, the cell culture medium according to the present invention is suitable for growth of a biological culture. According to one embodiment, the biological culture is a culture of eukaryote or prokaryote cells. The term "growth" as used herein encompass any of the following: proliferation, maturation, propagation, regeneration, support, differentiation, development, preservation, cryopreservation and any combination thereof and may be used differently in accordance to the type of cells. According to one embodiment, the cell culture medium is suitable for supporting, for proliferation or propagation of cells. In one exemplary embodiment, the cell culture medium is suitable for proliferation or propagation of eukaryotic cells, e.g. unicellular organisms or cells of a multicellular organism. According to another exemplary embodiment, the cell culture medium is suitable for proliferation or propagation of prokaryotic cells. According to other embodiments, the cell culture medium is suitable for maturation and/or development of cells, e.g. development of embryos or maturation of gamete cells. The term "embryo" as used herein refers to a fertilized mammalian oocyte, i.e. a zygote, and to a multicellular organism developing from said zygote at its earliest stages of the development. The terms "gamete" or "gamete cells" are used herein interchangeably and refers to any male or female germ cell that is capable of initiating formation of a new diploid individual. Examples of gametes are sperm and oocytes. The term "sperm" and "spermatozoa" as used herein interchangeably refers to male reproductive cells. The term "sperm sample" refers to one or more samples comprising sperm. The sperm sample may be semen obtained from a subject or processed semen, liquefied semen, sedimented and optionally resuspended sperm, etc. According to some embodiments, the cell culture medium is suitable for regeneration of cells, e.g. regeneration of nerve cells. The terms "neuronal regeneration" and "nerve regeneration" as used herein may be used interchangeably and refer to recovery of functions of a damaged nerve. Specifically, it includes recovery of signaling via the nerve by repairing a damaged site, regrowth of axonal and dendritic neuronal fibers, of the peripheral or the central nervous system. In some embodiments, nerve regeneration refers to sprouting from damaged neuronal fibers. In some embodiments, nerve regeneration refers to sprouting from damaged neuronal fibers. Therefore, the cell culture medium according to the present invention is capable of promoting profound nerve fiber regeneration. According to another embodiment, the cell culture medium is suitable for differentiation of cells, e.g. differentiation of stem cells and in particular differentiation of stem cells to osteoblasts. According to some embodiments, the cell culture medium is suitable for supporting a proliferation of a tissue culture and organ culture. According to some embodiments, the cell culture medium is suitable for in vitro preservation of an organ.

According to some embodiments, the cell culture medium supplemented with stabilized ACC according to the present invention is capable of enhancing the growth as defined herein above of a biological culture. The term "enhancing" as used herein refers to promoting, improving, augmenting, ameliorating, typically increasing the growth parameters. According to some embodiments, of the present invention, the terms "capable of enhancing" and "enhances" are used interchangeably. The enhancement may be measured relatively to a control sample grown in identical conditions but without the ACC. Thus in one embodiment, the cell culture medium supplemented with stabilized ACC according to the present invention is capable of enhancing proliferation, maturation, propagation, regeneration, development, cryopreservation and/or differentiation of cells, tissues or organs. According to one embodiment, the cell culture medium is capable of enhancing differentiation of stem cells. According to another embodiment, the cell culture medium supplemented with stabilized ACC is capable of enhancing proliferation of cells. According to yet another embodiment, the cell culture medium supplemented with stabilized ACC is capable of enhancing maturation of cells. According to a further embodiment, the cell culture medium supplemented with stabilized ACC is capable of enhancing development of cells or tissues. According to certain embodiments, the cell culture medium supplemented with stabilized ACC is capable of enhancing regeneration of cell. The enhancement of proliferation, maturation, propagation, regeneration, development and/or differentiation of cells, tissues or organs may be measured as percent of enhancement in comparison to the control as defined hereinabove. Therefore, according to one embodiment, the cell culture medium supplemented with stabilized ACC is capable of enhancing the growth parameters by about 10% to about 600%, about 20% to about 500%, about 30% to about 400%, about 40% to about 300%, about 50% to about 200, about 60% to about 150% or about 70% to about 100%. Enhancement by 100% meaning that the parameter, e.g., proliferation is increased 2 times; enhancement by 200% means that the parameter, e.g. embryo development, is increased 3 times, and so on. According to some embodiments, the growth parameters are enhanced by about 100% to about 500%, about 120% to about 400%, about 150% to about 300%.

According to some embodiments, the cell culture medium supplemented with stabilized ACC is suitable for growth and optionally enhancing growth of a culture of eukaryote cells, e.g. eukaryote cell, tissue or organ culture. According to some embodiments, cell culture medium supplemented with stabilized ACC is for growth of eukaryote cells. According to some embodiments, the culture of eukaryote cells is selected from a culture of animal, plant, and insect cells.

According to one embodiment, the culture of eukaryote cell, tissue or organ culture is animal cell, tissue or organ culture, stem cells, embryos and an organ. According to some embodiments, the animal is human or non-human mammal. Thus, according to one embodiment, the cell culture medium supplemented with stabilized ACC is suitable for growth and optionally enhancing growth of mammal cell, tissue or organ culture, mammal stem cells, mammal embryos or a mammal organ.

According to one embodiment, the mammal is human, thus according to one embodiment, the cell culture medium according to the present invention is suitable for growth of a culture of human cell, tissue or organ culture, stem cells, embryos or an organ.

According to other embodiments, the mammal is a non-human mammal. According to one embodiment, the non-human mammal is livestock animals such as cattle, pigs, sheep, goats, horses, mules, asses, buffalo, or camels. In another embodiment, the non-human mammal is a domestic pet e.g. a cat or dog; a rodent such as a mouse, rat, guinea pig or hamster; a lagomorpha such as a rabbit; or a primate such as a monkey (e.g. macaques) or an ape (e.g. chimpanzee).

According to some embodiments, the cell culture medium according to the present invention is suitable for growth of a mammal cell culture. According to some embodiments, the mammal cell culture, either human or non-human mammal cell culture is selected from a cell culture of nerve, muscle, epithelial, bone, adipose, stem cells, gametes, and blood cell. According to one embodiment, the cell culture is a muscle cell culture. According to another embodiment, the cell culture is a nerve cell culture. According to further embodiment, the cell culture is a bone or osteocyte cell culture. According to one embodiment, the cell culture is bone marrow cell culture. According to another embodiment, the cell culture is tumor or cancer cells. According to some embodiments, the cell culture medium supplemented with ACC according to the present invention is capable of enhancing the growth of said cell culture. According to some embodiments, the cell culture is suspension or adherent cell culture. According to any one of the above embodiments, the growth is performed in microgravity conditions. According to some embodiments, the growth is performed in space.

According to some embodiments, the cell culture is a primary culture. The term "primary culture" as used herein refers to cells which were isolated from the tissue and proliferated under the appropriate conditions.

According to another embodiment, the cell culture is a cell line. The term "secondary culture" and "cell line" are used herein interchangeably and refer to a sub-cultured primary culture, i.e. primary culture transferred from one culture vessel to another culture vessel. According to some embodiments, the cell line is a finite cell lines, i.e. the cell lines which have a limited life span and go through a limited number of cell generations. According to another embodiments, the cell line is a continuous cell line, i.e. immortal cell line acquired the ability to divide indefinitely.

According to one particular embodiment, the cell line is selected from FM3, HeLa, 293, A-549, ALC, CHO, HB54, HL60, COS-7, HEK293, VERO, BHK,CV1, MDCK, 3T3, C127 MRC-5, BAE-1, SH-SY5Y, L-929, HEP G2, NSO, U937, NAMALWA, WEHI 231, YAC 1, and U 266B1 cell line. According to some embodiments, the cell culture medium supplemented with stabilized ACC is capable of enhancing growth of said cell line.

According to some embodiments, the cell culture medium of the present invention is suitable for growth of a mammal tissue culture. According to one embodiment, the mammal tissue culture is a human tissue culture. According to another embodiment, the tissue culture is a non-human mammal tissue culture. According to one embodiment, the tissue culture is selected from epithelial, connective, muscular and nervous tissue culture. According to one embodiment, the tissue culture is a nervous tissue culture. According to another embodiment, the tissue culture is a muscular tissue culture. According to yet another embodiment, the tissue culture is an epithelial tissue culture, such as nasal olfactory mucosa. According to a further embodiment, the tissue culture is a bone tissue culture.

According to some more particular embodiment, the tissue culture is selected from kidney, hepatic, glandular, brain, bone, ocular and muscle tissue culture. According to one embodiment, the epithelial tissue culture is selected from skin, stomach and intestinal lining, kidney and glands tissue culture, the muscular tissue culture is selected from smooth, skeletal and cardiac muscle tissue culture the, the nervous tissue culture is selected from brain, spinal cord and nerves tissue.

According to some embodiments, the cell culture medium supplemented with stabilized ACC is capable of enhancing growth of said tissue culture. In one embodiment, such medium is capable of enhancing regeneration of nervous tissue culture. In some embodiments, the medium is capable of enhancing regeneration of nervous culture by about 10% to about 200%, about 20% to about 150%, about 30% to about 120% or about 40% to about 100%. In other embodiments, such medium is capable of enhancing myotube formation and/or enhancing or promoting the onset of contractility of muscle cells such as also reducing the time to the onset of spontaneous contractile activity of myotubes. In one embodiment, the medium is capable of enhancing myotube formation by about 10% to about 600%, about 20% to about 500%, about 30% to about 400%, about 40% to about 300%, about 50 to about 200, about 60% to about 150% or about 70% to about 100%. The term "myotube formation" as used herein refers to a process in which myoblasts fuse into multi-nucleated fibers, myotube. According to any one of the above embodiments, the growth is performed in microgravity conditions. According to some embodiments, the growth is performed in space.

According to some embodiments, the cell culture medium of the present invention is suitable for growth of stem cells. According to some embodiments, the stem cells are human stem cells. According to another embodiment, the stem cells are non-human mammal stem cells. According to some embodiments, the stem cells are selected from embryonic, chorionic, amniotic, hematopoietic, mesenchymal, neural, glial, adult and induced pluripotent stem cells. According to one embodiment, the stem cells are embryonic stem cells. According to another embodiment, the stem cells are hematopoietic stem cells. According to a further embodiment, the stem cells are mesenchymal stem cells. According to yet another embodiment, the stem cells are pluripotent stem cells. According to some embodiments, the stem cells are adult stem cells, e.g. mesenchymal stem cells, epidermal stem cells, epithelial stem cells, hematopoietic stem cells or neural stem cells According to one embodiment, the cell culture medium of the present invention is suitable for proliferation, expansion and/or differentiation of stem cells. According to another embodiment, the cell culture medium of the present invention is capable of enhancing proliferation and/or differentiation of stem cells. According to one particular embodiment, the cell culture medium of the present invention is capable of enhancing differentiation of stem cells to osteoblast, i.e. enhancing osteoblastic differentiation. According to any one of the above embodiments, the growth is performed in microgravity conditions. According to some embodiments, the growth is performed in space.

According to some embodiments, the cell culture medium of the present invention is suitable for growth of embryos. According to one embodiment, the cell culture medium of the present invention is suitable for development of the embryos. According to another embodiment, the cell culture medium of the present invention is capable of enhancing the development of embryos. According to one embodiment, the medium is capable of enhancing embryo development by about 10% to about 300%, about 20% to about 250%, about 30% to about 200%, about 40% to about 150%, about 60% to about 100% or about 70% to about 90%. The terms "embryogenesis" and "embryo development" are used herein interchangeably and refer to the process by which the embryo forms and develops from the stage of a zygote to become an embryo, as known in the art, and includes the stages of reaching the stage of cleavage, compaction, blastocyst formation or blastocyst hatching. The terms "cleavage", "compaction", blastocyst" and "hatching" as used herein refer to the terms routinely used in embryology. The term "cleavage" is the division of cells in the early embryo. Producing a cluster of cells the same size as the original zygote. The different cells derived from cleavage are called blastomeres. The term "compaction" as used herein refers to the stage in which the dividing cells originated from a zygote maximize their contact with each other by polarization and adhesion, forming a compact ball that is held together by tight junctions. The term "blastocyst" as used herein, refers to a structure which is developed after the compaction stage and comprising an inner cell mass, which subsequently forms the embryo, and the outer layer of the blastocyst, which surrounds the inner cell mass and a fluid-filled cavity called blastocoele. The term "hatching" as used herein refers to a stage at which the embryo emerges through its outer shell (zona pellucida). According to any one of the above embodiments, the growth is performed in microgravity conditions. According to some embodiments, the growth is performed in space.

The term "enhancing embryo development" as used herein refers to promoting, enhancing or improving the rate and/or the efficacy of development process as well as to the proportion of the successfully grown and developed embryos. The enhancement is measured relatively to a control sample undergoing the same procedure but without the ACC in the growth media. According to one embodiment, the embryos are human embryos. According to another embodiment, the embryos are non-human mammal embryos. In some embodiments, the non-human mammal is selected from cattle, pigs, sheep, goats, horses, mules, donkey, buffalo, or camels. In some other embodiments, the non-human mammal is selected from a cat, dog, mouse, rat, guinea pig, hamster, rabbit, monkey or ape.

According to some embodiments, the cell culture medium is capable of improving or prolonging cryopreservation of embryos or gametes, as describe hereinabove. As used herein, the term "cryopreservation" refers to the storage of cells, such as gametes of embryos, at ultra-low temperatures, usually in liquid nitrogen (−196° C.).

According to some embodiments, the cell culture medium of the present invention is suitable for growth of gamete cells. According to one embodiment, the cell culture medium supplemented with stabilized ACC is suitable for maturation and/or preservation of gamete cells. According to one embodiment, gamete cells are oocytes. According to another embodiments, gamete cells are sperm cells. According to any one of the above embodiments, the gamete cells are gamete cells of a human or non-human mammal. According to some embodiments the non-human mammal is selected from the group consisting of livestock animals, domestic pets, rodents, wild animals and primate. In one embodiment, the livestock animals is selected from cattle, pigs, sheep, goats, horses, mules, asses, buffalo, and camels. In some other embodiments, the domestic pet is a cat or dog, the rodent is rat, mice, guinea pig or hamster, the lagomorpha is a rabbit, and the primate is monkey such as macaques or ape embryo such as chimpanzee. According to any one of the above embodiments, the growth is performed in microgravity conditions. According to some embodiments, the growth is performed in space.

According to another embodiment, the gamete cells are a gamete cells of a non-mammal animal. According to some embodiments, the non-mammal animal is selected from the group consisting fish, insects and birds.

According to one embodiment, the gamete cells are human sperm cells or oocytes.

According to some embodiments, cell culture medium supplemented with stabilized ACC is capable of enhancing the maturation of oocytes or sperm. According to one embodiment, the cell culture medium supplemented with stabilized ACC is capable of ameliorating the quality of sperm. The terms "enhancing maturation of sperm" and "ameliorating the quality of sperm" are used herein interchangeably and refer to improving the quality of sperm, e.g. enhancing sperm motility, enhancing sperm progressive motility, increasing sperm count, and any combination thereof. Thus in one embodiment, the cell culture medium supplemented with stabilized ACC is capable of enhancing sperm motility, enhancing sperm progressive motility, increasing sperm count, and any combination thereof. The term "sperm motility" as used herein refers to the fraction of sperm moving among all the sperms in a given specimen sample. The term "progressive motility" as used herein refers to the fraction of sperm moving in an approximately constant direction. The terms "enhancing sperm motility" and "enhancing sperm progressive motility" as used herein, refer to increasing the fraction of motile sperm and of sperm having progressive motility, respectively. Therefore, in one embodiment, the present invention provides a method for enhancing sperm motility. According to another embodiment, the present invention provides a method for enhancing sperm progressive motility. The sperm motility, progressive motility and sperm maturation stage may be assessed by any known method in the art. For example the motility may be assessed by computer-assisted sperm analysis (CASA) method (Amann & Waberski, 2014, Theriogenology, 81: 5-17). The term "sperm sample" refers to one or more samples comprising sperm. The sperm sample may be semen obtained from a subject or processed semen, liquefied semen, sedimented and optionally resuspended sperm, etc. According to some embodiments, increasing sperm count comprises increasing the sperm count in motility or progressive motility procedure. According to one embodiments, the motility or progressive motility procedure is a swim up procedure. According to any one of the above embodiments, the growth is performed in microgravity conditions. According to some embodiments, the growth is performed in space.

According to some embodiments, the cell culture medium of the present invention is suitable for growth of organ tissue or organ. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary. Thus the cell culture medium of the present invention is capable of enhancing preservation or maintaining organ tissue or organ. According to any one of the above embodiments, the growth is performed in microgravity conditions. According to some embodiments, the growth is performed in space.

According to some embodiments, the cell culture medium of the present invention is suitable for growth of plant cells. According to some embodiments, the cell culture medium of the present invention is suitable for growth of plant cell culture. According to another embodiment, the cell culture medium of the present invention is suitable for growth plant tissue culture. The term "plant cell culture" refers to plant cells derived from tissue or cells of plants, which are then cultured in a container or recipient. The term "plant tissue culture" include callus tissues (callus), differentiated cultured tissues or a cultured organ tissue. The term "callus" refers to a mass of unorganized parenchymatic cells derived from plant tissue (explants).

According to another embodiment, the cell culture medium of the present invention is suitable for growth of insect cells. According to one embodiment, the insect cells are insect cell culture e.g. insect cell lines. The cell types are as describe hereinabove. In one particular embodiment, the cell lines are selected from Sf 9, Sf 21 and high-five cell lines. According to another embodiment, the cell culture medium of the present invention is suitable for growth insect tissue culture. According to further embodiment, the insect cells are insect organ culture.

According to some embodiments, the cell culture is suspension or adherent cell culture.

In one embodiment, the cell culture medium supplemented with stabilized ACC is capable of enhancing growth of plant cell or tissue culture, or capable of enhancing growth of insect cell, tissue or organ culture.

According to any one of the above embodiments, the cell culture medium of the present invention, suitable to growth of animal, plant or insect cells, tissue or organ cultures may be a natural medium or an artificial medium, supplemented with ACC stabilized by at least one stabilizing agent, as defined in the present invention. According to some embodiments, the medium is a natural medium supplemented with ACC stabilized by at least one stabilizing agent. According to some embodiments, the natural medium comprises biological fluid selected from plasma, serum, lymph, human placental cord serum, and amniotic fluid. According to another embodiment, the natural medium comprises tissue extracts such as extract of liver, spleen, tumors, leucocytes and bone marrow, extract of bovine embryo and chick embryos. According to a further embodiment, the natural medium comprises coagulants or plasma clots. According to some embodiments, the medium is an artificial medium supplemented with ACC stabilized by at least one stabilizing agent. According to one embodiment, the artificial medium is a balanced salt solution. Examples of balanced salt solution are PBS, DPBS, HBSS, EBSS Tyrode's T6, WM1, Pool's P1, Quinn's HTF, and Gardner's G1. According to another embodiment, the artificial medium is a basal medium. According to some embodiments, the medium may be further supplemented as well known in the art. According to one embodiment, the medium is supplemented with serum, e.g. fetal bovine serum. According to a further embodiment, the artificial medium is a complex medium.

The term "basal medium" as used herein refers to a nutrient mixture of inorganic salts, sugars, amino acids, optionally also containing vitamins, organic acids and/or buffers. Basal media together with supplements provide the nutrients necessary to support cell life, growth and reproduction. The choice of basal medium used should be appropriate for the culture.

According to one embodiment, the artificial medium is a serum free medium. According to a further embodiment, the artificial medium is a medium with reduced serum content. According to another embodiment, the artificial medium is a protein-free media.

Examples of the cell media that may be supplemented with ACC stabilized by at least one stabilizer and used according to the present invention are Dulbecco's Modified Eagle's Medium (DMEM), Minimum Essential Medium (EMEM), RPMI 1640 medium (developed at Roswell Park Memorial Institute), and Basal Medium Eagle (BME). Further examples of media according to the present invention are Ham's Nutrient Mixtures such as Ham's F-10, Ham's F-12, DMEM/F-12 (DMEM and Ham's F-12). Other examples are Iscove's Modified Dulbecco's Medium (IMDM), opti-MEM® and Glasgow's MEM (GMEM). Examples of media suitable for insect cells growth are IPL-41 Insect Medium, Schneider's *Drosophila* medium, Grace's Insect medium, Serum-free Insect Media, Sf-900™, TC-10, Shields and Sang M3 Insect Medium, TC-100 Insect Medium, TNM-FH Insect Medium and IPL-10. Examples of media suitable for embryos growth are monoculture media such as SAGE 1-Step™ or sequential Media such as Quinns Advantage™ Sequential Media (ORIGIO). Examples of media suitable for plant cell growth are Murashige and Skoog (MS), B5, N6 and Nitsch's medium.

Other examples of media are Modified Medium, NCTC Medium, MegaCell™ Media, Claycomb, Click's Medium, L-15 Medium, Medium 199, MCDB Media, Ames' Media, BGJb Medium (Fitton-Jackson Modification), Click's Medium, CMRL-1066 Medium, McCoy's 5A Modified Medium, NCTC Medium, Swim's S-77 Medium, Waymouth Medium, William's Medium E and in vitro fertilization media such as Global®, GM501, SSM™, Cleavage K-SICM, Blastocyst K-SIBM, Quinns Advantage® Cleavage, Quinns Advantage® Blastocyst, FERTICULT™IVF Medium, FERTICULT™ G3 Medium, IVC-TWO™, IVC-THREE™, ECM®, MultiBlast®, EmbryoAssist™, BlastAssist™, ISM1, ISM2, G-1TMPLUS, G-2TMPLUS, IVF™, and CCM™. Further examples of media are media for sperm separation such as ISolate®, PureCeption™, Multipurpose Handling Medium® (MHM®), media for sperm wash such as Quinns™ Sperm Washing Medium, Multipurpose Handling Medium® (MHM®) or Modified HTF Medium with Gentamicin, medium for sperm capacitation such as Biggers-Whitten-Whittingham (BWW) medium, Ham's-F10 and a modified Tyrode's medium (HSM), and media for maturation which enables the culture of immature oocytes to fully developed embryos suitable for transfer. In other embodiments, the medium is a medium for oocytes maturation such as SAGE™ In-Vitro Maturation Media (IVM) and BO-IVM Oocyte maturation medium, medium for fertilization, medium for embryo development, Media for gamete Handling, medium for Preimplantation genetic diagnosis (PGD) or a medium for embryo or/and gamete maturation, handling and/or cryopreservation. Thus according to one embodiment, the cell culture medium is selected from HI medium, DMEM, RPMI 1640, MEM, IMDM, L-15 Medium (Leibovitz), MCDB Medium, Medium 199, opti-MEM® and DMEM/F-12, Schneider's

*Drosophila* medium, Grace's Insect medium, IPL-41 Insect Medium Sf-900™, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell™ Media, McCoy's 5A Modified Medium, NCTC Medium, Williams' Medium E, Waymouth Medium, TC-10 and IPL-10 medium. According to another embodiment, the cell culture medium is selected from HI medium, DMEM, RPMI 1640, MEM, IMDM, opti-MEM®, GMEM, Ham's F-12 and DMEM/F-12, Schneider's *Drosophila* medium, Grace's Insect medium, Sf-900™, TC-10, IPL-10 medium, media for sperm separation, wash or maturation such as ISolate®, PureCeption™, Multipurpose Handling Medium® (MHM®), Quinns™ Sperm Washing Medium, Multipurpose Handling Medium® (MHM®), Biggers-Whitten-Whittingham (BWW) medium, Ham's-F10 and a modified Tyrode's medium (HSM), and modified HTF medium with Gentamicin, medium for fertilization, medium for embryo development, and medium for embryo or/and gamete maturation, handling and/or cryopreservation.

According to some embodiments, the cell culture medium supplemented by stabilized ACC of the present invention is suitable for growth of unicellular eukaryotes. According to one embodiments, the unicellular eukaryotes are yeasts such as *Saccharomyces*, more particular *Saccharomyces cerevisiae*. According to one embodiment, the cell culture medium of the present invention suitable for growth of unicellular eukaryotes, e.g. *Saccharomyces cerevisiae*, is selected from yeast extract peptone dextrose (YPD), Yeast extract-peptone-glycerol (YPG) and Yeast extract-peptone-dextrose (YPAD) media. In one embodiment, the cell culture medium supplemented with stabilized ACC is capable of enhancing the growth of yeast.

According to some embodiments, the cell culture medium of the present invention is suitable for growth of prokaryotes. In particular embodiment, the cell culture medium of the present invention is suitable for growth of microorganisms. In some embodiments the microorganisms are microbiome microorganisms. In some embodiments the microorganisms are bacteria. Thus, in particular embodiment, the cell culture medium of the present invention is suitable for growth of bacteria. In some embodiments, the bacteria is *E. coli* or probiotic bacteria such bacteria of *Bifidobacterium* and *Lactobacillus* genera. Additional examples of probiotic bacteria species strains are *Lactobacillus Paracasei, Bifidobacterium Longum, Lactobacillus Johnsonii, Lactobacillus Fermentum, Pediococcus* Acidlacti such as: *Lactobacillus Acidophilus, Lactobacillus Rhamnosus* GG, *Lactobacillus Helveticus, Bifidobacterium Infantis, Bifidobacterium Lactis, Lactobacillus Bulgaricus, Lactobacillus Silivarius, Lactobacillus Plantarum, Lactobacillus Reuteri, Lactobacillus Casei, Bifidobacterum Bifidum, Saccharomyces Boulardii, Streptococcus Thermophilus, Bifidobacterum Breve, Bacillus Coagulans*, and *Lactobacillus Brevis*. According to some embodiments, the medium suitable for growth of bacteria is selected from LB and M9. In one embodiment, the cell culture medium supplemented with stabilized ACC is capable of enhancing the growth of bacteria.

According to some embodiments, the cell culture medium of the present invention is suitable for growth of archaea. In one embodiment, the cell culture medium supplemented with stabilized ACC is capable of enhancing the growth of archaea.

According to any one of aspects and embodiments of the present invention, ACC is stabilized by at least one stabilizing agent. The terms "stabilizing agent" and "stabilizer" are used herein interchangeably and refer to any substance that contributes to preserving calcium carbonate in the amorphous state during ACC production, formulating storage and/or use. In certain embodiments, the stabilizing agent is a single agent. In other embodiments, use of several stabilizing agents is encompassed. The terms "stabilized ACC" and "ACC stabilized by at least one stabilizer" may be used in some embodiments, interchangeably.

The stabilizer may comprise a molecule having one or more functional groups selected from, but not limited to, hydroxyl, carboxyl, ester, amine, phosphino, phosphono, phosphate, sulfonyl, sulfate, or sulfino groups. The hydroxy bearing compounds, combined with the hydroxide, optionally also bear other functions like carboxyl, etc. but with the hydroxyl not being esterified.

According to some embodiments, the stabilizer has low toxicity or no toxicity to mammalian cells or organism, and in particular to a human being. According to some embodiments, the stabilizer is of food, nutraceutical or pharmaceutical grade.

In certain embodiments, the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate; an organophosphate compound; an organophosphonate compound; organic polyphosphate, an inorganic polyphosphate, an inorganic phosphorous acid, an organic compound having multiple functional groups as defined above; an inorganic phosphate and polyphosphate compound; an organic compound having a polyphosphate chain; an organic surfactant; a bio-essential inorganic ion; saccharides and derivatives thereof, proteins, phosphorylated proteins, natural and synthetic biopolymers and derivatives thereof or any combination thereof. According to some embodiments, the stabilizer may have also a pharmaceutical activity, e.g. bisphosphonate, or ATP.

Thus in one embodiment, the stabilizing agent is selected from the group consisting of polyphosphate such as inorganic polyphosphate, organic acids, phosphorylated, phosphonated, sulfated or sulfonated organic compounds, phosphoric or sulfuric esters of hydroxy carboxylic acids, phosphorylated amino acids, bisphosphonate, organic polyphosphate, saccharides and derivatives thereof, proteins, peptides, phosphorylated proteins, phosphorylated peptides, and any combinations thereof. According to another embodiment, the stabilizing agent is selected from the group consisting of phosphoserine, adenosine triphosphate, adenosine diphosphate, phytic acid, citric acid, etidronic acid, pyrophosphate, polyphosphate, triphosphate, ethanol, hexametaphosphate, chitin, and any combination thereof.

According to some embodiments, the stabilizer is an organic acid. According to certain embodiments, the organic acid is selected from ascorbic, citric, lactic or acetic acid, oxalic acid, malonic acid, glutaconic acid, succinic acid, maleic acid, lactic acid, glutamic acid, aconitic acid, and optionally include compounds having at least two carboxylic groups optionally having molecular weight not larger than 250 g/mol, such as citric acid, tartaric acid, malic acid, etc. According to one particular embodiment, the stabilizer is citric acid.

In another embodiment, the phosphoric ester of hydroxyl carboxylic acids is a phosphoenolpyruvate. In another embodiment, the phosphoric or sulfuric esters of hydroxyl carboxylic acids comprise amino acids. Examples of such esters are phosphoserine, phosphothreonine, sulfoserine, sulfothreonine and phosphocreatine.

In another embodiment, the stabilizer is a saccharide. According to one embodiment, the saccharides is selected from mono-, di- tri-, oligo-, and polysaccharides like sucrose mannose, glucose, chitosan and chitin. Stabilizer may be in some embodiments polyols like glycerol. According to another embodiment, the stabilizer is an amino acid such as serine or threonine. Each possibility represents a separate embodiment, of the present invention.

Non-limiting examples of natural and synthetic biopolymers and derivatives are polynucleotides and glycoproteins.

Some specific unlimited examples for such ACC stabilizers that were approved for food consumption, found in natural food or in human beings include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and saccharides, selected from mono-, di-, tri-, oligo- and poly-saccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments, of the invention, the stabilizer is an organic acid selected from monocarboxylic acid or multiple carboxylic acid, e.g. dicarboxylic acid or tricarboxylic acid. Each possibility represents a separate embodiment, of the invention. The organic acid may be as defined above.

In some embodiments, of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N; P or S in the phase of oxides; or N as ammonia or nitro groups.

The stabilizer may further include phosphonate compounds such as, but not limited to bisphosphonates, polyphosphates, such as, but not limited to pyrophosphate or polyphosphonates or organo polyphosphates, such as, but not limited to, adenosine diphosphate (ADP) or adenosine triphosphate (ATP).

Optionally ACC is stabilized by a combination of phosphoserine and citric acid. In another embodiment, the ACC is stabilized by triphosphate and citric acid.

The ACC may be stabilized by more than one stabilizer, e.g. two stabilizers. The stable ACC can comprise more than two stabilizers, wherein one or more stabilizers are added to the ACC during the formation and precipitation of the ACC; hence constituting “internal” stabilizers, and another one or more stabilizers are added at the ACC particle surfaces after their formation; hence, constituting “external” stabilizers. Further examples for stable ACC and the preparation thereof may be found in International Patent Applications Nos. WO 2009/053967, WO 2014/024191 and WO 2016/193982.

In some embodiments, the stabilizing agent is a protein. In one embodiment, the protein is a naturally produced and purified protein. In another embodiment, the protein is synthetically produced protein. In some embodiments, the protein is selected from GAP65, GAP22, GAP21 and GAP12 proteins. In another embodiment, the proteins are selected from CqCDA1, chitinase 2, beta-N-acetylglucosaminidase, GAMP-like, chitin-binding protein, CqCBP, CAP10, GAP 18.2, GAP 02526, CqHc1, CqHc2, CqHc3, CqHc4, CqHc5, CqHc6, CqHc7, cryptocyaninl, cyclophilin, cystatin 1, cycstatin 2, LPS-BP, LEA protein and crystacyanin, optionally said proteins are originated from *C. quadricarinatus*. According to certain embodiments, the proteins are phosphorylated proteins.

In some embodiments, the stabilizing agent is selected from a polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides, derivatives thereof, proteins, phosphorylated proteins, natural and synthetic biopolymers and derivatives thereof and any combinations thereof. In other embodiments, the stabilizing agent is selected from phosphoserine, triphosphate, adenosine triphosphate, adenosine diphosphate, phytic acid, citric acid, etidronic acid, pyrophosphate, ethanol, hexametaphosphate, chitin, and any combination thereof.

In some embodiments, the stabilizing agent is selected from organic acids, phosphorylated organic acids, phosphoric or sulfuric esters of hydroxy carboxylic acids, phosphorylated amino acids, bisphosphonate, organic polyphosphate, saccharides, derivatives thereof, proteins and any combinations thereof.

According to some embodiments, the at least one stabilizer is selected from the group consisting of a polyphosphate, bisphosphonate, phosphorylated amino acid, citric acid, and any combination thereof. In some embodiments, more than one stabilizer, e.g. 2, 3 or 4 stabilizers are added.

According to some embodiments, the stabilizer is a polyphosphate or pharmaceutically acceptable salts thereof. According to some embodiments, the polyphosphate is physiologically compatible, water soluble polyphosphate salt selected from the group consisting of sodium, potassium and any other essential cation of polyphosphate. In one embodiment, the polyphosphate is organic or inorganic polyphosphate. The term “polyphosphate” as used herein refers to polymeric esters of $PO_4$. According to some embodiments, the polyphosphate is physiologically compatible water-soluble polyphosphate salt selected from the group consisting of sodium and potassium polyphosphate. In some embodiments, the polyphosphate is an inorganic polyphosphate or pharmaceutically acceptable salts thereof. Not-limiting examples of such salt are Na, K, Mg, Mn and Zn. According to some embodiments, the inorganic phosphate comprises 2 to 10 phosphate groups, e.g. 2, 3, 4, 5, 6, 7, 8, 9, or 10 phosphate group. According to some embodiments, the polyphosphate is selected from pyrophosphate, triphosphate, and hexametaphosphate. According to one embodiment, the stabilizer is pyrophosphate or pharmaceutically acceptable salts thereof such as sodium pyrophosphate. According to another embodiment, the stabilizer is triphosphate or pharmaceutically acceptable salts thereof such as sodium triphosphate. The term "triphosphate" and "tripolyphosphate" are used herein interchangeably. According to a further embodiment, the stabilizer is hexametaphosphate or a pharmaceutically acceptable salt thereof such as sodium hexametaphosphate.

According to some embodiments, the stabilizer is a bisphosphonate or pharmaceutically acceptable salts thereof. The not-limiting examples of salt are Na, K, Mg, Mn and Zn.

The term "bisphosphonate" as used herein refers to organic compounds having two phosphonate ($PO(OH)_2$) groups. The term further relates to compounds having a backbone of PO3-organic-PO3. Most typical is a series of bisphosphonates that are used as pharmaceuticals for treating osteoporosis. According to some embodiments, the bisphosphonate is selected from the group consisting of etidronic acid, zoledronic acid, medronic acid, alendronic acid and a pharmaceutically acceptable salt thereof. According to some embodiments, the stabilizer is an etidronic acid or a pharmaceutically acceptable salt thereof. According to another embodiment, the stabilizer is a zoledronic acid or a pharmaceutically acceptable salt thereof. According to a further embodiment, the stabilizer is a medronic acid or a pharmaceutically acceptable salt thereof. According to certain embodiments, the stabilizer is alendronic acid or a pharmaceutically acceptable salt thereof.

According to certain embodiments, the stabilizer is a phosphorylated amino acid. According to one embodiment, the phosphorylated amino acid is phosphoserine. According to another embodiment, the phosphorylated amino acid is phosphothreonine.

According to some embodiments, the ACC composition comprises a combination of the stabilizers disclosed above.

According to some embodiments, the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiments, the P:Ca molar ratio is about 1:25 to about 1:4. In further embodiment, the P:Ca molar ratio is about 1:20 to about 1:5. In another embodiment, the P:Ca molar ratio is about 1:20 to about 1:6. In a particular embodiment, the P:Ca molar ratio is about 1:15 to about 1:5. In another particular embodiment, the P:Ca molar ratio is about 1:25 to about 1:5. According to some embodiments, such polyphosphate is pyrophosphate, triphosphate, hexametaphosphate or a pharmaceutically acceptable salt thereof. According to another embodiments, the bisphosphonate is alendronic acid, etidronic acid, zoledronic acid or medronic acid and the P:Ca molar ratio is as defined hereinabove.

According to some embodiments, the calcium content (Ca content) stabilized ACC comprising polyphosphate or bisphosphonate is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 wt % to about 38 wt %. The terms "Ca content" and "calcium content" is used herein interchangeably and refer to the content of calcium of the ACC in the final composition.

In certain embodiments, the P:Ca molar ratio is about 1:40 to about 1:1, and the Ca content is about 20 wt % to about 39 wt %. In some embodiments, the molar ratio is 1:28 to about 1:3, and the Ca content is about 30 wt % to about 38 wt %. In another embodiment, the molar ratio is 1:25 to about 1:5, and the Ca content is about 30 wt % to about 36 wt %.

According to some embodiments, the stabilizer is selected from the group consisting of a polyphosphate, phosphorylated amino acid, bisphosphonate, citric acid, tartaric acid and any combination thereof. According to one embodiments, the polyphosphate is selected from the group consisting of triphosphate, pyrophosphate, and hexametaphosphate, the phosphorylated amino acid is phosphoserine or phosphothreonine, and the bisphosphonate is selected from the group consisting of alendronate, etidronic acid, zoledronic acid and medronic acid.

According to some embodiments, the stabilized ACC comprises less than 20 wt %, less than 15 wt %, less than 10 wt %, or less than 5 wt % of the stabilizing agent. In some embodiments, the stabilized ACC comprises up to 5 wt % of the stabilizing agent.

According to one embodiment, the average diameter of the stabilized ACC primary particles is about 10 nm to about 5 μm. According to another embodiment, the average diameter of the ACC primary particles is about 30 nm to about 400 nm. According to yet another embodiment, the average diameter of the ACC primary particles is about 30 nm to 350 nm. According to certain embodiments, the average diameter of the ACC primary particles is about 35 nm to 300 nm, 40 nm to about 250 nm, about 45 nm to about 200 nm, about 50 nm to about 150 nm or about 60 nm to about 100 nm. According to still another embodiment, the primary particles of ACC are aggregated and an average diameter of the aggregates is between 0.5 μm and 300 μm. According to one further embodiment, the diameter of aggregates of the ACC primary particle is about 1 to about 100 μm, about 10 to about 50 μm or about 20 to about 40 μm. According to another embodiment, the average diameter of the aggregates of the ACC primary particle is between 1 μm and 10 μm.

According to any one of the above embodiments, the final concentration of stabilized ACC in the cell culture medium is about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM. According to some embodiments, the concentration of stabilized ACC in the cell culture medium is about 0.0001% w/v to about 1% w/v about 0.0005% w/v to about 0.5% w/v, about 0.001% w/v to about 0.1% w/v, about 0.005% w/v to about 0.05% w/v, about 0.01% w/v to about 0.03% w/v.

According to some more specific embodiments, the present invention provides a cell culture medium supplemented with ACC stabilized by at least one stabilizing agent, wherein the stabilizing agent is selected from polyphosphate such as inorganic polyphosphate, phosphorylated amino acid, bisphosphonate, organic acid and any combination thereof; and the cell culture medium is suitable for growth of (i) muscle, nerve or bone cell or tissue culture, (ii) human or non-human mammal embryos, (iii) stem cells, (iv) gamete cells, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to a further embodiment, the stabilizing agent is a combination of triphosphate such as sodium triphosphate with organic acid, such as citric acid. According to one embodiment, such cell culture medium is suitable for growth of muscle, nerve or bone cell or tissue cultures. According to more particular embodiment, the cell culture medium is capable of supporting and enhancing growth, e.g. proliferation, maturation, development or differentiation of the cells. According to one embodiment, the cells are nerve cells and more particular damaged nerve cells. Thus according to one embodiment, such cell culture medium is capable of enhancing regeneration of damaged nerve cells. According to another embodiment, the cells are muscle cells, in particular dystrophic muscle cells such as Duchenne muscular dystrophic cells. Thus, according to one embodiment, the cell culture medium is capable of enhancing myotube formation and/or contractility onset. According to another embodiment, such cell culture medium is suitable for growth of human or non-human mammal embryos. In one particular embodiment, the cell culture medium is suitable for growth of human embryos. In even more particular embodiment, the cell culture medium is capable of enhancing development of human embryos. According to another embodiment, such cell culture medium is suitable for growth of human or non-human mammal gamete cells. In one particular embodiment, the cell culture medium is suitable for maturation of human gamete cells. In even more particular embodiment, the cell culture medium is capable of enhancing maturation of human gamete cells. According to another embodiment, the cell culture medium is capable of maturation of human sperm, e.g. enhancing sperm motility, enhancing sperm progressive motility, increasing sperm count, and any combination thereof. According to further embodiment, such cell media culture is suitable for growth of stem cells, and in particular human stem cells. According to some embodiments, the stem cells are selected from embryonic, chorionic, amniotic, hematopoietic, mesenchymal, neural, glial, adult and induced pluripotent stem cells. According to one embodiment, such cell culture medium is suitable for proliferation and/or differentiation of stem cells. According to one particular embodiment, such cell culture medium is capable of enhancing differentiation of stem cells such as MBA13 to osteoblasts. According to some embodiments the final concentration of stabilized ACC in the cell culture medium is about 0.1 to about 8 mM, about 0.5 to about 6 mM, about 1 to about 5 mM, or about 2 to about 4 mM. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%. According to any one of the above embodiments, the growth is performed in microgravity conditions. According to some embodiments, the growth is performed in space.

According to some embodiments, the present invention provides a cell culture medium such as cleavage, monoculture or sequential medium supplemented with ACC stabilized by at least one stabilizing agent, wherein the agent is phosphoserine or sodium triphosphate, optionally in combination with citric acid, the final concentration of stabilized ACC in the cell culture medium is about 0.1 to about 8 mM, about 0.5 to about 6 mM, about 1 to about 5 mM, or about 2 to about 4 mM, and the cell culture medium is capable of enhancing growth such as development of human embryos.

According to some embodiments, the present invention provides a cell culture medium such as media for sperm separation, wash or maturation such as ISolate®, PureCeption™ Multipurpose Handling Medium® (MHM®), Quinns™ Sperm Washing Medium, Multipurpose Handling Medium® (MHM®) and Modified HTF Medium with Gentamicin, supplemented with ACC stabilized by at least one stabilizing agent, wherein the agent is phosphoserine or sodium triphosphate, optionally in combination with citric acid, the final concentration of stabilized ACC in the cell culture medium is about 0.1 to about 8 mM, about 0.5 to about 6 mM, about 1 to about 5 mM, or about 2 to about 4 mM, and the cell culture medium is capable of enhancing maturation of sperm cells, e.g. enhancing sperm motility, enhancing sperm progressive motility, increasing sperm count, and any combination thereof.

According to other embodiments, the present invention provides a cell culture medium supplemented with ACC stabilized by at least one stabilizing agent, wherein the agent is phosphoserine, etidronic acid or sodium triphosphate, optionally in combination with citric acid, and the cell culture medium is capable of enhancing regeneration of nerve cells.

According to other embodiments, the present invention provides a cell culture medium such as DMEM/F12 or DMEM/F12 optionally supplemented with horse serum (HS), L-Glutamine, Gentamycine, and Insulin, wherein said medium is further supplemented with ACC stabilized by phosphoserine, etidronic acid or sodium triphosphate, optionally in combination with citric acid, wherein the final concentration of stabilized ACC in the cell culture medium is about 0.1 to about 8 mM, about 0.5 to about 6 mM, about 1 to about 5 mM, or about 2 to about 4 mM and said cell culture medium is capable of enhancing myotube formation and/or the onset of contractility in skeletal muscle cell e.g. in case of Duchenne muscular dystrophy.

According to other embodiments, the present invention provides a cell culture medium supplemented with ACC stabilized by phosphoserine, etidronic acid or sodium triphosphate, optionally in combination with citric acid, and said cell culture medium is capable of enhancing differentiation of stem cells, in particular differentiation of MBA13 to osteoblasts, wherein the final concentration of stabilized ACC in the cell culture medium is about 0.1 to about 8 mM, about 0.5 to about 6 mM, about 1 to about 5 mM, or about 2 to about 4 mM.

According to other embodiments, the present invention provides a cell culture medium such as DMEM/F12 or DMEM/F12 with 10% fetal bovine serum (FBS), 2 mM glutamine, 25 μg/mL gentamicin and 0.3-0.5% NVR-Gel, wherein said medium is further supplemented with ACC stabilized by phosphoserine, etidronic acid or sodium triphosphate, optionally in combination with citric acid, wherein the final concentration of stabilized ACC in the cell culture medium is about 0.1 to about 8 mM, about 0.5 to about 6 mM, about 1 to about 5 mM, or about 2 to about 4 mM and said cell culture medium is capable of enhancing preservation of ovaries.

According to another aspect, the present invention provides amorphous calcium carbonate (ACC) stabilized by at least one stabilizing agent, for use as a supplement to a cell culture medium. The terms "supplement" and "cell culture medium supplement" are used herein interchangeably and refer to one or multiple components for addition to cell culture media. In one particular embodiment, the term refers to stabilized ACC added or intended to be added to a cell culture medium. According to one embodiment, the stabilized ACC is added to the medium during the preparation of the medium. According to another embodiment, the ACC is added to the medium prior use.

According to one embodiment, the stabilized ACC is for use as a supplement to a cell culture medium suitable for growing a biological culture.

According to some embodiments, the stabilized ACC of the present invention when added to the cell culture media enhances the growth of cells. According to any one of the above embodiments, the growth is performed in microgravity conditions. According to some embodiments, the growth is performed in space. Therefore, in one embodiment, the stabilized ACC for use as a supplement to cell culture medium is capable of enhancing the growth of cells. In one embodiment, the stabilized ACC used as a supplement to a cell culture medium enhances proliferation, maturation, propagation, regeneration, development and/or differentiation of cells, tissues and organs. According to one embodiment, the ACC for use as a supplement to the cell culture medium of the present invention, is capable of enhancing differentiation of stem cells. According to another embodiment, such ACC for use as a supplement to the cell culture medium is capable of enhancing proliferation of cells. According to yet another embodiment, ACC for use as a supplement to cell culture medium is capable of enhancing maturation, e.g. of gametes, or enhancing development of cells, e.g. of embryos. According to certain embodiments, ACC for use as a supplement to cell culture medium is capable of enhancing regeneration of cells.

According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the cell culture medium supplement may be added to any known cell culture medium. According to some embodiments, the media is as defined hereinabove. According to one embodiment, the cell culture medium is selected from a natural medium and artificial medium. According to one embodiment, the media is suitable for growth of any biological culture, e.g. cell culture, tissue culture, organ culture, unicellular eukaryotes or microorganisms such as bacteria. According to one embodiment, the cell culture medium is suitable for growth of a culture selected from a culture of animal, plant or insect cells, tissues and/or organs. According to another embodiment, the cell culture medium is suitable for growth of bacteria or yeast.

According to some embodiments, the culture of animal cells is selected from a cell culture, tissue culture, organ culture, stem cells, gametes, embryos and an organ of human or non-human mammal. According to other embodiments, the mammal is a non-human mammal, e.g. livestock animals such as cattle, pigs, sheep, goats, horses, mules, asses, buffalo, or camels; a domestic pet e.g. a cat or dog; a rodent such as a mouse, rat, guinea pig or hamster; a lagomorpha such as a rabbit; or a primate such as a monkey (e.g. macaques) or an ape (e.g. chimpanzee). According to some embodiments, the stabilized ACC is for use as a supplement to cell culture medium suitable for growth of a primary or secondary culture. According to some embodiments, the stabilized ACC is capable of enhancing growth of said cell line. According to some embodiments, the stabilized ACC is for use as a supplement to cell culture medium suitable for growth of a mammal tissue culture. According to some embodiments, the stabilized ACC is for use as a supplement to cell culture medium suitable for growth of stem cells. According to another embodiment, the stem cells are human or non-human mammal stem cells.

According to some embodiments, the stabilized ACC is for use as a supplement to cell culture medium suitable for growth of embryos. According to one embodiment, the cell culture medium of the present invention is suitable for maturation and development of the embryos. According to another embodiment, stabilized ACC for use as a supplement to cell culture medium is capable of enhancing the development of embryos. According to one embodiment, the embryos are human embryos. According to another embodiment, the embryos are non-human mammal embryos.

According to some embodiments, the stabilized ACC is for use as a supplement to cell culture medium suitable for growth of gametes. According to one embodiment, the cell culture medium of the present invention is suitable for maturation or preservation of gamete. According to another embodiment, stabilized ACC for use as a supplement to cell culture medium is capable of enhancing the maturation or preservation of gametes, e.g. maturation or preservation of sperm or oocytes. According to any one of the above embodiments, the growth is performed in microgravity conditions. According to some embodiments, the growth is performed in space.

According to another embodiment, stabilized ACC for use as a supplement to cell culture medium is capable of enhancing cryopreservation of embryos or gametes, as describe hereinabove. According to any one of the above embodiments, the cryopreservation is performed in microgravity conditions, e.g. in space.

According to some embodiments, enhancing maturation of sperm is selected from enhancing sperm motility, enhancing sperm progressive motility, increasing sperm count, and any combination thereof. According to one embodiment, the sperm is human sperm. According to another embodiment, the sperm is a non-human mammal sperm. According to some embodiments, the stabilized ACC is for use as a supplement to cell culture medium suitable for growth of organ culture or organ. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary.

According to some embodiments, the stabilized ACC is for use as a supplement to cell culture medium suitable for growth of plant or insect cells.

According to some embodiments, the stabilized ACC is for use as a supplement to cell culture medium suitable to growth of animal, plant or insect cells and being a natural medium selected from biological fluids, tissue extracts and clots; or an artificial medium selected from a balanced salt solution, basal medium and complex medium.

According to some embodiments, the stabilized ACC is for use as a supplement to the cell medium selected from HI medium, DMEM, RPMI 1640, MEM, IMDM, L-15 Medium (Leibovitz), MCDB Medium, Medium 199, opti-MEM® and DMEM/F-12, Schneider's *Drosophila* medium, Grace's Insect medium, IPL-41 Insect Medium Sf-900™, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell™ Media, McCoy's 5A Modified Medium, NCTC Medium, Williams' Medium E, Waymouth Medium, TC-10 and IPL-10 medium. According to one embodiment, the stabilized ACC is for use as a supplement to the cell medium selected from Monoculture Media such as Quinn's Advantage™ (SAGE) medium 1-Step™, Sequential Media such as Quinn's Advantage™, Sequential Media (ORIGIO), MEDI-CULT, universal IVM, HI medium, DMEM, RPMI 1640, MEM, IMDM, opti-MEM®, GMEM, Ham's F-12, DMEM/F-12, Schneider's *Drosophila* medium, Grace's Insect medium, Sf-900™, TC-10, IPL-10, B5, N6 and Nitsch's medium. According to some embodiments, the stabilized ACC is for use as a supplement to the cell medium selected from media for sperm, media for sperm or maturation such as ISolate®, PureCeption™, Multipurpose Handling Medium® (MHM®), Quinns™ Sperm Washing Medium, Multipurpose Handling Medium® (MHM®) and Modified HTF Medium with Gentamicin, medium for fertilization, medium for embryo development, and medium for embryo or/and gamete maturation, handling and/or cryopreservation.

According to these embodiments, the ACC for use as a supplement to cell culture medium is capable of enhancing growth cell culture, tissue culture or organ culture when added to cell culture medium.

According to some embodiments, the stabilized ACC is for use as a supplement to cell culture media suitable for growth of unicellular eukaryotes. According to one embodiments, the unicellular eukaryotes are yeasts such as *Saccharomyces*, more particular *Saccharomyces cerevisiae*. According to one embodiment, the stabilized ACC is for use as a supplement to YPD, YPG or YPAD media.

According to some embodiments, the stabilized ACC is for use as a supplement to cell culture medium suitable for growth of prokaryotes, e.g. bacteria. In some embodiments, the bacteria is *E. coli* or probiotic bacteria such bacteria of *Bifidobacterium* and *Lactobacillus* genera. According to one embodiment, the stabilized ACC is for use as a supplement to LB and M9 media.

According to these embodiments, the ACC for use as a supplement to cell culture medium is capable of enhancing growth of said yeast or said bacteria when added to cell culture medium.

According to some embodiments, the stabilized ACC is for use as a supplement to cell culture medium suitable for growth of archaea.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to some embodiments, stabilized ACC for use as a supplement to cell culture medium stays stable in amorphous phase in a dry form for a period of at least 7 days, at least one month, at least 3 months, at least 6 months, or at least one year. In other embodiments, the stabilized ACC stays stable in amorphous phase when dispersed in a cell culture medium for at least one hour, for a period of at least 4, 6, 8, 12 or 24 hours, at least 7 days, or at least one month.

According to any one of the above embodiments, the stabilized ACC for use as a supplement for cell culture medium may be formulated as a solid, liquid or semi-liquid from. According to some embodiments, the stabilized ACC for use of the present invention is formulated in a solid form e.g. powder, tablets, capsules, or granules. In one particular embodiment, the stabilized ACC for use as a supplement is formulated as a powder. According to some embodiments, the stabilized ACC for use as a supplement is formulated as a liquid or semi-liquid form. According to one embodiment, the liquid form is a suspension or emulsion and the semi-liquid form is a gel or viscous suspension such as colloidal suspensions. In one specific embodiment, the stabilized ACC is formulated as a suspension. Therefore in one embodiment, the stabilized ACC for use as a supplement to cell culture medium is added to a cell culture medium either during the preparation of a cell culture medium or prior to use of that media, as a powder or as a suspension. According to one even more specific embodiment, the stabilized ACC is added as a freshly prepared suspension.

According to one embodiment, the average diameter of the stabilized ACC primary particles is about 10 nm to about 5 μm. According to another embodiment, the average diameter of the ACC primary particles is about 30 nm to about 400 nm. According to yet another embodiment, the average diameter of the ACC primary particles is about 30 nm to 350 nm.

According to certain embodiments, the average diameter of the ACC primary particles is about 35 nm to 300 nm, 40 nm to about 250 nm, about 45 nm to about 200 nm, about 50 nm to about 150 nm or about 60 nm to about 100 nm. According to still another embodiment, the primary particles of ACC are aggregated and an average diameter of the aggregates is between 0.5 μm and 300 μm. According to one further embodiment, the diameter of aggregates of the ACC primary particle is about 1 to about 100 μm, about 10 to about 50 μm or about 20 to about 40 μm. According to another embodiment, the average diameter of the aggregates of the ACC primary particle is between 1 μm and 10 μm.

According to any one of the above embodiments, the ACC for use as a supplement to the cell culture medium is added to a cell culture medium at the final concentration of about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM According to some more specific embodiments, the present invention provides ACC stabilized by at least one stabilizing agent selected from polyphosphate such as organic polyphosphate, phosphorylated amino acid, bisphosphonate, organic acid and any combination thereof for use as a supplement to a cell culture medium suitable for growth of (i) muscle, nerve or bone cell or tissue cultures, (ii) human or non-human mammal embryos, (iii) stem cells, (iv) gametes, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to further embodiment, the stabilizing agent is a combination of triphosphate such as sodium triphosphate with organic acid, such as citric acid. According to one embodiment, such cell culture medium is suitable for growth of muscle, nerve or bone cell or tissue culture. According to one embodiment, the stabilized ACC supplementing said cell culture medium is capable of enhancing growth, e.g. proliferation, development, maturation or differentiation of the cells. According to one embodiment, the cells are nerve cells and more particular damaged nerve cells. According to one embodiment, the stabilized ACC for use as a supplement to cell culture medium is capable of enhancing regeneration of damaged nerve cells. According to another embodiment, the cells are muscle cells, in particular dystrophic muscle cells such as Duchenne muscular dystrophic cells. According to one embodiment, the stabilized ACC for use as a supplement to cell culture medium is capable of enhancing myotube formation and/or the onset of contractility of muscle cells. According to one embodiment, the stabilized ACC for use as a supplement to cell culture medium is capable of enhancing development of human embryos. According to one embodiment, the stabilized ACC for use as a supplement to cell culture medium is capable of enhancing maturation or preservation of gamete, and in particular sperm. According to another embodiment, stabilized ACC for use as a supplement to cell culture medium is capable of enhancing cryopreservation of embryos or gametes, as describe hereinabove. According to one embodiment, the stabilized ACC for use as a supplement to cell culture medium is capable of enhancing sperm motility, enhancing sperm progressive motility, increasing sperm count, and any combination thereof. According to further embodiment, the stabilized ACC for use as a supplement is capable of enhancing the growth, e.g. proliferation, expansion and/or differentiation, of stem cells, and in particular human stem cells. According to some embodiments, the stem cells are selected from embryonic, chorionic, amniotic, hematopoietic, mesenchymal, neural, glial, adult and induced pluripotent stem cells. According to one embodiment, the cell culture medium supplemented with stabilized ACC is capable of enhancing the growth parameters, e.g., proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the present invention provides stabilized ACC for use as a supplement to cleavage, monoculture or sequential medium wherein the stabilizing agent is phosphoserine or sodium triphosphate, optionally in combination with citric acid, and said stabilized ACC is capable of enhancing development of human embryos.

According to some embodiments, the present invention provides stabilized ACC for use as a supplement to cell culture medium, wherein the agent is phosphoserine, etidronic acid or sodium triphosphate, optionally in combination with citric acid, and said stabilized ACC is capable of enhancing regeneration of nerve cells.

According to some embodiments, the present invention provides stabilized ACC for use as a supplement to DMEM/F12 or DMEM/F12 optionally supplemented with horse serum (HS), L-Glutamine, Gentamycine, and Insulin, wherein the stabilizing agent is selected from phosphoserine, etidronic acid or sodium triphosphate, optionally in combination with citric acid, and said stabilized ACC is capable of enhancing myotube formation and/or the onset of contractility in skeletal muscle cell e.g. in case of Duchenne muscular dystrophy.

According to some embodiments, the present invention provides ACC stabilized by phosphoserine, etidronic acid or sodium triphosphate, optionally in combination with citric acid, for use as a supplement to a cell culture medium, and thereby being capable of enhancing differentiation of stem cells, in particular differentiation of MBA13 to osteoblasts. According to any one of the above embodiments, the growth is performed in microgravity conditions. According to some embodiments, the growth is performed in space.

According to some embodiments, the present invention provides ACC stabilized by phosphoserine, etidronic acid or sodium triphosphate, optionally in combination with citric acid, for use as a supplement to media for sperm separation, wash or maturation such as ISolate®, PureCeption™, Multipurpose Handling Medium® (MHM®), Quinns™ Sperm Washing Medium, Multipurpose Handling Medium® (MHM®). Modified HTF Medium with Gentamicin, and thereby being capable of enhancing maturation of sperm cells, e.g. enhancing sperm motility, enhancing sperm progressive motility, increasing sperm count, and any combination thereof. According to any one of the above embodiments, the growth is performed in microgravity conditions. According to some embodiments, the growth is performed in space.

the present invention provides ACC stabilized by phosphoserine, etidronic acid or sodium triphosphate, optionally in combination with citric acid, for use as a supplement to a medium such as DMEM/F12 or DMEM/F12 with 10% fetal bovine serum (FBS), 2 mM glutamine, 25 μg/mL gentamicin and 0.3-0.5% NVR-Gel, thereby enhancing preservation of ovaries.

According to some embodiments, the final concentration of stabilized ACC in the cell culture media is about 0.1 to about 8 mM, about 0.5 to about 6 mM, about 1 to about 5 mM, or about 2 to about 4 mM.

According to yet another aspect, the present invention provides a cell culture medium supplement comprising amorphous calcium carbonate (ACC) stabilized by at least one stabilizing agent.

According to one embodiment, the cell culture medium supplement comprising the stabilized ACC is added to the medium during the preparation of the medium. According to another embodiment, the supplement is added to the medium prior use. According to any one of the above embodiments, the use is in microgravity conditions. According to some embodiments, the use is performed in space.

According to some embodiments, the cell culture medium supplement is a solid supplement. According to other embodiments, the supplement is a liquid or semi-liquid supplement.

According to any one of the above embodiments, the ACC is stabilized by at least one stabilizing agent as defined hereinabove. According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

The cell culture medium supplement of the present invention comprising stabilized ACC may be added to any cell culture medium described hereinabove. In one embodiment, the cell culture medium supplement comprising stabilized ACC may be added to a cell culture medium suitable for growing a biological culture, e.g. culture of cell, tissue culture, organ culture or organs. The cells may be eukaryotic or prokaryotic. In particular the cell culture medium refers to medium suitable for growth eukaryotic cell culture, tissue culture or organ. According to some embodiments, the cell culture is suspension or adherent cell culture. In some particular embodiments, the medium may be a complete medium, a basal medium, a basal medium supplemented with cell culture medium supplement, medium with various amounts of serum or chemically defined medium.

According to some embodiments the cell culture medium supplement comprising stabilized ACC is capable of enhancing the growth of cells or tissues. Thus in one embodiment, cell culture medium supplement comprising stabilized ACC is capable of enhancing proliferation, maturation, propagation, regeneration, development and/or differentiation of cells, tissues and organs. According to one embodiment, the supplement is capable of enhancing differentiation of stem cells. According to another embodiment, the supplement is capable of enhancing proliferation of a culture of cells. According to yet another embodiment, supplement is capable of enhancing maturation and/or development of cells or tissues. According to certain embodiments, the supplement is capable of enhancing regeneration of cell. According to some embodiments, the cell are eukaryote cells. According to one embodiments, the eukaryote cells are animal, plant, and insect cells. According to a further embodiment, the culture of animal cells is selected from a cell culture, tissue culture, organ culture, stem cells, gametes, embryos and an organ of human or non-human mammal. According to some embodiments the mammal is human, and the culture of human cells is selected from a human cell, tissue culture, and organ culture. According to other embodiments, the mammal is a non-human mammal. According to some embodiments, the cell culture, either human or non-human mammal cell culture is selected from a cell culture of nerve, muscle, epithelial, bone, adipose, stem cells, gametes, and blood cell. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the cell culture medium supplement comprising stabilized ACC may be added to a the cell culture medium suitable for growth of yeast and said cell culture medium is selected from YPD, YPG and YPAD.

According to some embodiments, the cell culture medium supplement comprising stabilized ACC may be added to a the cell culture medium suitable for growth of prokaryotes, said medium is selected from LB and M9.

According to some embodiments, the cell culture medium supplement comprising stabilized ACC is capable of enhancing the growth of yeast and bacteria.

According to some more specific embodiments, the present invention provides a cell culture medium supplement comprising ACC stabilized by at least one stabilizing agent, wherein the agent is selected from phosphorylated amino acid, polyphosphate, bisphosphonate, organic acid and any combination thereof. According to some embodiments, the supplement is added to a cell culture medium suitable for growth of (i) muscle, nerve or bone cell or tissue cultures, (ii) human or non-human mammal embryos, (iii) stem cells, (iv) gametes, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to further embodiment, the stabilizing agent is a combination of triphosphate such as sodium triphosphate with organic acid, such as citric acid. According to more particular embodiment, the cell culture medium supplement is capable of enhancing growth, e.g. proliferation, differentiation, development or maturation of the cells. According to one embodiment, such cell culture medium supplement is capable of enhancing regeneration of damaged nerve cells. According to another embodiment, such cell culture medium supplement is capable of enhancing myotube formation and/or promoting the onset of contractility of the myotubes. According to a further embodiment, such cell culture medium supplement is capable of enhancing development of embryos such as human embryos. According to a further embodiment, such cell culture medium supplement is capable of enhancing maturation or preservation of gametes and in particular of sperm. According to one particular embodiment, such cell culture medium supplement is capable of enhancing cryopreservation of embryos or gametes, as describe hereinabove. According to one embodiment, such cell culture medium is suitable for proliferation and differentiation of stem cells. According to some embodiments, the stem cells are selected from embryonic, hematopoietic, mesenchymal, neural, glial, adult and induced pluripotent stem cells. According to another embodiment, such cell culture medium supplement is capable of enhancing differentiation of stem cells. According to one particular embodiment, such cell culture medium supplement is capable of enhancing differentiation of stem cells such as MBA13 to osteoblasts. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the present invention provides a cell culture medium supplement comprising ACC stabilized by at least one stabilizing agent selected from phosphoserine, etidronic acid or sodium triphosphate, optionally in combination with citric acid. According to one embodiment, the supplement is added to cleavage, monoculture or sequential medium therefore enhancing development of human embryos. According to one embodiment, the supplement is added to a media for sperm separation, wash or maturation such as ISolate®, PureCeption™, Multipurpose Handling Medium® (MHM®), Quinns™ Sperm Washing Medium, Multipurpose Handling Medium® (MHM®) or Modified HTF Medium with Gentamicin, therefore enhancing maturation or preservation of gametes and in particular sperm. According to another embodiment, such supplement is added to a cell culture medium suitable for growth of nerve cells, therefore enhancing regeneration of nerve cells. According to a further embodiment, the supplement is added to DMEM/F12 medium or DMEM/F12 medium optionally further supplemented with horse serum (HS), L-Glutamine, Gentamycine, and Insulin, thereby enhancing myotube formation in skeletal muscle cell e.g. in case of Duchenne muscular dystrophy. According to yet another embodiment, the supplement is added to a cell culture medium suitable for growth of stem cell, thereby enhancing differentiation of stem cells, in particular differentiation of MBA13 to osteoblasts. According to other embodiments, the supplement is added to medium such as DMEM/F12 or DMEM/F12 with 10% fetal bovine serum (FBS), 2 mM glutamine, 25 μg/mL gentamicin and 0.3-0.5% NVR-Gel, thereby enhancing preservation of ovaries. According to some embodiments, the final concentration of stabilized ACC in the cell culture media is about 0.1 to about 8 mM, about 0.5 to about 6 mM, about 1 to about 5 mM, or about 2 to about 4 mM.

According to any one of the above embodiments, the term "comprise" has the meaning of "consist", therefore according to such embodiment, the cell culture medium supplement consists of ACC stabilized by at least one stabilizer.

According to a further aspect, the present invention provides amorphous calcium carbonate (ACC) stabilized by at least one stabilizer and formulated as a supplement for cell culture medium.

According to certain aspects, the present invention provides a method for enhancing growth of a biological culture, said method comprises exposing said culture to ACC stabilized by at least one stabilizer. According to one embodiment, the biological culture is selected from eukaryote cells, tissue or organ and prokaryote cells. According to any one of the above embodiments, the growth is performed in microgravity conditions. According to some embodiments, the growth is performed in space.

According to other embodiments, the method comprises enhancing the growth, e.g. enhancing the proliferation, maturation, propagation, regeneration, differentiation and/or development of the biological culture such as cells, tissues and organs.

According to one embodiment, the culture of cells is selected from animal, plant or insect cell culture. According to another embodiment, the tissue culture is selected from animal, plant or insect tissue culture. According to a further embodiment, the organ culture is selected from animal, plant or insect organ culture. According to some embodiments, the animal is a human or non-human mammal. According to certain embodiments, the non-human mammal is selected from livestock animals such as cattle, pigs, sheep, goats, horses, mules, donkeys, buffalo, or camels; a domestic pet e.g. a cat or dog; a rodent such as a mouse, rat, guinea pig or hamster; a lagomorpha such as a rabbit; and primates such as a monkey (e.g. macaques) or an ape (e.g. chimpanzee).

According to some embodiments, the mammal cell culture, either human or non-human mammal cell culture is selected from a cell culture of a nerve, muscle, epithelial, bone, adipose, stem cells, gametes and blood cell. According to one embodiment, the tissue culture is selected from epithelial, connective, muscular and nervous tissue culture. According to some more particular embodiments, the tissue culture is selected from kidney, hepatic, glandular, brain, bone, ocular and muscle tissue culture. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary.

According to one embodiment, the present invention provides a method for enhancing growth of muscle cells. According to another embodiments, enhancing growth of muscle cells comprises enhancing myotubes formation. According to some embodiments, the method comprises also reducing the time to the onset of spontaneous contractile activity of said myotubes. The time to the onset of spontaneous contractile activity is defined as a time needed to myoblasts to fuse and start spontaneously contracting. In one embodiment, the myocytes formed from said myoblasts are selected from skeletal myocytes or cardiac myocytes. In more particular embodiment, myocytes are skeletal myocytes. According to some embodiments, the method comprises enhancing myotube formation and/or the onset of contractility in skeletal muscle cell e.g. in case of Duchenne muscular dystrophy. According to any one of the above embodiments, the growth is performed in microgravity conditions. According to some embodiments, the growth is performed in space.

According to other embodiments, the method comprises enhancing growth of nerve cells. In one embodiment, enhancing growth of nerve cells comprises enhancing and acceleration nerve cells regeneration. Thus in one embodiment, the method comprises enhancing regrowth of axonal and dendritic neuronal fibers, of the peripheral and the central nervous system, and/or sprouting from damaged neuronal fibers. According to any one of the above embodiments, the growth is performed in microgravity conditions. According to some embodiments, the growth is performed in space.

According to some embodiments, the method comprises enhancing the maturation or preservation of gamete, e.g. enhancing in vitro maturation or preservation of sperm or oocyte. According to some embodiments, the gamete is selected from human gamete or non-human mammalian gamete. According to one embodiment, the gamete is sperm. Thus, in one embodiment, the present invention provides a method of enhancing maturation or ameliorating the quality of sperm said method comprises exposing said culture to ACC stabilized by at least one stabilizer. According to any one of the above embodiments, the growth is performed in microgravity conditions. According to some embodiments, the growth is performed in space.

According to one embodiments, ameliorating the quality of sperm is selected from the group consisting of enhancing sperm motility, enhancing sperm progressive motility, increasing sperm count, and any combination thereof.

According to some embodiments, increasing sperm count comprises increasing the sperm count in motility or progressive motility procedure. According to one embodiments, the motility or progressive motility procedure is a swim up procedure.

According to any one of the above embodiments, the sperm is a sperm of a human or non-human mammal. According to some embodiments the non-human mammal is selected from the group consisting of livestock animals, domestic pets, rodents, wild animals and primate.

In one embodiment, the livestock animals is selected from cattle, pigs, sheep, goats, horses, mules, asses, buffalo, and camels. In some other embodiments, the domestic pet is a cat or dog, the rodent is rat, mice, guinea pig or hamster, the lagomorpha is a rabbit, and the primate is monkey such as macaques or ape such as chimpanzee.

According to another embodiment, the sperm is a sperm of a non-mammal animal.

According to some embodiments, the non-mammal animal is selected from the group consisting fish, insects and birds.

According to one embodiment, the sperm is human sperm. According to other embodiments, the method comprises enhancing in vitro embryo development.

According to some embodiments, the method comprises enhancing stem cells differentiation and/or proliferation. According to some embodiments, the stem cells are selected from embryonic, chorionic, amniotic, hematopoietic, mesenchymal, neural, glial, adult and induced pluripotent stem cells. According to one embodiment, the method comprises enhancing differentiation of stem cells such as MBA13 to osteoblasts. According to any one of the above embodiments, the differentiation and/or proliferation occurs in microgravity conditions, e.g. in space.

According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the culture of cells is a culture of bacteria or yeast, thus according to such embodiments, the method comprises enhancing the growth of yeast or bacteria. In some embodiments, the bacteria is *E. coli* or probiotic bacteria such bacteria of *Bifidobacterium* and *Lactobacillus* genera.

According to any one of the above embodiments, exposing cells to ACC stabilized by at least one stabilizing agent comprising adding said ACC to a cell culture medium. The terms "exposing to" and "contacting with" are used herein interchangeably are refer to placing or transferring cells to a medium comprising the component of interest, such as stabilized ACC or adding the component, e.g. stabilized ACC to a medium in which the cells are grown or cultured. The cell media may be any know media in the art. According to some embodiments, the media as defined hereinabove. According to one embodiment, the cell culture medium is selected from a natural medium and artificial medium. According to some embodiments, the natural medium comprises biological fluid selected from plasma, serum, lymph, human placental cord serum, and amniotic fluid. According to another embodiment, the natural medium comprises tissue extracts such as extract of liver, spleen, tumors, leucocytes and bone marrow, extract of bovine embryo and chick embryos. According to a further embodiment, the natural medium comprises coagulants or plasma clots. According to some embodiments, the medium is an artificial medium supplemented with ACC stabilized by at least one stabilizing agent. According to one embodiment, the artificial medium is a balanced salt solution. Examples of balanced salt solution are PBS, DPBS, HBSS, EBSS Tyrode's T6, WM1, Pool's P1, Quinn's HTF, and Gardner's G1. According to another embodiment, the artificial medium is a basal medium. According to some embodiments, the medium may be further supplemented as well known in the art. According to one embodiment, the medium is supplemented with serum, e.g. fetal bovine serum. According to a further embodiment, the artificial medium is a complex medium.

According to one embodiment, the artificial medium is a serum free medium. According to a further embodiment, the artificial medium is a medium with reduced serum content. According to another embodiment, the artificial medium is a protein-free media.

According to one embodiment, the method comprises adding stabilized ACC to a cell culture medium selected from DMEM, EMEM, RPMI 1640 medium, Basal Medium Eagle (BME), Ham's F-10, Ham's F-12, DMEM/F-12, IMDM, opti-MEM®, GMEM, IPL-41 Insect Medium, Schneider's *Drosophila* medium, Grace's Insect medium, Serum-free Insect Media, Sf-900™, TC-10, Shields and Sang M3 Insect Medium, TC-100 Insect Medium, TNM-FH Insect Medium, IPL-10, Monoculture Media such as Quinn's Advantage™ (SAGE) medium 1-Step™ or Sequential Media such as Quinns Quinn's Advantage™ cleavage medium, Murashige and Skoog (MS), B5, N6, Nitsch's medium, NCTC Medium, MegaCell™ Media, Claycomb, Click's Medium, L-15 Medium, Medium 199, MCDB Media, Ames' Media, BGJb Medium, Click's Medium, CMRL-1066 Medium, McCoy's 5A Modified Medium, NCTC Medium, Swim's S-77 Medium, Waymouth Medium, William's Medium E, in vitro maturation media, Menezo's B2 and B3 media, Behr's Blastocyst Medium, Gardner's G2, universal IVM (ORIGIO) and sequential media for embryo growth. According to one embodiment, the method comprises adding stabilized ACC to a cell culture medium selected from Media for sperm separation, Media for sperm wash and Media for maturation, such as ISolate®, PureCeption™, Multipurpose Handling Medium® (MHM®), Quinns™ Sperm Washing Medium, Multipurpose Handling Medium® (MHM®). Modified HTF Medium with Gentamicin. According to one embodiment, the method comprises adding stabilized ACC to a cell culture medium selected from medium for fertilization, medium for embryo development, or medium for embryo or/and gamete maturation, handling and/or cryopreservation.

In some embodiments the cells are grown as stationary or immobilized cultures on a carrier such as Cytodex™ 1 or 3, Cytopore™ 2, polystyrene, gelatin, dextran, polyacrylamide or other substitutes carriers.

According to some embodiments, the cell culture medium is suitable for growth of unicellular eukaryotes. According to one embodiments, the unicellular eukaryotes are yeasts such as *Saccharomyces*, more particular *Saccharomyces cerevisiae*. According to one embodiment, the method comprises adding stabilized ACC to a cell culture medium suitable for growth of unicellular eukaryotes, e.g. *Saccharomyces cerevisiae*, said cell culture medium is selected from yeast extract peptone dextrose (YPD), Yeast extract-peptone-glycerol (YPG) and Yeast extract-peptone-dextrose (YPAD) media.

According some embodiments, the cell culture medium is suitable for the growth of prokaryotes, e.g., the bacteria is *E. coli* or probiotic bacteria such bacteria of *Bifidobacterium* and *Lactobacillus* genera. According to one embodiment, the method comprises adding stabilized ACC to a medium is suitable for growth of bacteria such as LB or M9.

According to any one of the above embodiments, the stabilized ACC is added to a cell culture medium at the final concentration of about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM.

According to one embodiment, the ACC is formulated in a form of a solid, liquid or semi-liquid. In one particular embodiment, the stabilized ACC is added in a form of a suspension. In yet another embodiment, the suspension is freshly prepared suspension.

According to any one of the above embodiments, the ACC is stabilized by at least one stabilizing agent defined hereinabove. In certain embodiments, the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate; an organophosphate compound; an organophosphonate compound; organic polyphosphate, an inorganic polyphosphate, an inorganic phosphorous acid, an organic compound having multiple functional groups as defined above; an inorganic phosphate and polyphosphate compound; an organic compound having a polyphosphate chain; an organic surfactant; a bio-essential inorganic ion; saccharides and derivatives thereof, proteins, phosphorylated proteins, natural and synthetic biopolymers and derivatives thereof or any combination thereof. According to another embodiment, the stabilizing agent is selected from the group consisting of phosphoserine, adenosine triphosphate, adenosine diphosphate, phytic acid, citric acid, etidronic acid, pyrophosphate, polyphosphate, triphosphate, ethanol, hexametaphosphate, chitin, and any combination thereof. The compound are as defined hereinabove. According to some embodiments, ACC is stabilized by more than one stabilizing agent, e.g. by 2 or 3 stabilizing agents.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to another aspect, the present invention provides a method of preparation of a cell culture medium comprising amorphous calcium carbonate (ACC) stabilized by at least one stabilizer, said method comprises adding the stabilized ACC to a cell culture medium.

According to some embodiments, the present invention provides a method for enhancing growth of a biological culture in microgravity conditions, comprising growing the biological culture in a cell culture medium comprising an amorphous calcium carbonate (ACC) stabilized by at least one stabilizer, wherein the growth of the biological culture is performed in microgravity conditions.

According to other embodiments, the present invention provides method for supporting growth of a biological culture in microgravity conditions, comprising growing the biological culture in a cell culture medium comprising an amorphous calcium carbonate (ACC) stabilized by at least one stabilizer, wherein the growth of the biological culture is performed in microgravity conditions. According to some embodiments, the method enhances proliferation of the biological culture in space. According to some embodiments, the method enhances maturation of the biological culture in space. According to some embodiments, the method enhances propagation of the biological culture in space. According to some embodiments, the method enhances regeneration of the biological culture in space. According to some embodiments, the method enhances differentiation of the biological culture in space. According to some embodiments, the method enhances development of the biological culture in space. According to some embodiments, the method enhances the survival of the biological culture in space microgravity. According to some embodiments, the method enhances the survival of the biological culture in radiation environment. According to some embodiments, the method supports proliferation of the biological culture in space. According to some embodiments, the method supports maturation of the biological culture in space. According to some embodiments, the method supports propagation of the biological culture in space. According to some embodiments, the method supports regeneration of the biological culture in space. According to some embodiments, the method supports differentiation of the biological culture in space. According to some embodiments, the method supports development of the biological culture in space. According to some embodiments, the method supports the survival of the biological culture in space microgravity. According to some embodiments, the method supports the survival of the biological culture in radiation environment. According to some embodiments, the biological culture is a culture of eukaryote.

According to some embodiments, the method comprises enhancing at least one of nerve cells regeneration; muscle cells formation and growth; stem cells differentiation; oocytes or sperm cells maturation; embryos development; embryo or gamete cryopreservation; myotubes formation; onset for muscle cell contraction; cell culture survival in space microgravity; cell culture survival in radiation environment; osteocytes formation; and cell fusion and conversion into fiber cells.

According to certain aspects, the present invention provides a kit comprising amorphous calcium carbonate (ACC) stabilized by at least one stabilizer and instruction for use of said ACC in combination with a cell culture medium. According to one embodiment, the stabilized ACC is ACC for use as a cell culture medium supplement. According to one embodiment, the present invention provides a kit comprising calcium chloride, sodium carbonate, at least one stabilizing agent and instruction for preparing stabilized ACC from said calcium chloride, sodium carbonate, at least one stabilizing agent and instruction for use of said stabilized ACC in combination with a cell culture medium. According to one embodiment, calcium chloride, sodium carbonate, and/or at least one stabilizing agent is present as an aqueous solution.

According another embodiment, the kit comprises cell culture medium supplement comprising ACC stabilized by at least one stabilizer and instructions for use of said supplement in combination with a cell culture medium. According to one embodiment, the cell culture medium supplement consists of ACC stabilized by at least one stabilizer.

According to any one of the above embodiments, the kit further comprises a cell culture medium, as defined hereinabove. Therefore, in one embodiment, the kit comprises ACC stabilized by at least one stabilizer, a cell culture medium and instructions for use. In other embodiments, the kit comprises culture medium supplement comprising ACC stabilized by at least one stabilizer, medium and instructions for use.

The ACC stabilized by at least one stabilizer and the cell culture medium are as described hereinabove.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to some embodiments, the ACC composition comprises a combination of the stabilizers disclosed above.

According to any one of the above embodiments, the stabilized ACC may be formulated as a solid, liquid or semi-liquid formulation. Thus in one embodiment, the stabilized ACC for use as a supplement of a cell culture medium is formulated as a solid, liquid or semi-liquid. According to some embodiments, the stabilized ACC is formulated in a solid form e.g. powder, tablets, capsules, or granules. Thus in one particular embodiment, the stabilized ACC for use as a supplement to a cell culture medium is formulated as a powder. According to other embodiments, the stabilized ACC for use as a supplement is formulated as a liquid or semi-liquid. According to one embodiment, the liquid form is a suspension or emulsion and the semi-liquid form is a gel or colloid. In one specific embodiment, the stabilized ACC is formulated as a suspension. Therefore, in one embodiment, the stabilized ACC formulated as powder or as a suspension is added to a cell culture medium prior to use of that media. According to one even more specific embodiment, the stabilized ACC is added as a freshly prepared suspension.

The kit of the present invention may further comprise a cell culture medium. The cell culture media are well known in the art and any medium may be used. In some embodiments, the cell culture medium is suitable for growing a biological culture, said culture is selected from a culture of cells, tissue culture, organ culture or organs. The culture of cells may be a culture of eukaryotic or prokaryotic cells. In particular the cell culture medium refers to medium suitable for growth eukaryotic cell culture, tissue culture or organ. In some particular embodiments, the medium may be a complete medium, a basal medium, a basal medium supplemented with cell culture medium supplement, medium with various amounts of serum or chemically defined medium.

According to some embodiments, the cell culture medium is selected from HI medium, DMEM, RPMI 1640, MEM, IMDM, L-15 Medium (Leibovitz), MCDB Medium, Medium 199, opti-MEM® and DMEM/F-12, Schneider's *Drosophila* medium, Grace's Insect medium, IPL-41 Insect Medium Sf-900™, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell™ Media, McCoy's 5A Modified Medium, NCTC Medium, Williams' Medium E, Waymouth Medium, TC-10 and IPL-10 medium. In one particular embodiment, the cell culture medium is selected from Monoculture Media such as Quinn's Advantage™ (SAGE) medium 1-Step™, Sequential Media such as Quinn's Advantage™ cleavage medium, MEDICULT, universal IVM, HI medium, DMEM, RPMI 1640, MEM, IMDM, opti-MEM®, GMEM, Ham's F-, DMEM/F-12, Schneider's *Drosophila* medium, Grace's Insect medium, Sf-900™, TC-10, IPL-10, B5, N6, or Nitsch's medium. Further examples of media are media for sperm separation such as ISolate®, PureCeption ", Multipurpose Handling Medium® (MHM®) and media for sperm wash such as Quinns™ Sperm Washing Medium, Multipurpose Handling Medium® (MHM®) and Modified HTF Medium with Gentamicin-HEPES. According to other embodiments, the medium is a medium for oocytes maturation such as SAGE™ In-Vitro Maturation Media (IVM) and BO-IVM Oocyte maturation medium. According to further embodiment, the cell culture medium is selected from medium for fertilization, medium for embryo development, and medium for embryo or/and gamete maturation, handling and/or cryopreservation. According to some embodiments, the cell culture medium is suitable for growth of yeasts and said cell culture medium is selected from YPD, YPG and YPAD.

According to some embodiments, the cell culture medium is suitable for growth of prokaryotes, said medium is selected from LB and M9.

According to one embodiment, the present invention provides a kit comprising calcium chloride, sodium carbonate, at least one stabilizing agent and instruction for preparing stabilized ACC and instruction for use of said ACC in combination with a cell culture medium. According to some embodiments, calcium chloride and sodium carbonate are present as water solutions. According to one embodiment, at least one stabilizing agent is present as one or two separate solutions. According to one embodiment, the instructions for preparing ACC comprise instructions for mixing the solution comprising calcium chloride and at least one stabilizer with sodium carbonate solution and further adding a solution comprising at least one stabilizing agent.

According to any one of the above embodiments, the kit is used in microgravity conditions. According to some embodiments, the kit is used in space.

In other aspects, the present invention provides stabilized ACC for use as a supplement for humans travelling to space to treat the weight loss of a musculoskeletal system mass. In other aspects, the present invention provides stabilized ACC for use as a supplement administered by humans travelling to space to treat muscle and/or bone loss. In certain aspects, the present invention provides stabilized ACC for use as a pharmaceutical composition administered by humans travelling to space to treat muscle and/or bone loss.

According one aspect, the present invention provides a pharmaceutical composition comprising a stabilized ACC for use in treating the weight loss of a musculoskeletal system mass in space flights that expose the subject to stressors such as microgravity, hyper-gravity, absence of hydrostatic pressure, and radiation.

According to another aspect, the present invention provides a method of preventing the loss in the mass of a musculoskeletal system in space microgravity, in a subject in need thereof, comprising administering to said subject an amorphous calcium carbonate stabilized by at least one stabilizing agent. According to some embodiments, method comprises preventing the loss in the mass of a bone. According to some embodiments, method comprises preventing the loss in the mass of a muscle.

According to another aspect, the present invention provides a method of treating damages caused by exposure to microgravity conditions in a subject in need thereof, comprising administering to said subject an amorphous calcium carbonate stabilized by at least one stabilizing agent. According to some embodiments, the damage comprises damage to a musculoskeletal system. According to some embodiments, the damage comprises a loss of the mass of a bone. According to some embodiments, the damage comprises a loss of the mass of a muscle. According to some embodiments, the exposure to microgravity conditions comprises a prolonged staying in space. According to some embodiments, the prolonged staying in space comprises staying above 1 days, above 7 days, above 14 days, above 1 month, above 2 months or above 6 months.

The term "musculoskeletal system" as used herein refers to the skeleton bones, muscles, cartilage, tendons, ligaments, joints, and other connective tissues are all part of the musculoskeletal system, which work together to provide the body with support, protection, and movement.

The terms "treating" and "treatment" are uses herein interchangeably and refer to taking steps to obtain beneficial or desired results, including clinical results. Beneficial or desired clinical results include, but are not limited to, alleviation or amelioration of one or more symptoms associated with bone and/or muscle loss.

As used herein, the term "preventing" when used in relation to a condition, refers to the administration of a composition which reduces the frequency of, or delays the onset of, symptoms of a medical condition in a subject relative to a subject which does not receive the composition. The term further refers to slowing down the process of development of the disease, condition or damage.

The composition of the present invention may be administered by any known method. The term "administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. According to some embodiments, the composition is administered 1, 2, 3, 4, 5 or 6 times a day. According to other embodiments, the composition is administered 1, 2, 3, 4, 5 or 6 times a month. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to some embodiments, the method comprises oral administration.

According to any one of the above embodiments, the composition of the present invention is formulated as a pharmaceutical composition, nutraceutical composition, a food supplement or a medical food.

According to one embodiment, the composition comprising a stabilized ACC for use in treatment of bone and/or muscle loss is a pharmaceutical composition. According to another embodiment, the composition comprising a stabilized ACC for use in treatment of bone and/or muscle loss is a nutraceutical composition. According to yet another embodiment, the composition comprising a stabilized ACC for use in treatment of bone and/or muscle loss is a food supplement. According to a further embodiment, the composition comprising a stabilized ACC for use in treatment of bone and/or muscle loss is a medical food.

The term "pharmaceutical composition" as used herein refers to any composition comprising a stabilized ACC and a pharmaceutically acceptable excipient.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

As used herein, the term "nutraceutical composition" refers to a composition suitable for use in human beings or animals, comprising one or more natural products with therapeutic action which provide a health benefit or have been associated with disease prevention or reduction.

The term "food supplement" is used to mean a product containing said composition and intended to supplement the food by providing nutrients that are beneficial to health according to any acceptable directive, such as European directive. For example, a food supplement may be a capsule or a tablet for swallowing, or a powder or small vial to mix with a food and providing beneficial health effects.

As used herein, the term "medical food" refers to a food item specially formulated for the dietary management of a disease or disorder in a subject.

The composition of the present invention may be formulated as defined hereinabove. In one particular embodiment, the composition comprising a stabilized ACC is formulated as a solid dosage form selected from tablets, capsules, powder or granules. In another embodiment, the composition comprising a stabilized ACC is formulated as a liquid or semi-liquid dosage form selected from an elixir, tincture, suspension, syrup, emulsion or gel. According to a further embodiment, the composition is formulated as a composition for inhalation.

According to some embodiments, of the present invention, the terms "capable of enhancing" and "enhances" in some embodiments are used interchangeably In any one of the above embodiments, the term "comprising" includes the meaning of "consisting" and may be substituted by it.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Methods

Culture Medium

The culture medium was composed of: 90% Dulbecco's modified eagle medium-nutrient mixture F-12(DMEM-F12) calcium depleted (medium without calcium ions, (special preparation), 10% heat-inactivated fetal bovine serum (FBS), 6 g/L D-glucose, 2 mM glutamine, 25 μg/mL gentamicin and 0.05 ng/mL insulin-like growth factor 1 (IGF-I) (all purchased from Biological-Industries, Israel).

NVR-Gel as a Substrate for Neuronal Cultivation

Neural and Vascular Reconstruction Gel (NVR-Gel, NVR Labs proprietary) is composed of two main components: high molecular hyaluronic acid (HA, $3\times10^6$ Da, BTG, Israel) and laminin (Sigma). For neuronal cell cultivation, NVR-Gel of 1% was diluted with culture medium to a final concentration of 0.3-0.5%. The gel has the texture of a viscous liquid, it adheres easily and successfully the embedded cells or explants to the plastic or glass substratum, and enabled nerve fiber outgrowth in a 3D pattern.

Preparation of Neuronal Tissue Cultures

All the experiments were carried out and authorized by the local ethics committee recognized by the Israeli authorities for animal experimentation. Stationary organotypic cultures of dorsal root ganglia (DRG) and spinal cord (SC) as well as cultures of dissociated brain cells were prepared from rat fetuses (15 days of gestation, Lewis inbred, Harlan, Israel). Immediately after dissection, the isolated tissues were cut with a McIlwain™ tissue chopper into small slices (of 400 μm thickness). In these studies, two tissue culture strategies were used. In the first method, tissue slices were seeded directly in 12 well-culture plates containing 1 mL culture medium containing 0.3%-0.5% NVR-Gel. In the second method, the tissue slices were further dissociated with a trypsin-EDTA solution for 30 min, and washed with a culture medium. Subsequently, the dissociated cells were added to a suspension of chitosan powder or gastrolith powder (micro carriers, MCs) and incubated in suspension at 37° C. for 4 days. The formed floating cells/MCs aggregates were then collected and seeded in 12 well-culture plates containing 1 mL of culture medium containing 0.3%-0.5% NVR-gel.

$Ca^{2+}$ Supplement Source $Ca^{2+}$ source (listed below) at final concentration of 1 or 2 mM was added once to the gel at the seeding stage and then to the nutrient medium at each consecutive feeding. Calcium source were as following: ACC—Etidronic Acid (ACC-ET) (fresh suspension); ACC-Phosphoserine (ACC-PS) (fresh suspension); Gastrolith (dissolved with 0.1 M HCl and then neutralized with NaOH 1M); gastrolith powder; CCC—Aqueous suspension of crystalline calcium carbonate (commercial nanoparticles powder); and $CaCl_2$) solution—control.

The cultures were monitored by daily phase contrast microscopic observations starting from 24 hours after setting the cultures onward.

Suspensions of fresh ACC preparations consisted of particles forming a stable suspension. The gastrolith is a natural ACC isolated from crabs, and can be purchased only as a dry powder. In this form, its other characteristic components (such as calcium ions and proteins) are not available to the cells. In order to increase their bioavailability, the gastrolith powder was dissolved in 0.1 M HCl (which mimics the acidity which exists in the stomach) and then neutralized with 1M NaOH.

Immunofluorescent Staining of Neuronal Cultures

After removal of the culture medium, the dorsal root ganglia (DRG) cultures were washed with phosphate buffered salt solution (PBS) and fixed in 4% paraformaldehyde for 15 min, and then washed again with PBS. The fixed cells were permeabilized with 0.1% of Triton X-100 in PBS and then immuno-blocked (to avoid non-specific staining) with a 1% bovine serum albumin (BSA) in PBS for 1 h at room temperature. The specimens were then incubated with rabbit anti-neurofilament antibodies (NF, Novus Biologicals, 1:500) to visualize the neurite outgrowth. The primary antibodies were diluted in 0.1% BSA and 0.05% Tween® 20 (polysorbate 20) in PBS (diluents buffer) and incubated with the specimens overnight at 4° C. After rinsing with 0.05% Tween® 20 in PBS (wash buffer), the DRG specimens were incubated for 1 h at room temperature with the secondary antibodies Alexa Fluor® 594-conjugated donkey anti-rabbit IgG (Jackson ImmunoResearch, USA, 1:800 in a diluent buffer). Finally, the samples were rinsed again with wash buffer, and mounted with mounting medium (Immco Diagnostic, USA). All the images were observed with an Olympus IX70 microscope.

ACC Suspension Preparation

The ACC was added to commercial culturing media as a suspension, freshly prepared prior to mixing, using a proprietary procedure developed by Amorphical Ltd. The ACC-evolved practical suspensions can be phase-stabilized at room temperature for periods exceeding 1 month to prevent crystallization of the amorphous phase throughout the culturing procedures. Crystallization in the absence of adequate stabilizers results in a lack of efficacy as well as creates strong interference in the optical microscopy analysis. The ACC suspension in this series of experiments contained a calculated concentration of 0.3% $Ca^{2+}$. The suspension was added to different commercial media immediately after the suspension preparation and prior to cell seeding, generating a concentration of 2 mM or 1 mM $Ca^{2+}$ in the media. For example, to each 1 mL of muscle differentiation (fusion) medium (HI medium), 40 μL of ACC suspension was added and for the bone marrow-derived MSC (BM-MSC) media, 20 μL/mL of ACC suspension was added. In the media for muscle cells and BM-MSCs, the final calcium concentration was 2.0 mM and 2.5 mM, respectively.

Cell Culture Experiments

Preparation of Culture Plates for International Space Station (ISS) Experiments

To facilitate cell attachment to the specially designed microfluidic chip, the culture plates were precoated with 1 mg/mL bovine fibronectin (Sartorius, attachment solution, cat #05-752-1) diluted 1:100 in Dulbecco's phosphate-buffered saline (DPBS−). Five milliliters of the diluted fibronectin solution were added to each T-25 culture flask and 3 mL of the solution was injected to the chip. After incubation for 20 min at room temperature, excess solution was removed from flasks or washed away from the chip, using serum-free Dulbecco's modified Eagle medium (DMEM)/F12. Cells were seeded on top of the precoated flask or chip. For mouse bone marrow 13 (MBA-13) cells, the plates were precoated with diluted 1:100 fibronectin solution, incubated for 30 min in a $CO_2$ incubator, and then washed twice with DPBS−.

The culture plates were alternatively coated with gelatin. A stock solution of 1% porcine gelatin (Sigma, Millipore cat #04055) in water was sterilized through autoclaving. Once cooled, 500 μL of the solution was added to each well of a 12-well culture plate. After incubation for 20 min at room temperature, the excess solution was removed, and the cells were seeded.

Culture Media

For the proliferation stage, cells were cultured in DMEM/F12 (Sartorius 01-170-1A containing 1.05 mM $Ca^{2+}$) with 10% fetal bovine serum, 25 μg/mL gentamycin, and 2 mM 1-glutamine. For comparison in space, the standard DMEM/F12 was replaced with a calcium-depleted DMEM/F12 medium (Sartorius 06-1170-65-1A) and 2 mM calcium, derived from the ACC suspension or from calcium chloride ($CaCl_2$), was added.

For the fusion stage, the proliferation medium was changed to muscle cell differentiation (fusion) medium containing DMEM/F12 (Sartorius 01-170-1A with 1.05 mM $Ca^{2+}$), 2% horse serum (Sartorius 04-004-1A), 2 mM 1-glutamine, and 25 μg/mL gentamycin (all purchased from Sartorius Biological Industries, Israel). To each 100 mL complete medium, 60 μL of 5 mg/mL recombinant human insulin was added. For comparison in space, the DMEM/F12 medium was replaced with calcium-depleted DMEM/F12 medium (Sartorius 06-1170-65-1A) and 2 mM calcium, derived from the ACC suspension or from $CaCl_2$, was added.

Alizarin Red Staining

The pH of the Alizarin Red (Sigma; A55333) solution was adjusted to 4.2. The cells were washed twice with DPBS− and stained with 2% Alizarin Red solution for 15-20 min. Following incubation, the samples were washed 2-3 times with water to remove non-specific staining.

Alkaline Phosphatase Staining

Cells were washed once or twice with DPBS− and then fixed with 4% paraformaldehyde (PFA) for 20 min. The cells were washed three more times with DPBS−. Following removal of DPBS−, three drops of reagent from the Alkaline Phosphatase DAKO BCIP/NBT staining kit (Agilent Technologies, Inc. substrate system K0598) were used to cover the cells, including one empty well without any cells as a control to quantify the assay. Incubation was performed for 1 h and then the cells were rinsed with distilled water.

Remote-Controlled Microgravity Lab Operation

The in-orbit experiment was conducted using the remote-controlled lab-on-a-chip microgravity platform SPIC2 (SpacePharma R&D Israel Ltd.) consisting of 3.5 CubeSat units with dimensions of 35×10×10 cm and a total weight of 4.0 kg. (Amselem, Pharm Res. 2019; 36(12):1-15). The SPIC2 3.5U Microgravity Lab is equipped with a service module comprising an on-board computer and professional circuit design electronics, temperature control unit, fluid handling system, liquid reservoirs, a manifold that directs the fluid flow, a miniature microscope with a light source, and a spectrometer (Hamamatsu, Japan, with a wavelength range of 420-750 nm). The fluid handling system, composed of active and passive pumps and reservoirs for the solutions and reagents, is modular and connected to each microfluidics-based lab-on-a-chip through "plug and play" modes.

During the space operations, SpacePharma's SPIC2 3.5U Lab unit was accommodated in the ICECUBES Module (Belgium, US) providing power and data exchange via real-time interaction from the ground. The SPIC2 module was launched to space as part of Axiom Space AX-1's first private mission to the ISS (launched on Apr. 8, 2022, and returned to Earth on Apr. 25, 2022). During this mission, near real-time daily communication windows between the SPIC2 and ground (telemetry and telecommands) were performed for data and images downlink (microscope/telemetry) and for commands uplink. At the end of the mission, the SPIC2 module was disconnected, sent back to earth retrieved at the ground and shipped back for analysis at Amorphical's laboratory in Israel.

The Lab-on-a-Chip (LOC) is made of polystyrene and is composed of four separated flow chambers, split into duplicate reactions of 60 μL volume each. Duplicates were established for each cell type: experimental (ACC) and control ($CaCl_2$)). Each duplicate had its own inflow/outflow ports. Before cell seeding, the chambers were flushed with 70% EtOH, DMEM/F12 without serum, and coated with fibronectin at a concentration of 0.01 mg/mL for 20 min. Fibronectin was washed from the chambers (slots) using serum-free DMEM/F12. Cells (osteoblasts and myocytes) were seeded 2 days before launching into space and kept under controlled temperature (37° C.) and medium perfusion. Once in space, the SPIC2 system automatically controlled the temperature and media feeding into the different devices. Cell viability was monitored using an embedded miniatured microscope.

Lab Module and Microfluidic Chip Operation in Space

A microfluidic component that fits the IceCube Microgravity lab installation at the ISS was specially designed for this experiment. Cells were seeded into the fibronectin precoated microfluidic chip device, as described above. Each slot was precoated with fibronectin and each different culture cell type was seeded into its designated space with its own medium with or without ACC in duplicates. The microfluidic set up was connected to a specially designed Space Pharma advanced lab (SPAD) module that requires only placement inside the microgravity biolab and connection to its electricity. The SPAD module was sent back to Earth after 18 days in space and unpacked at Day 19 of the experiment, including 6 days of the culturing operation at the ISS before termination.

Cultures were monitored daily at the ISS by a special remotely operated microscope arrangement, starting 24 h after setting the cultures and onward. On the last day at the ISS in space, cultures were fixed with 4% PFA.

Evaluation of Staining Intensity in Muscle and Bone Cell Cultures

The microscopical stained areas were determined using the ImageJ Fuji software Pixel Counter application (Version 1.53t, U.S. National Institutes of Health, Bethesda, MD, USA) and the results were statistically compared using Student's t-test with GraphPad® Software (Prism® 7, San Diego, CA, USA), a software the combines scientific graphing, comprehensive curve fitting, statistics, and data organization.

Example 1. Effects of ACC on SC-DRG Co-Cultures

Results

The effect of various calcium preparations was examined in SC-DRG co-cultures. In general, the cultures contained 400 micron SC slices with attached or separated slices of DRG. It can be said that all of the examined ACC preparations (ACC-ET, ACC-PS, and gastrolith) enhanced significantly neuronal fiber regeneration in comparison to CCC and the $CaCl_2$). Table 1 shows the portion of explants (out of 6) which exhibited nerve fiber sprouting after 4 days of cultivation in the presence of the various calcium preparations ($Ca^{2+}$ concentration of 2 mM) or in the presence of stabilizers alone (the stabilizer was added at the concentration of 0.05% to each well (from a stock solution of 5%)). It can be seen that the most intensive sprouting was observed in cultures which were exposed to ACC-ET (100% of explants), followed by ACC-PS and Gastrolith (66.6% of explants). The CCC and $CaCl_2$) induced neuronal sprouting only from 50% of the explants, and the stabilizers alone even a lower percentage (0-33%) During the establishment of the cultures (after the first week of cultivation) the regenerated nerve fibers became longer, thicker and ramified, until the formation of neuronal networks, mainly in cultures exposed to the various ACC preparations (FIG. 1).

TABLE 1

| The effect of ACC preparations on early nerve fiber sprouting from SC-DRG co-cultures. | |
|---|---|
| Type of calcium preparation | Cultures with axonal regeneration (%) |
| ACC-ET (fresh suspension) | 100 |
| ACC-PS (fresh suspension) | 66.6 |
| Gastrolith | 66.6 |
| CCC (crystalline calcium carbonate) | 50 |
| $CaCl_2$ aqueous solution (control) | 50 |
| ET | 33.3 |
| PS | 0 |

Example 2. Effects of ACC on Brain Cultures

The effect of ACC was studied on cultures of brain cells-MCs aggregates seeded in gel after 4 days in suspension (see methods part of Example 1). The results are presented in FIG. 2 and show that the ACC enhanced nerve fibers regeneration, significantly more than the calcium chloride. This is especially notable when comparing the number and the length of nerve fibers between the two treatments.

Example 3—Effects of ACC Preparations on Healthy Skeletal Muscle Cells

Methods

Preparation of Skeletal Muscle Cultures

Stationary skeletal muscle cultures were prepared from healthy 1 day new born rat (Sprague Dawley, Harlan, Israel). The muscle tissue was dissected from posterior legs and was thoroughly minced. Digestion was performed with Trypsin-EDTA while gentle trituration. After 30 min the supernatant, containing dissociated cells, was collected and a fresh Trypsin-EDTA was added. This procedure was repeated two more times. Then, all supernatants were pooled, centrifuged, and the cell pellet was re-suspended in Proliferation Medium. Cells were seeded in a Gelatin coated 12 wells culture plates, $1\times10^5$ cells/well containing 1 mL of Proliferation Medium. Two days later, the medium was changed to Fusion Medium, which was then changed twice a week. The cultures were monitored by daily phase contrast microscopic observations from 24 hours after setting the cultures and onward. At predetermined days, cultures were fixed in methanol for 20 minutes and then stained with Giemsa in order to evaluate the number of myotubes formed with time in cultures.

Culture Plates Coating with Gelatin

Stock solution of 1% porcine gelatin in water, was sterilized by autoclave. Once cooled, 500 μl of the solution were added to each well of the 12-wells culture plat. After incubation for 20 min at room temperature, the excess solution was removed, and the cells were seeded.

Proliferation Medium

For the proliferation stage, cells were cultured in: DMEM/F12 (containing 1 mM $Ca^{2+}$)+10% FBS, 25 μg/mL Gentamycin, and 2 mM L-Glutamine.

Fusion Medium

For the fusion stage the Proliferation Medium was changed with Fusion Medium, which was prepared as following: DMEM/F12 (containing 1 mM $Ca^{2+}$), 2% horse serum (HS), 2 mM L-Glutamine, 25 μg/mL Gentamycin, and 4 units/100 mL Insulin (all purchased from Biological-Industries, Israel).

List of Tested Calcium Preparations

The fusion medium was enriched with the various calcium preparations listed in Table 2, at $Ca^{2+}$ concentration of 1 mM (since the medium already contained 1 mM of calcium ions, the final concentration of $Ca^{2+}$ was 2 mM). Control cultures were grown without further added calcium, or cultures enriched with free (soluble) stabilizer. The experiment was blinded by marking the various calcium preparations with arbitrary numerals only.

The components were added in one of the following ways: (i) aqueous suspensions of dry material; (ii) aqueous suspension of fresh material (before drying), or (iii) dissolved with HCl (to mimic the acidity which exists in the stomach. After dissolving was accomplished, the formed solutions were neutralized with 1M NaOH).

TABLE 2

| List of tested materials | |
|---|---|
| Added Substance | Total calcium concentration (mM) including 1 mM $Ca^{2+}$ ions of the medium |
| ACC-Etidronic Acid (ACC- ET) | 2 |
| ACC-Pyrophosphate (ACC-PyP) | 2 |
| ACC-Phospho serine (ACC-PS) | 2 |
| ACC- Adenosine triphosphate (ACC-ATP) | 2 |
| ACC- Adenosine diphosphate (ACC-ADP) | 2 |
| ACC-Phytic acid | 2 |
| ACC-Citric acid | 2 |
| Crystalline calcium carbonate (CCC) (commercially available powder) | 2 |
| $CaCl_2$ aqueous solution | 2 |
| ET | 1 |
| PyP | 1 |
| PS | 1 |
| ATP | 1 |
| ADP | 1 |
| Phytic acid | 1 |
| Citric acid | 1 |
| Control | 1 |

Results

Effect of Dry ACC on Healthy Skeletal Muscle

Figure 3:
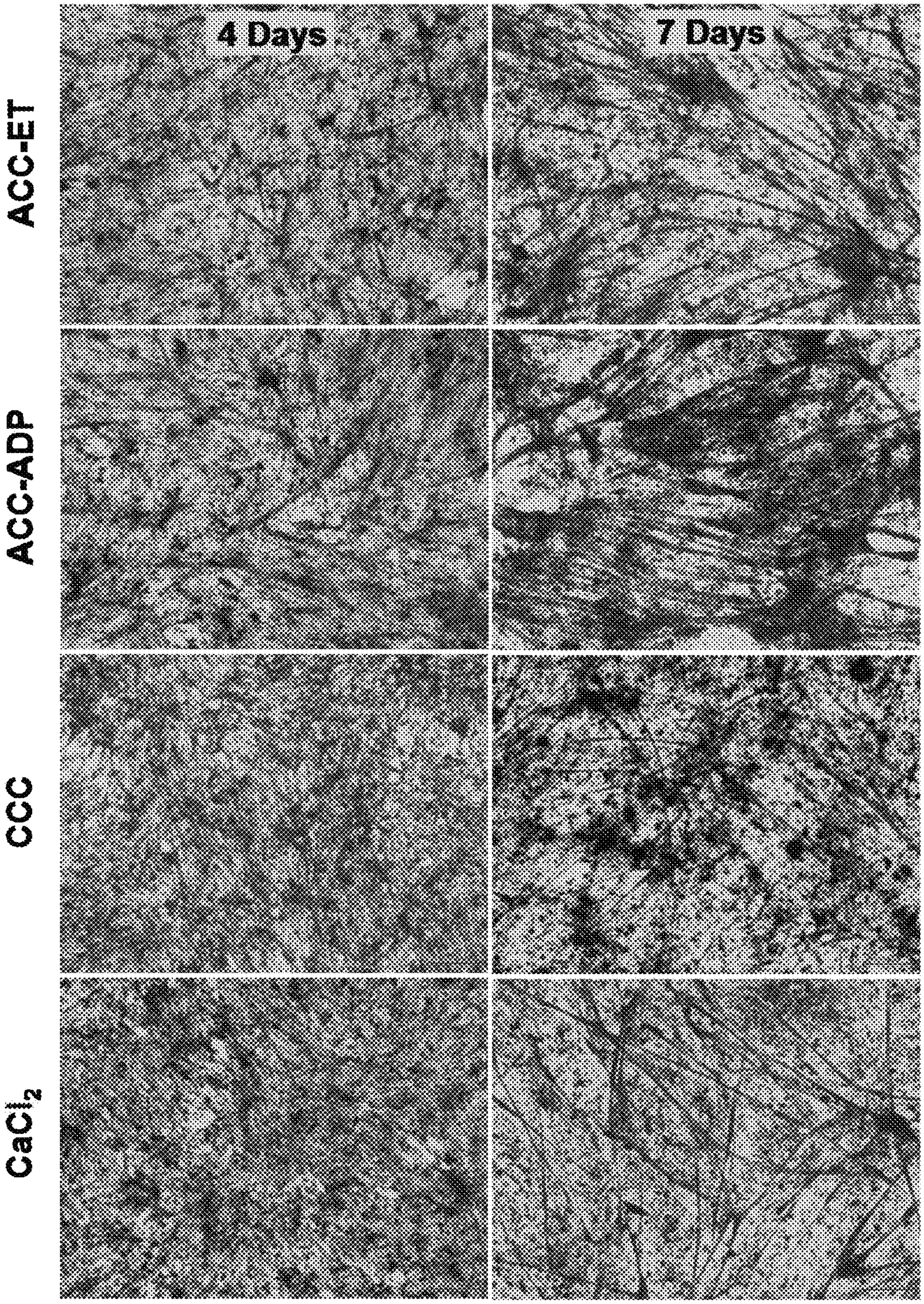
FIG. 3 shows the effect of ACC on formation of myotubes in healthy skeletal muscle cultures. Original magnification ×40. Skeletal muscle cultures were exposed to the following calcium compounds (final $Ca^{2+}$ concentration of 2 mM): ACC-Etidronic Acid; ACC-ADP; Gastrolith; crystalline calcium carbonate (CCC); and $CaCl_2$ solution (control). Cultures were fixed after 4 and 7 days and stained with Giemsa. Enhancement of myotubes formation by skeletal muscle cultures was observed in ACC treated cells.

In the first stage, dry ACC powder was used. The powder (listed in Table 2 according to the stabilizers used in their preparation) were suspended in water, and then added to the culture media in the concentration of 1 mM. Since the medium already contained 1 mM of calcium ions, then the final concentration of $Ca^{2+}$ was 2 mM. The results, some of which are shown in FIG. 3 (left hand side), revealed that cultures which were exposed to ACC exhibited early formation of many myotubes already within 4 days of cultivation, with no significant differences between the different ACC preparations. In control cultures, which were exposed to added CCC or $CaCl_2$), myotubes formation was observed later. After 7 days, the cultures that were treated with ACC exhibited numerous long and thick muscle fibers, while in cultures treated with CCC and $CaCl_2$), fewer, thinner and shorter muscle fibers were developed (FIG. 3; right hand side).

It is also noted, that in cultures exposed to ACC preparations, muscle contractions were observed already on day 7 after seeding, while in cultures exposed to added CCC or $CaCl_2$) muscle contractions appeared only after 10 days or more.

It was concluded from the above in vitro results that all ACC preparations enhance myotubes formation and early muscle contractility of the healthy striated muscle cultures.

Example 4—Evaluating the Effect of ACC on Duchenne Muscular Dystrophy Muscle Cell Line—In Vitro Studies Methods Mdx Cells Preparation The influence of the different calcium preparations was investigated on the mdx cell line (Duchenne muscular dystrophy model), which was kindly provided by Prof. (Emeritus) David Yaffe from the Weizmann Institute of Science, Israel.

Cells from the Mdx cell line were seeded in a Gelatin coated 12 wells culture plate, $3\times10^4$ cells/well containing 1 mL of Proliferation Medium. Two days later (~66% confluence), the medium was changed to Fusion Medium which was changed twice a week. The various calcium preparations were separately added to the Fusion Medium according to the treatment described in Table 3. Cultures were enriched with the various calcium preparations, at $Ca^{2+}$ concentration of 1 mM. Since the medium already contained 1 mM of calcium ions, then the final concentration of Ca2+ was of 2 mM.

TABLE 3

Calcium sources

| Treatment | Calcium source (2 mM) |
|---|---|
| Control | $CaCl_2$ |
| ACC-ET | Amorphous Calcium Carbonate-Etidronic Acid |
| ACC-PS | Amorphous Calcium Carbonate-Phospho Serine |

The effects of the tested calcium preparations on cell proliferation, fusion to form myotubes and muscle contraction were monitored by daily phase contrast microscopic observation. At predetermined days, cultures were fixed in methanol for 20 minutes and then stained with Giemsa in order to evaluate the number of myotubes formed with time in cultures.

Creatine Kinase (CK) Analysis in Muscle Tissue Culture

In muscle cell cultures, CK is an indicator of myotubes formation and CK level increases (in tissue culture plates) in direct correlation with the progression of myotubes formation in muscle cultures. At predetermined days, cells were collected from culture wells (using a rubber policeman) and kept in 1 mL PBS (without $Ca^{2+}$) at −70° C. until analyzed. For CK measurement cell samples were thawed and physically lysed using a sonicator, to release the CK from muscle myotubes. CK concentration was determined using Creatine Kinase Activity Assay Kit (CK-NAC REAGENT SET, CURTISS, CHEM-INDEX INC, Hialeah, FL, USA).

Results

Figure 4:
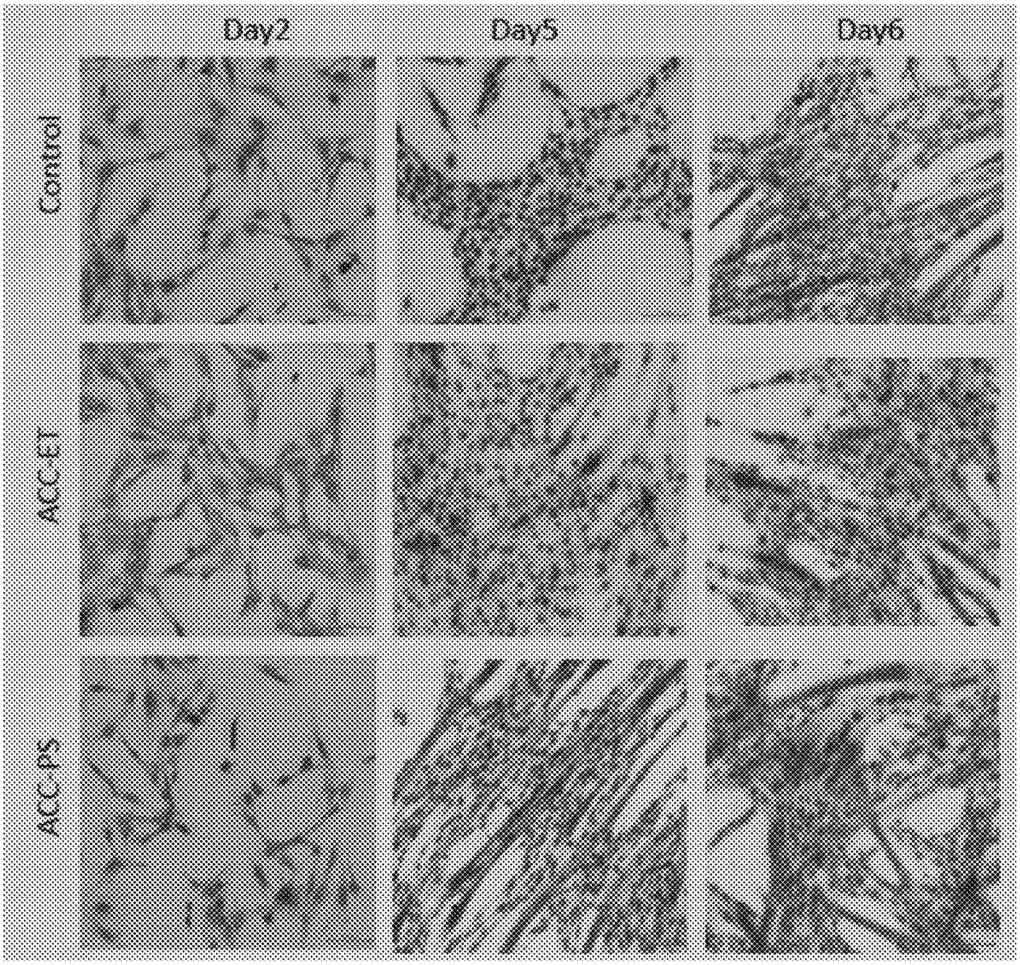
FIG. 4 shows the effect of ACC in the culture medium on early formation of myotubes in mdx cell line cultures. Giemsa staining of the cultures that were exposed to medium containing $CaCl_2$, ACC-ET and ACC-phosphoserine (ACC-PS) is shown. Original magnification ×100.
Figure 5:
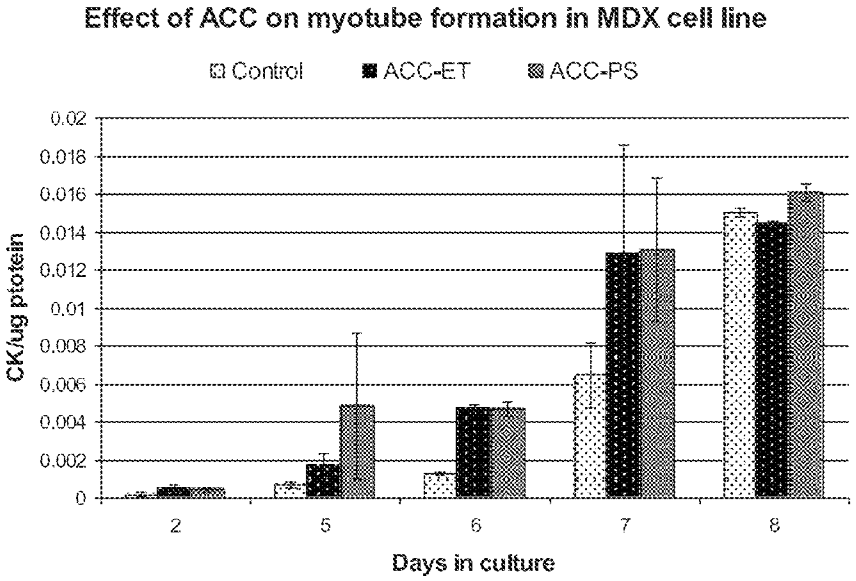
FIG. 5 shows the creatinine kinase (CK) levels as measured in mdx muscle cell line exposed to two ACC preparations (ACC-ET and ACC-PS) versus $CaCl_2$.

The results of the above experiments are presented in FIG. 4 and FIG. 5. As it can be clearly seen, addition of ACC enhanced cell fusion and formation of myotubes better than the addition of a conventional calcium ion source ($CaCl_2$)). This surprising result was demonstrated in both biochemical (CK activity) and morphological (microscopy) analysis (FIG. 4 and FIG. 5). Moreover, the cultures exposed to ACC preparations, muscle contractions were observed already on day 7 after seeding, while in the controls it appeared only after 10 days or more. Therefore, it is concluded that ACC supplementation has a potential to treat DMD patients.

Example 5—the Effect of Calcium Sources on Primary Mdx Mice Cells

Methods

Extraction of Primary Cells

Thigh muscles were removed from the posterior legs of newborn (one day old) mdx mice under sterile conditions, and washed in PBS to remove excess of blood cells. The muscles were minced into small fragments. For enzymatic dissociation, the muscle fragments were placed in a beaker containing trypsin-EDTA solution (0.25 mM). To ensure cell separation, the mixture was placed on a stirrer, at room temperature, at gentle stirring for 20 min. The soup was collected and centrifuged at 300×g for 5 min. The pellet was re-suspended in DMEM containing FBS. The trypsinization steps were repeated for 3 more cycles. All supernatants were combined into one tube. Cell separation was determined visually (using phase contrast microscopy). Cells density was determined by using hemocytometer.

Cells were plated in a 12 wells plate in the concentration of $2\times10^5$ cells/well. The medium used was DMEM/F12 W/O $Ca^{2+}$ with the addition of 15% FBS and, 2 mM L-Glutamine Gentamicin (25 μg/ml). Calcium was separately added to the medium according to the treatment as describes in Table 4. At day 2 (~66% confluence) the medium was changed to fusion medium (DMEM/F12 without $Ca^{2+}$ with the addition of 10% HS, Insulin (4 units/100 ml) and Gentamicin (25 μg/ml)). Medium was changed every 3 days.

TABLE 4

Calcium sources used in primary cells study

| Treatment | Calcium source (2 mM) |
|---|---|
| Control | $CaCl_2$ |
| ACC-PP | Amorphous Calcium Carbonate stabilized by Polyphosphate |
| ACC-PS | Amorphous Calcium Carbonate stabilized by Phosphoserine |

Cell proliferation and fusion were qualitatively daily monitored. Cultures were fixed at days 2, 3, 4, 5 and 7 and stained with Giemsa, or using Myosin antibody.

Results

Figure 6:
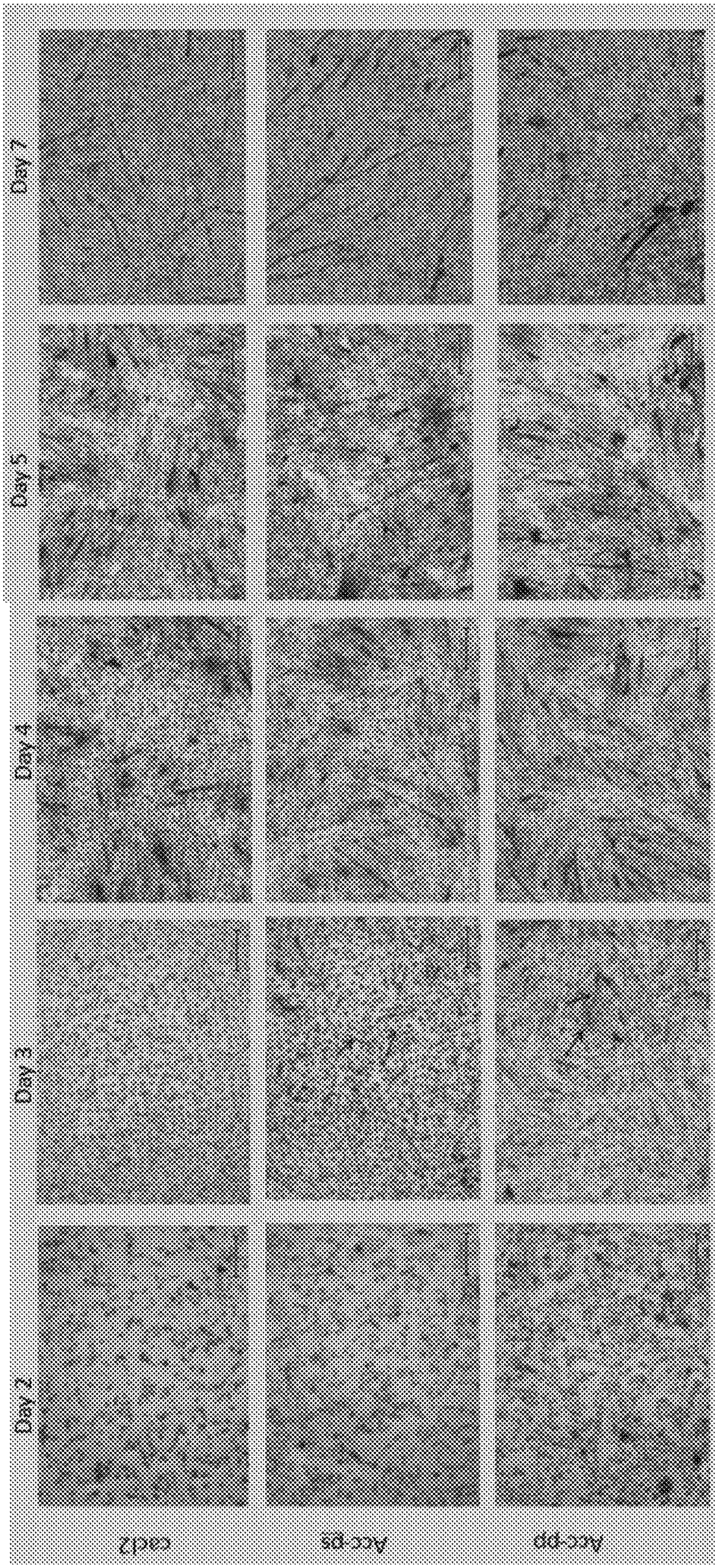
FIG. 6 shows the effect of ACC (ACC-PS, ACC-PP vs. control ($CaCl_2$)) on the formation of myotubes in mdx mice primary cultures (Giemsa staining; original magnification ×50).
Figure 7:
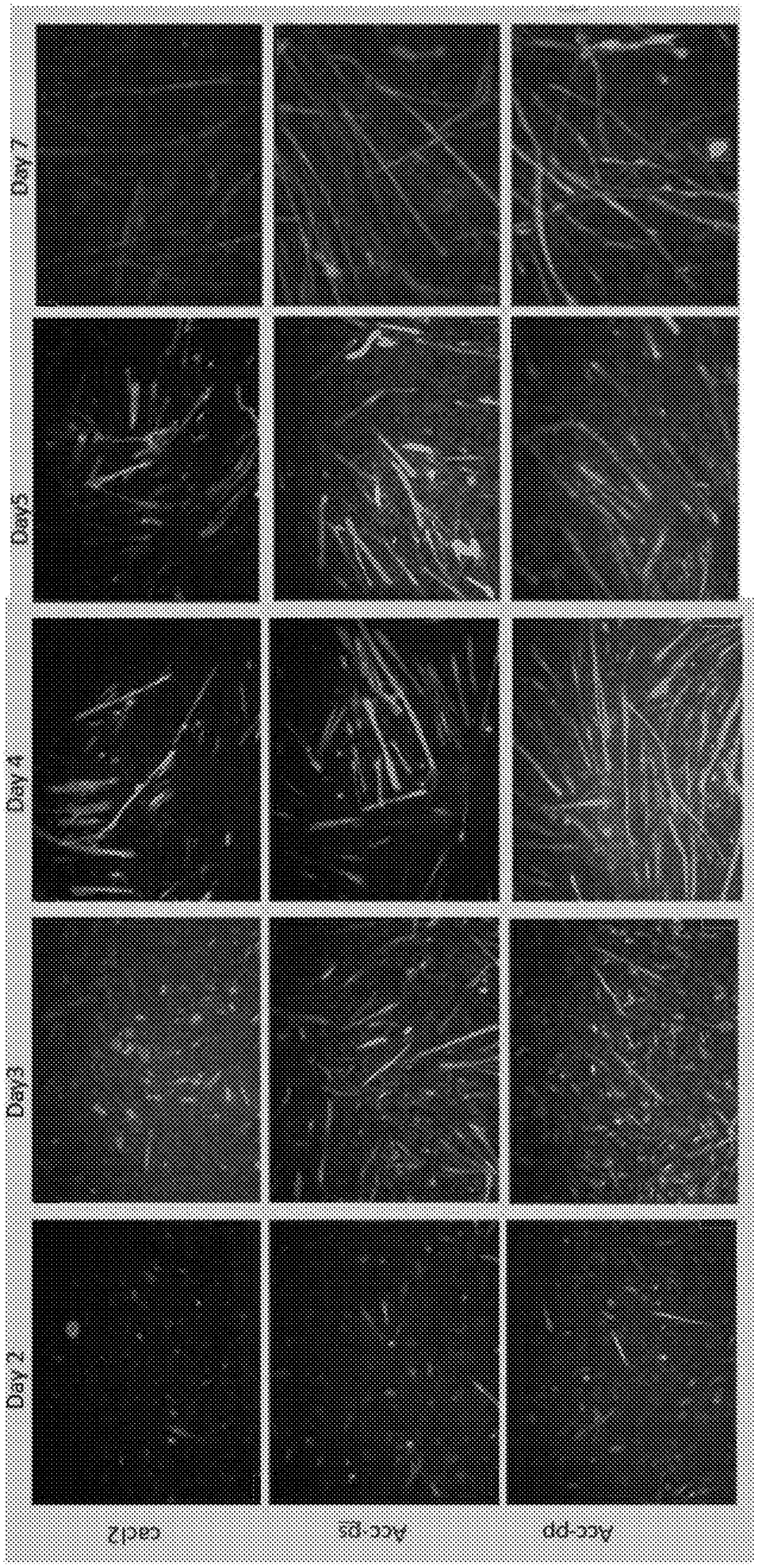
FIG. 7 shows the effect of ACC on formation of myotubes in mdx mice primary cultures demonstrated by myosin immunostaining; control ($CaCl_2$); ACC-PS, ACC-polyphosphate (ACC-PP). Original magnification ×100.

The results are presented on FIG. 6 and FIG. 7. The beneficial effect of ACC formulations was demonstrated by myotubes formation, specifically at early time points, days 3 and 4 compared to control. Differences in the formed myotubes became indistinguishable at days 5 and 7. There was a high correlation between the Giemsa staining and the staining for myosin.

Enhancement of Embryonic Development in ACC Supplemented Media

Example 6

Materials and Methods:

CBA male mice were bred with BL C57 female mice. The mice were kept on a 12 hours photoperiod schedule with unlimited water and food supply. About 6 to 8 weeks after receiving offspring, each female mouse was injected IP with 5IU of pregnant mare serum gonadotropin (PMSG).

After 48 hours each female mouse was injected IP with 5IU human chorionic gonadotropin (hCG). Male mice proven to be fertile were then put together with the superovulated females. The next morning the female mice were examined for the presence of copulatory plugs. Females that had copulatory plugs were euthanized after 24 hours (approximately 36 hours post-coitus) and embryos at 2 cell stage were retrieved from the oviducts as following: the oviducts were dissected in Quinn's Advantage™ cleavage media (SAGE, Origio, Denmark) and the embryos were transferred to 20 μL drops with Quinn's Advantage™ cleavage media (SAGE, Origio, Denmark) overlaid with mineral oil and cultured at 37.0° C. under 5% $CO_2$ and atmospheric oxygen. The collected embryos continued to grow, i.e. in-vitro culture (IVC), until blastocyst/hatching stage. To test the effect of amorphous calcium carbonate, the Quinn's Advantage™ cleavage media ("cleavage media" hereinafter) was supplemented with different additives, i.e. amorphous calcium carbonate stabilized by polyphosphate (ACC-PP), crystalline calcium carbonate (CCC), polyphosphate (PP), phosphoserine (PS) or sodium carbonate ($NaCO_3$). All supplements were added as a freshly prepared suspension; the preparation of the ACC supplements were performed under aseptic conditions. Untreated cleavage media (without addition of any additive) was used as a control (identified as Cont Q). The embryos were evaluated every day by microscope observation for a detection of the following stages: 2 cells, compactions stage, blastocysts formation and hatching stage. The fraction (in percent) of the embryos reached each stage was calculated (the number of 2 cells embryos was set as 100%).

Results

Embryos development in the cleavage media supplemented with 1.7 mM of amorphous calcium carbonate stabilized with PP (ACC-PP) was compared to a control (Cont Q—development in untreated media). The number of embryos at each developmental stage and their portion of the initial number of embryos (the latter is presented in parentheses) are presented in Table 5.

TABLE 5

Comparison between the embryos grown in the untreated cleavage media and media supplemented with ACC-PP

| | 2 Cell/d 1 | Comp/d 2 | Blast/d 3 | Hatch/d 4 |
|---|---|---|---|---|
| Cont Q | 12 | 2 (16.6) | 10 (83.3) | 8 (66.6) |
| ACC-PP | 40 | 17 (42.5) | 40 (100) | 32 (80) |

Example 7

Embryo development in the cleavage media supplemented with 1.7 mM of either ACC-PP or calcium chloride ($CaCl_2$)) was tested in two separate tests (A and B). In Test A the embryos were grown until the blastocyst stage and in Test B, until the hatching stage. The number of embryos at each developmental stage and their portion of the initial number of embryos (in parentheses) are presented in Table 6 (Test A) or Table 7 (Test B).

TABLE 6

Test A: comparison between embryos grown in cleavage media supplemented with 1.7 mM of either $CaCl_2$ or ACC-PP

| | 2 Cell/d 1 | Comp/d 2 | Blast/d 3 |
|---|---|---|---|
| $CaCl_2$ | 25 | 16 (64) | 16 (64) |
| ACC-PP | 26 | 24 (92.3) | 22 (84.6) |

TABLE 7

Test B: comparison between embryos grown in cleavage media supplemented with 1.7 mM of either $CaCl_2$ or ACC-PP

| | 2 Cell/d 1 | Comp/d 2 | Blast/d 3 | Hatch/d 4 |
|---|---|---|---|---|
| $CaCl_2$ | 27 | 20 (70) | 20 (74) | 11 (40.7) |
| ACC | 23 | 23 (100) | 23 (100) | 23 (100) |

Example 8

Embryo development in the cleavage media supplemented with 1.7 mM $CaCl_2$), 1.7 mM ACC-PP or 0.85 mM ACC-PP (half of the initial concentration of ACC-PP, identified as ACC-PP0.85). The number of embryos at each developmental stage and their portion of the initial number of embryos (in parentheses) are presented in Table 8.

TABLE 8

Comparison between embryos grown in cleavage media supplemented with 1.7 mM $CaCl_2$, 1.7 mM or 0.85 mM ACC-PP.

| | 2 Cell/d 1 | Comp/d 2 | Blast/d 3 | Hatch/d 4 |
|---|---|---|---|---|
| $CaCl_2$ | 10 | 3 (30) | 8 (80) | 3 (30) |
| ACC | 11 | 7 (63.6) | 9 (81.8) | 7 (63.6) |
| ACC-PP0.85 | 11 | 8 (72.7) | 9 (81.8) | 8 (72.7) |

Example 9

Embryos development in the cleavage media supplemented with 1.7 mM $CaCl_2$), 1.7 mM or 0.85 mM ACC-PP (ACC-PP0.85) were tested and compared to the development in the untreated media. The number of embryos at each developmental stage and their portion of the initial number of embryos (in parentheses) are presented in Table 9.

TABLE 9

Comparison between embryos grown in the untreated cleavage media and media supplemented with 1.7 mM $CaCl_2$, 1.7 mM or 0.85 mM ACC-PP.

| | 2 Cell/d 1 | Comp/d 2 | Blast/d 3 | Hatch/d 4 |
|---|---|---|---|---|
| Cont Q | 42 | 30 (71.4) | 38 (90.4) | 15 (35.7) |
| $CaCl_2$ | 30 | 16 (53.3) | 24 (80) | 13 (43.3) |
| ACC-PP | 30 | 23 (76.6) | 27 (90) | 12 (40) |
| ACC-PP0.85 | 30 | 21 (70) | 30 (100) | 24 (80) |

Example 10

In this experiment 4 female mice aged 5 months old were euthanized. The embryos from each mouse were collected as described in materials and methods, however the embryos were not pooled together. The embryos from each oviduct of each mice were either grown in the cleavage media supplemented with 1.7 mM $CaCl_2$) or 1.7 mM ACC-PP grown separately in the culture. This way we could also evaluate the differences between the mice since the embryos from each female were siblings. The number of embryos at each developmental stage and their portion of the initial number of embryos (in parentheses) are presented in Table 10.

TABLE 10

Comparison between embryos from 4 female mice grown separately in cleavage media supplemented with 1.7 mM of either $CaCl_2$ or ACC-PP.

| Mouse # | $CaCl_2$ Total embr. | ACC-PP Total embr. | $CaCl_2$ 2Cell/d1 | $CaCl_2$ irreg/d1 | ACC-PP 2Cell/d1 | ACC-PP irreg/d1 | $CaCl_2$ 8Cell/d2 | $CaCl_2$ comp/d2 | ACC-PP 8Cell/d2 | ACC-PP comp/d2 | $CaCl_2$ Blast/d3 | ACC-PP Blast/d3 | $CaCl_2$ Hatch/d4 | ACC-PP Hatch/d4 |
|---|---|---|---|---|---|---|---|---|---|---|---|---|---|---|
| 1 | 12 | 11 | 3 | 9 | 3 | 8 | 2 | 1 | 0 | 3 | 1 (8.3) | 3 (27.3) | 0 (0) | 2 (18.2) |
| 2 | 9 | 13 | 3 | 6 | 4 | 9 | 0 | 3 | 0 | 5 | 2 (22.2) | 5 (38.5) | 0 (0) | 4 (30.8) |
| 3 | 10 | 10 | 7 | 3 | 3 | 7 | 0 | 6 | 0 | 4 | 5 (50) | 4 (40) | 3 (30) | 3 (30) |
| 4 | 18 | 17 | 14 | 4 | 13 | 4 | 4 | 10 | 2 | 12 | 12 (66.7) | 14 (82.3) | 7 (41.2) | 12 (70.6) |

Example 11

In this experiment, 7 female mice aged 6 months old were euthanized. From each mouse the embryos were collected as described in materials and methods, however from mouse no. 1 and 2 the embryos were not pooled together but rather grown separately, as in Example 5. The embryos from mouse no. 1 were either grown in untreated cleavage media or medium supplemented with 2.6 mM ACC-PP (ACC-PP2.6). The embryos from mouse no. 2 were grown in the cleavage media supplemented with 1.3 mM or 0.6 mM of ACC-PP (identified as ACC-PP 1.3 and ACC-PP0.6, respectively). Embryos from mice no. 3-7 all were pooled together and grown with 1.6 mM of polyphosphate (PP). In addition, the diameters and volumes of the blastocysts were calculated. The number of embryos at each developmental stage and their portion of the initial number of embryos (in parentheses) are presented in Table 11.

TABLE 11

Comparison between sibling embryos grown in untreated cleavage media or media supplemented with ACC-PP at different concentrations. The pooled embryos from mice No. 3-7 were grown in the media supplemented with polyphosphate.

| | Mouse 1 | | Mouse 2 | | |
|---|---|---|---|---|---|
| Additive | Cont Q | ACC-PP2.6 | ACC-PP1.3 | ACC-PP0.6 | Mice 3-7 PP |
| Total # | 17 | 19 | 18 | 13 | 37 |
| 8 cell/d 2 | 7 | 3 | 7 | 4 | 9 |
| comp/d 2 | 10 | 16 | 11 | 8 | 20 |
| Blast/d 3 | 17 (100) | 19 (100) | 18 (100) | 13 (100) | 20 (54.1) |
| Hatch/d 4 | 11 (64.7) | 19 (100) | 17 (94.4) | 6 (46.2) | 17 (45.9) |

It was found that the hatched blastocysts that were grown with 2.6 mM of ACC-PP had 28% bigger diameter and 2 times bigger volume than the control.

Example 12

In this experiment, 7 female mice aged 6 months old were euthanized. The embryos from each mouse were collected as described in materials and methods (Example 6). The embryos were pooled together and divided into 5 groups that were grown in the untreated cleavage medium (Cont Q), or in the medium supplemented with 2.6 mM, 1.3 mM, 0.6 mM ACC-PP (identified as ACC-PP2.6, ACC-PP1.3 and ACC-PP0.6, respectively), or 1.6 mM of polyphosphate (PP). The number of embryos at each developmental stage and their portion of the initial number of embryos (in parentheses) are presented in Table 12.

TABLE 12

Comparison between the embryos grown in the untreated cleavage media or media supplemented with 2.6 mM, 1.3 mM or 0.6 mM ACC-PP or with 1.6 mM PP.

| | Cont Q | ACC-PP2.6 | ACC-PP1.3 | ACC-PP0.6 | PP |
|---|---|---|---|---|---|
| Total # | 42 | 20 | 31 | 21 | 36 |
| 8 cell/d 2 | 19 | 5 | 7 | 5 | 6 |
| comp/d 2 | 25 | 15 | 24 | 16 | 30 |
| Blast/d 3 | 35 (83.33) | 20 (100) | 26 (83.87) | 3 (14.28) | 34 (94.44) |
| Hatch/d 4 | 16 (38.09) | 19 (95) | 15 (48.38) | 18 (85.7) | 16 (44.44) |

Example 13

In this experiment, 6 female mice aged 6 months old were euthanized. The embryos from each mouse were collected as described in materials and methods. The embryos were pooled together and were divided into 3 groups: one served as control (Cont Q), and in two other groups the embryos were grown in the cleavage media supplemented with 3.3 mM of ACC-PP (ACC-PP3.3) or with 3.3 mM of commercially available nanometric crystalline calcium carbonate (CCC). All the three media were prepared under aseptic conditions. The number of embryos at each developmental stage and their portion of the initial number of embryos (in parentheses) are presented in Table 13.

TABLE 13

Comparison between the embryos grown in the untreated cleavage media or media supplemented 3.3 mM ACC-PP or 3.3 mM CCC.

| | Cont Q | ACC-PP 3.3 | CCC |
|---|---|---|---|
| Total # | 18 | 45 | 17 |
| 8 cell/d 2 | 10 | 0 | 3 |
| comp/d 2 | 8 | 45 | 14 |
| Blast/d 3 | 18 (100) | 45 (100) | 17 (100) |
| Hatch/d 4 | 14 (77.7) | 42 (93.3) | 14 (82.35) |

Example 14

In this experiment, 6 female mice aged 7 months old were euthanized. From each mouse the embryos were collected as described in materials and methods (Example 6). The embryos were pooled together and were grown in the cleavage media supplemented with 1.7 mM $CaCl_2$), 1.7 mM ACC-PP, 0.8 mM of ACC-PP (ACC-PP0.8) or 1.7 mM of phosphoserine (PS). The number of embryos at each developmental stage and their portion of the initial number of embryos (in parentheses) are presented in Table 14.

TABLE 14

Comparison between the embryos grown in the cleavage medium supplemented with 1.7 mM $CaCl_2$, 1.7 mM, 0.8 mM ACC-PP or 1.7 mM of PS.

| | $CaCl_2$ | ACC-PP | ACC-PP 0.8 | PS |
|---|---|---|---|---|
| Total # | 11 | 15 | 14 | 13 |
| 8 cell/d 2 | 6 | 1 | 3 | 5 |
| comp/d 2 | 5 | 14 | 11 | 8 |
| Blast/d 3 | 10 (90.90) | 14 (93.3) | 14 (100) | 12 (92.3) |
| Hatch/d 4 | 4 (36.36) | 13 (86.6) | 11 (78.57) | 10 (76.9) |

It can be seen that in that particular experiment adding calcium chloride had a negative effect on embryonic development resulting in a lower percentages of blastocysts and hatched blastocysts.

Example 15

In this experiment 6 female mice aged 6 months old were euthanized. The embryos from each mouse were collected as described in materials and methods (Example 6), however the embryos from mouse no. 1 and 2 were not pooled together but rather grown separately as a sibling experiment (see Example 10). The embryos from female no. 1 were grown in the untreated cleavage media or in the media supplemented with 1.7 mM nanometric crystalline calcium carbonate (CCC). The embryos from mouse no. 2 were grown in the media supplemented with 1.7 mM ACC-PP or with 1.7 mM of sodium carbonate ($NaCO_3$). All the embryos from mice no. 3-6 were pooled together and grown in the untreated media or media supplemented with 1.7 mM $NaCO_3$ or 1.7 mM ACC-PP. In addition, the diameter and volume of the blastocysts were calculated (see Table 15).

TABLE 15

A development assessment of sibling embryos taken from two mice and of pooled embryos grown in differently supplemented cleavage media.

| | Mouse 1 | | Mouse 2 | | Mice 3-6 | | |
|---|---|---|---|---|---|---|---|
| Additive | Cont Q | CCC | ACC-PP | $NaCO_3$ | Cont Q | $NaCO_3$ | ACC-PP |
| Total # | 20 | 24 | 12 | 16 | 20 | 10 | 19 |
| 8 cell/d2 | 14 | 14 | 3 | 6 | 14 | 2 | 17 |
| comp/d2 | 6 | 6 | 8 | 8 | 6 | 7 | 8 |
| degenerative | 0 | 1 | 1 | 2 | 0 | 1 | 0 |
| early Blast/d3 | 11 | 8 | 2 | 14 | 12 | 0 | 2 |
| Blast/d3 | 9 | 12 | 9 | 2 | 8 | 0 | 17 |
| Blast/d4 | 6 | 5 | 0 | 0 | 6 | 0 | 0 |
| Hatch/d4 | 14 (70) | 15 (62.5) | 11 (91.6) | 2 (12.5) | 14 (70) | 0 (0) | 19 (100) |

It can be seen that adding sodium carbonate resulted with very poor embryonic development compared to control or to the addition of ACC-PP. It was also found that the hatched embryos that were grown in the cleavage media supplemented with 2.6 mM of ACC-PP had a 28% bigger diameter and ×2 times a bigger volume than the control.

Example 16. Preparation of 10% TP-1% Citric Acid ACC (ACC Stabilized with 10% Triphosphate and 1% Citric Acid) Formulated as Cell Culture Medium Supplement 36 ml of 3% Calcium chloride solution were mixed with 4 ml of 0.27% Citric Acid solution and with 10 ml of 0.5406% Triphosphate solution. Then 40 ml of 1.9485% Sodium carbonate solution was added to precipitate ACC. 10 ml of the stabilizing solution containing 0.5406% triphosphate was added to the ACC suspension creating stabilized ACC suspension. The obtained suspension was used as a supplement to Quinn's™ cleavage medium or to Quinn's™ 1-Step medium. The suspension was added to the final concentration of ACC of 1.7 or 3.4 mM. Alternatively, the suspension is filtered using a Buchner funnel, the cake is washed with water and the cake is further dried, e.g. in the oven. The powder is added to the cleavage medium to the final concentration of 1.7 or 3.4 mM.

Example 17

Figure 8:
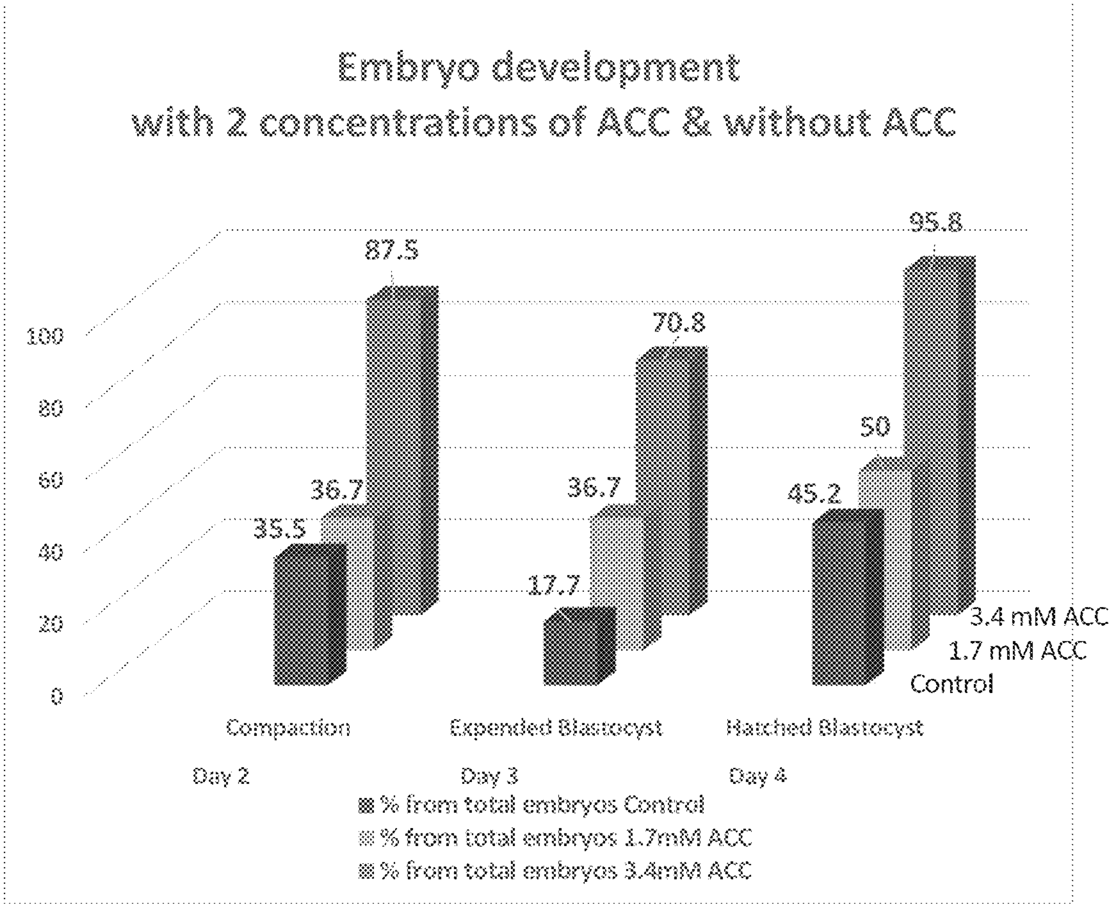
FIG. 8 shows the effect of stabilized ACC on mice embryos development in vitro.

In this experiment 4 female mice aged 6-8 weeks old were euthanized. The embryos from each mouse were collected as described in materials and methods. The stabilized ACC (ACC stabilized with 10% triphosphate and 1% citric acid) was prepared as described in Example 16. The embryos from each female were separated and were grown one part in the untreated SAGE 1-Step™ medium and the second part in the SAGE 1-Step™ medium supplemented with 1.7 mM ACC-PP or 3.4 mM ACC-PP. As can be seen from FIG. 8 addition of stabilized ACC had a positive effect on the embryonic development resulting in a higher percentage of blastocysts and hatched blastocysts especially with the 3.4 mM ACC. It has been surprisingly found that embryos that were grown in cleavage medium supplemented with stabilized ACC showed a rapid cleavage and higher hatching rate.

Example 18. Preparation of ACC Formulated as Cell Culture Medium Supplement

Compositions of ACC stabilized by different stabilizers (triphosphate (TP), hexametaphosphate (HMP), pyrophosphate (Pyr), phosphoserine (PS), Etidronic acid (ET), Zoledronic acid (ZA); or Medronic acid (MA) were prepared)

were prepared. In a typical procedure, a calcium solutions (300 ml of water, 24 g of calcium chloride and a stabilizer) and a carbonate solution (200 ml of water and 17.3 g of sodium carbonate) were mixed together to precipitate ACC. A stabilizer solution (100 ml of water and stabilizer; the content of the stabilizers in the calcium and stabilizer solution is presented in Table 16) was added to the ACC suspension creating stabilized ACC suspension. The suspension may be used as a supplement. The ACC was then filtered using a Buchner funnel, and the cake was washed with water. The suspension was dried to obtain a powder. The powder may be added as a cell culture medium supplement or resuspended in an aqueous medium and added as a suspension.

calcium). Row H of the plate was treated with MSC NutriStem® XF nutrient basal medium+supplement mix (total 1.488 mM calcium).

On day 4, medium was exchanged with fresh preparations of ACC.

In parallel, a control plate was also seeded with MDX cell lines originated from damaged muscles of MDX mice. The staining of these cell was used to set the background staining of cells intrinsic calcium and to eliminate the possibility that calcium deposition of the ACC treatment is stained. Prior seeding, wells were coated with gelatin, which is used as a standard substrate for MDX cells attachment. MDX Cells were seeded on a 24 well plate in a concentration of $3\times10^4$ cells/well. Seeding day is defined as "Day 0".

TABLE 16

The content of the stabilizers in different ACC composition

| Stabilizer in: | Composition | | | | | | | |
|---|---|---|---|---|---|---|---|---|
| | 1% TP | 2% TP/ HMP/Pyr | 3% TP/ HMP/Pyr | 4% TP/ HMP/Pyr | 5% TP/ HMP/Pyr/ PS/ET/ ZA/MA | 6% TP/ HMP/Pyr/ PS/ | 10% TP/ HMP/Pyr/ PS/ET/ ZA/MA | 15% TP/ HMP/Pyr/ PS |
| Calcium solution (g) | 0.12 | 0.24 | 0.36 | 0.48 | 0.6 | 0.72 | 1.2 | 1.8 |
| Stabilizing solution (g) | 0.12 | 0.24 | 0.36 | 0.48 | 0.6 | 0.72 | 1.2 | 1.8 |

In other examples the compositions were prepared as described above, with addition of citric acid to calcium solutions so as to obtain 1% citric acid in the final composition. The suspension is used per se as a culture medium supplement. Alternatively, the suspension was further washed with water and dried so as to obtain a powder. The powder may be added to any cell culture medium or be resuspended in aqueous medium.

Example 19. Growth of MBA13 Stem Cells (Bone Marrow Stromal Cells) to Osteoblasts Material and Methods Two days following thawing, MBA-13 cells (received from Prof. Dov Zipori, Weizmann Institute of Science) were re-suspended in recombinant trypsin solution and seeded on a 96 wells plate, (Day "0") in a concentration of $1\times10^4$ cells/well using MSC Nutristem® XF basal medium (Biological Industries, cat #05-200-1A) supplemented with Mesenchymal stem cells (MSC) supplement mix medium (Biological Industries cat #05-201-06) in a ratio of 50 ml:300 µl. Rows A-H of columns 1-4 of the 96 plate were pre-coated with MCS attachment solution diluted in PBS (without $Ca^{2+}$, $Mg^{2+}$), in a ratio of 1:100 for cells seeding. Rows A-H of Columns 5-8 of the 96 plate were pre-coated with Gelatin 0.1% for 30 minutes at room temperature.

On day 2, when more than 80% cell confluence was achieved (~48 h) the medium was changed to MSCgo™ rapid osteogenic medium (cat #05-442-1B) containing factors that promote osteoblastic differentiation. Following medium change, rows A-C were supplemented with additional 1 mM calcium (total 2.488 mM calcium) originated from Amorphous Calcium Carbonate (ACC) stabilized by 10% Triphosphate+1% citric acid; rows D-F were supplemented with additional 1 mM calcium (total 2.488 mM calcium) originated from calcium chloride; Row G in the plate was treated with MSCgo™ medium (total 1.488 mM On day 2, the medium in the wells was replaced with the following:

Columns 1 and 2 were treated with Spinal Cord (SC) medium that is prepared in-house (the medium comprises 0.6 wt % D-glucose, 2 mM L-glutamine, Gentamicin 25 µg/ml, B27, $N_2$, BSA 0.1 mg/ml, Hepes, 10% FBS, DMEM/F12 and IGF-I, 50 ng/ml)+1 mM calcium originated from ACC (total calcium concentration of 2 mM); columns 3 and 4 were treated with SC medium+1 mM calcium originated from $CaCl_2$); Columns 5 and 6 were treated with SC medium. Both types of cells (MBA13 and MDX) were cultured up to 10 days.

Fixation (with 4% Paraformaldehyde for 20 minutes) of few wells from each type was performed on the 5th, 7th and 10th day following medium exchange, that are Days 7, 9 and 12 of the study.

Once the cells were fixated, two types of staining reagents were used to stain extracellular calcium or bone deposition in order to estimate osteoblasts functionality: (i) Alizarin red (Sigma A55333) and (ii) Alkaline Phosphatase (DAKO BCIP/NBT substrate system K0598) as following:

Alizarin red staining procedure—pH was adjusted to 4.2. Cells were washed twice with PBS and fixed with cold methanol for 5 minutes and then washed again with PBS. Alizarin solution in a concentration of 2% was used for 15-20 minutes. Following staining incubation, the samples were washed with water 2-3 times to remove unspecific staining.

Alkaline Phosphatase staining—cells were washed 1 or 2 times with PBS and then fixed with 4% paraformaldehyde for 20 min. Then, washed 3 times with PBS and following removal of PBS remnants, 3 drops of BCIP/NBT kit solution were used to cover the cells including one empty well without any cells as control to quantify the assay. Incubation of the Alkaline phosphatase kit was performed for 1 hour and then rinsed with distilled water.

Results

The results of cells that were cultured for 10 days and stained by both Alizarin and Alkaline phosphatase are provided. Observation performed prior to 10 days hardly detected any calcium deposition in both staining methods.

Cells condition was observed under a light microscope (without fixation) at two time points, days 2 and 4. On both observations, cells that were seeded on wells pre-coated with MSC attachment solution were not in a good condition; the cells became rounded. In contrast, cells that were seeded on wells pre-coated with gelatin were in a good condition. Nevertheless, it was decided to continue with both types of pre-coating. The following results and staining procedures refer to cells grown in Gelatin that was used as attachment substrate.

In Alizarin Red staining, calcium deposits are detected by an orange red color.

Figure 9A:
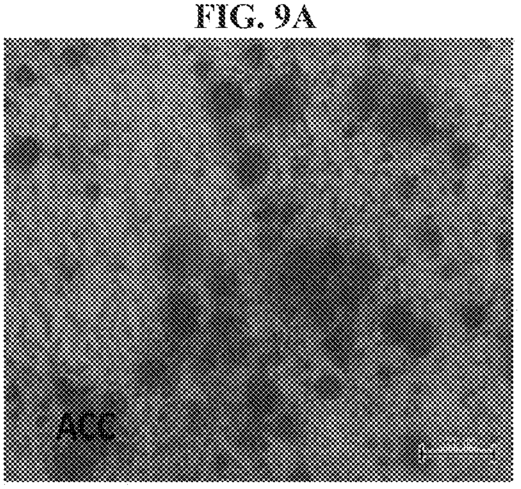
Figure 9B:
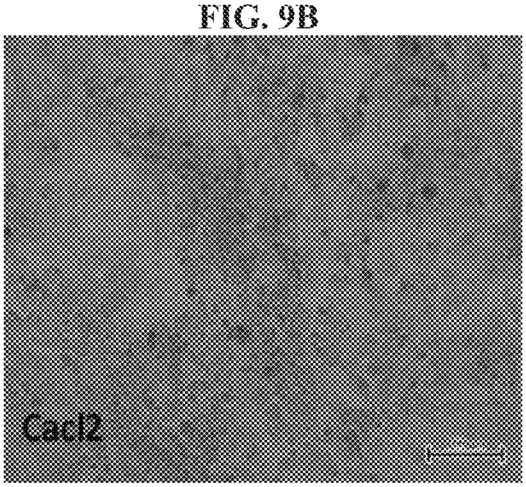
Figure 9C:
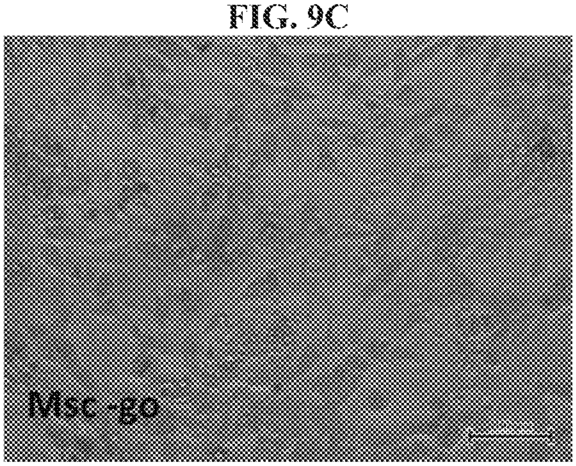

Alizarin Red staining demonstrated a very strong signal in osteoblast cell samples that were supplemented with ACC compared to those supplemented with $CaCl_2$), which demonstrated a weak signal only, (FIG. 9). In addition to the signal, it can be seen in the figure that large plaques of calcium deposition are stained which are not observed in any of the controls treatments.

The Alizarin Red staining of cells grown in MSCgo™ rapid medium also demonstrated some staining of calcium deposition but the size of the deposition and its amount is significantly lower, and resembles the morphology and amount observed for cells supplemented within $CaCl_2$. Calcium deposition was not seen at cells grown in MSC NutriStem+ supplements (MSC sup; data not shown). MSC NutriStem+sup medium is normally used to induce cells proliferation rather than differentiation. Indeed the number of cells observed is large but no calcium deposition is observed.

This observation suggests that ACC treatment enhances MBA13 cells differentiation into osteoblasts and raises the cells calcium deposition, i.e. enhances their functionality.

Another independent marker for osteoblast differentiation is the alkaline phosphatase. This enzyme is expressed maximally when the matrix maturation phase of cells occurs. Alkaline phosphatase staining was used as a complementary method to detect osteoblasts differentiation and functionality so as to verify the result obtained by the Alizarin staining.

Figure 10A:
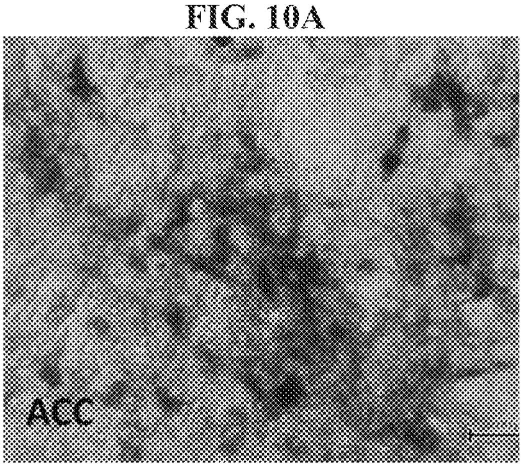
Figure 10B:
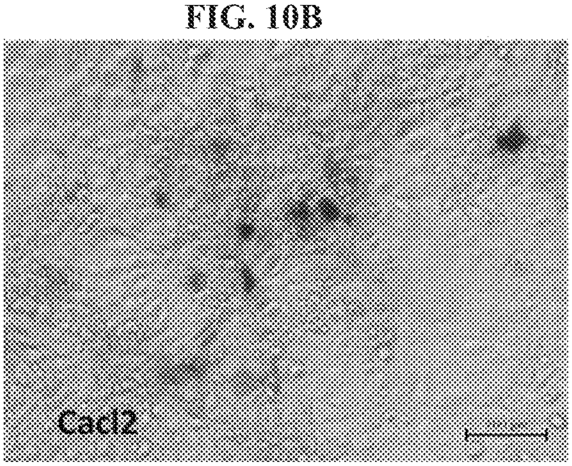
Figure 10C:
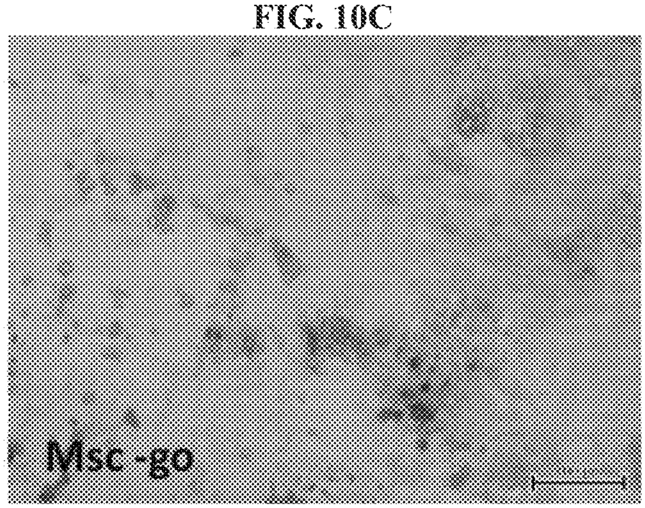

The alkaline phosphatase staining is shown in black color and the results are presented on FIG. 10. MBA13 cells that were treated with ACC demonstrated an intense signal in comparison to the other treatments. Indeed, Alkaline phosphatase staining support that osteoblasts differentiation is better in cultures treated with ACC.

Figure 11A:
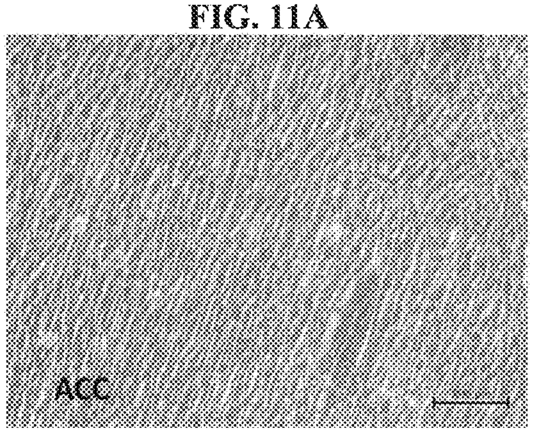
FIG. 11A-FIG. 11C show Alizarin red staining and FIG. 11D-FIG. 11F show Alkaline phosphatase staining of mdx cell lines grown in media with different sources of additional 1 mM $Ca^{2+}$ added.
Figure 11B:
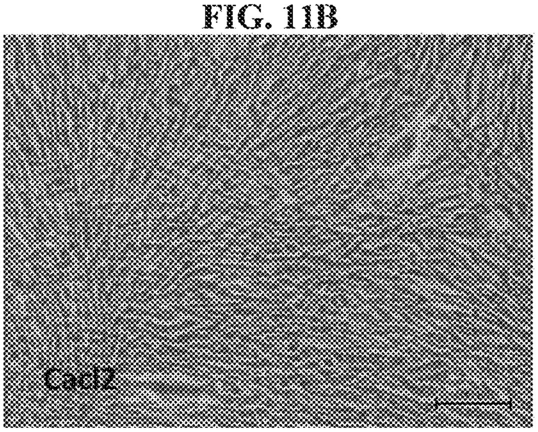
Figure 11C:
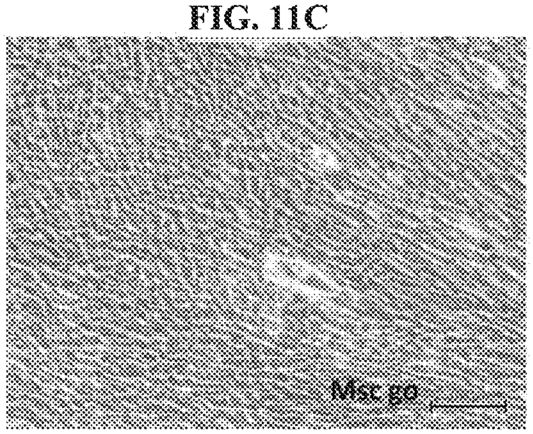

Alizarin staining of MDX cells treated with ACC enriched medium 10 days following seeding demonstrated no major differences in the staining among the treatments (see FIG. 11A-FIG. 11C). These results support that Alizarin Red staining of osteoblasts is due to calcium deposition by the osteoblast and not due to ACC deposition caused by the treatment itself (i.e. it is not an experimental artifact).

Figure 11D:
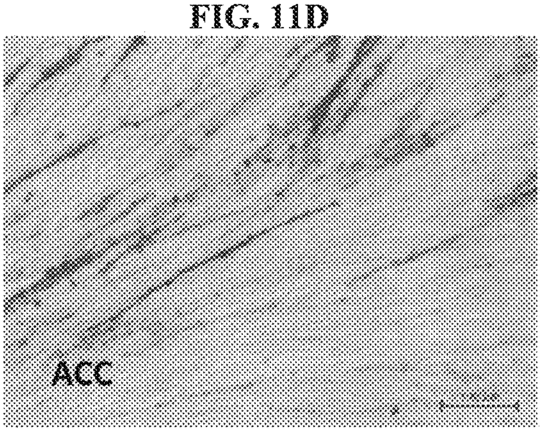
Figure 11E:
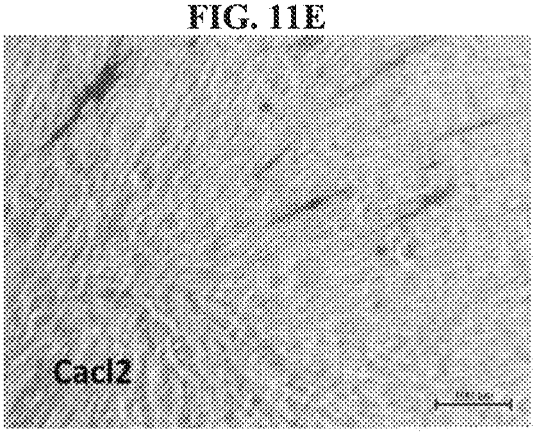
Figure 11F:
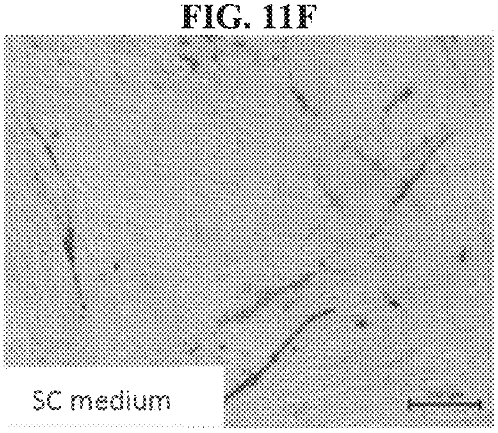

The staining of Alkaline phosphatase of MDX cell lines (FIG. 11D-FIG. 11E) demonstrated that there was no bone formation occurred. Interestingly, in Alkaline phosphatase stain enhanced myotubes formation was observed in ACC treated cells in comparison to cells grown in $CaCl_2$) supplemented medium or control.

Conclusions

Both independent staining, Alizarin Red and Alkaline phosphatase following the 10 days of seeding at different medium showed substantial stronger staining of the osteoblast cells deposition that were grown in medium supplemented with ACC in comparison to the controls used.

While large calcium deposition plaques were observed when cells grown in the presence of ACC, such deposition was not observed for cells grown in medium supplemented with $CaC_{l2}$. Stronger signal might indicate on a larger functionality, since the staining demonstrated more plaque deposition. The result obtained by the MDX cells staining suggests that the plaques are not originated from the ACC addition but are a direct result of the osteoblast functionally.

Example 20—ACC for Enhancement Sperm Motility

Materials and Methods

ACC Suspension Preparation 36 ml of 3% Calcium chloride solution was mixed with 4 ml of 0.3% Citric Acid solution and with 10 ml of 0.5% Triphosphate solution. Then 40 ml of 2% Sodium carbonate solution was added to precipitate ACC. 10 ml of the stabilizing solution containing 0.5% triphosphate was added to the ACC suspension creating stabilized ACC suspension. The elemental calcium concentration of the obtained suspension was 75 mM.

Sperm Collection

Sperm were collected 3 times from the same ram (exp. 1) or twice from 3 rams (exp. 2 & 3) and evaluated to concentration and motility at room temperature. The sperm was diluted to concentration of 50 million sperm/ml in Synthetic Oviduct fluid (SOF) comprising: 107.70 mM NaCl, 7.16 mM KCl, 1.19 mM KH2PO4, 1.71 mM CaCl2, 0.49 mM MgCl2, 25.07 mM $NaHCO_3$, 3.30 mM Na lactate, and 1.50 mM glucose (10) in Milli-Q water. The osmolarity should be 270 mOsmol and the pH 7.55.

Sperm was then evaluated for motility using CASA (Theriogenology, 2014, Volume 81, Issue 1, Pages 5-17) and cooled to 4° C. at 1° C./min.

Swim Up Procedure

Swim up procedure was performed at 38° C., the raw sperm (10 ul) was placed in eppendorf 1 ml vial and incubated for about 1 hour in SOF medium which was inserted in 0.25 ml straws (CBS, France). After 40-60 minutes the sperm which entered the straw were placed on a slide and evaluated by CASA.

Results

The motility of the freshly collected sperm was tested as described in materials and methods section with or without addition of amorphous calcium carbonate. The results are presented in Table 17.

TABLE 17

The motility assessment of sperm with and without the addition of ACC suspension 34 μl/ml (2.6 mM of elemental Ca).

| | % motility | % progressive motility |
|---|---|---|
| Control | 96 ± 1.15 | 55.3 ± 1.15 |
| ACC (34 μl/ml: 2.6 mM elemental Ca) | 95 ± 1 | 70.6 ± 3.2 |

It can be seen that sperm supplemented with ACC had much higher progressive motility than untreated sperm.

Example 21. Effect of ACC on Sperm Motility in a Swim Up Experiment

To evaluate the effect of ACC on sperm motility, a standard swim up experiment was performed in the presence of 17 μl/ml and 34 μl/ml of ACC suspension (1.3 and 2.6 mM of elemental Ca, respectively). The viable spermatozoa was counted after one hour and the results are summarized in Table 18.

TABLE 18

Effect of ACC on sperm motility in a swim up experiment (concentration in million/ml)

| ACC concentration (elemental calcium concentration) | Sperm concentration ($\times 10^6$/ml) exp 1 | exp 2 | exp 3 |
|---|---|---|---|
| control | 142 ± 7.3 | 97 ± 15 | 207 ± 12 |
| ACC 17 μl/ml (1.3 mM elemental Ca) | 523 ± 5.7 | 186 ± 14 | |
| ACC 34 μl/ml 1.3 mM elemental Ca) | | | 1463 ± 400 |

It can be clearly seen that addition of ACC significantly increased the number of viable spermatozoa in all experiments. In the samples supplemented with ACC, the number of viable spermatozoa was between 2 to 7 times higher than in the untreated samples.

Example 22. Effect of ACC Concentration on Sperm Motility in Swim-Up Experiment The effect of ACC concentration of the motility of sperm was tested by a swim-up experiment using 3 different samples for each ACC concentrations. The results are summarized in Table 19.

TABLE 19

Effect of ACC concentration on sperm motility in swim up experiment (concentration in million/ml)

| ACC concentration (elemental calcium concentration) | Sperm concentration ($\times 10^6$) |
|---|---|
| Control | 45.5 |
| ACC 8 μl/ml (0.6 mM elemental Ca) | 102, 77, 89 |
| ACC 17 μl/ml (1.3 mM elemental Ca) | 179, 170, 174 |
| ACC 34 μl/ml(2.6 mM elemental Ca) | 196, 200, 198 |
| ACC 60 μl/ml (4.6 mM elemental Ca)) | 182, 205, 193 |

It has been noted that the addition of 17 μl/ml ACC suspension to the synthetic oviduct fluid (SOF) solution and incubation at 38 C for 1 hour increased the concentration of motile sperm by at least 3 folds. Interestingly, higher concentration of ACC did not reduce the concentration of motile sperm after swim-up. It was concluded that ACC enhanced the concentration of sperm after swim-up procedure and did not have any bi-phasic effect for ionic calcium. Any ACC concentration above the minimum effective dose increases motility.

Example 23. ACC Preserves Ovaries In Vitro

Material and Methods

Ovaries were collected from mice (6 weeks old) cut to 0.4 mm×0.4 mm pieces. The ovaries were culture in 12 well plates. The culture medium was composed of: 90% Dulbecco's modified eagle medium-nutrient mixture F-12(DMEM-F12) calcium depleted (medium without calcium ions, special preparation), 10% fetal bovine serum (FBS), 2 mM glutamine, 25 μg/mL gentamicin and 0.3-0.5% NVR-Gel with or without stabilized 3.4 mM ACC-PP. After 48 h of culturing, 51U of pregnant mare's serum gonadotrophin (PMSG) were added into the culture dish.

Results

Figure 12A:
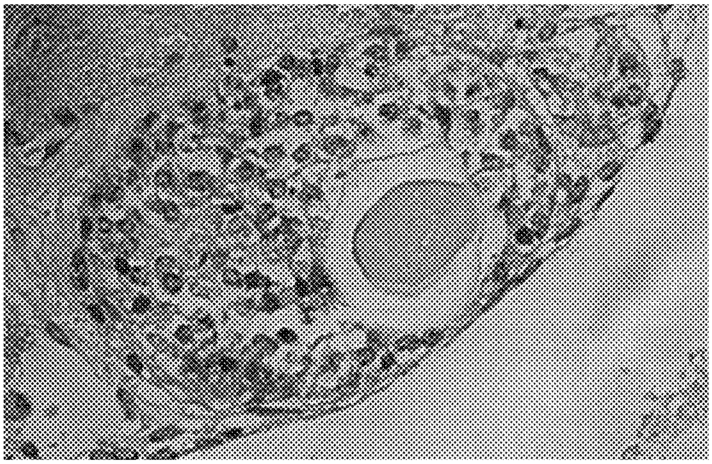
FIG. 12A and FIG. 12B show effect of stabilized ACC of in vitro cultured ovaries (FIG. 12A) in which granulosa cells surrounding the oocytes were intact versus control (FIG. 12B) (no ACC in the medium) in which non intact granulosa cells and oocyte at the Germinal Vesicles stage was observed.
Figure 12B:
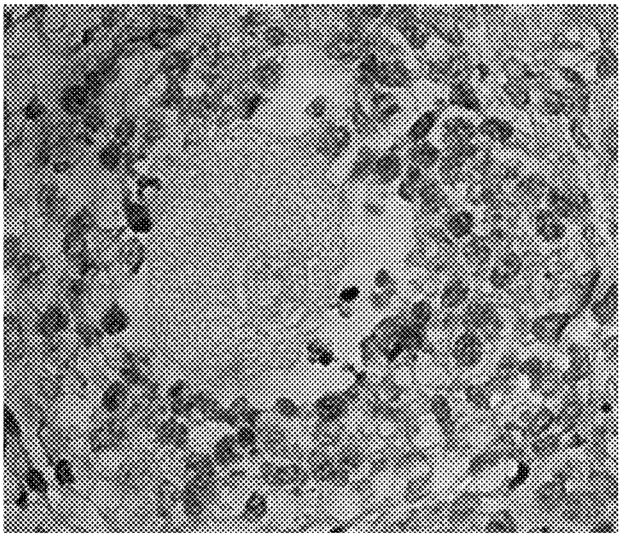

It can be seen on FIG. 12, that secondary follicles were developed after 2 weeks of in vitro culturing in the presence of stabilized ACC, and granulosa cells surrounding the oocytes were intact. On the contrary, secondary follicles in the control group show non-intact granulosa cells and Germinal vesicles oocyte. Much more follicles were observed in the ACC group, implying that addition of the ACC in the culture medium allows faster and better growth of follicles and improved preservation of ovaries.

Example 24. Effects of ACC on Mouse BM-MSC Functionality and Differentiation to Osteoblasts on Earth and in Space Materials and Methods MBA-13 cells (kindly provided by Prof. Dov Zipori, Weizmann Institute of Science) were seeded in a fibronectin pre-coated 12-well plate. Two days following seeding, the cells were detached from the wells with a recombinant trypsin solution (Sartorius, catalog #03-078-1B, BI) and seeded in a fibronectin pre-coated 96-well plate, (Day "0") at a density of $1\times10^4$ cells/well, using MSC NutriStem® XF basal medium (Sartorius cat #05-200-1) and MSC supplement mix medium (Sartorius cat #05-201-06) at a ratio of 50 ml:300 μl (hereafter referred to as MSC NutriStem® complete medium).

On day 2, when more than 80% cell confluence was reached (~48 h) the medium was changed to MSCgo™ rapid osteogenic medium (Sartorius cat #05-442-1B) to promote osteoblast differentiation. Following the medium change, the first three rows in the 96-well plate (rows A-C) were treated with an additional 1 mM calcium (total calcium concentration 2.5 mM) originating from ACC. The cells in the second series of three rows on the plate (D-F) were treated with an additional 1 mM calcium (total 2.5 mM calcium) originated from $CaCl_2$). Cells in row G on the plate were treated with MSCgo™ medium (total 1.5 mM calcium) and cells in row H were treated with MSC NutriStem® complete proliferation medium with ACC as negative control.

On day 4, medium was exchanged with a freshly prepared ACC.

To eliminate the possibility that the staining was derived from calcium deposition of the ACC treatment, a control plate was also seeded in parallel with undifferentiated myoblasts from the muscular dystrophy X-linked (MDX) skeletal muscle cell line, derived from the damaged muscles of MDX mice (kindly provided by Professor David Yaffe, RIP), which is commonly used as a mouse model of Duchenne muscular dystrophy (DMD). The staining of MDX cells was used to set the background staining for the cells' intrinsic calcium levels. Plates were precoated with gelatin, which is used as a standard attachment substrate for MDX cells. The cells were seeded on a 24-well plate at a density of $3\times10^4$ cells/well.

On day 2, two days following seeding, the medium in the wells was replaced as follows: 2 columns were treated with muscle proliferation medium+1 mM Ca, originated from ACC (2 mM total calcium concentration); 2 columns were treated with muscle proliferation medium+1 mM $Ca^{+2}$, originated from $CaCl_2$); and 2 columns were treated with a muscle proliferation medium.

Fixation was performed for both plates on the 10th day following medium exchange.

Results

MSCs are multipotent mesenchymal stem cells that can differentiate into a variety of cell types, including osteoblasts (bone cells), chondrocytes (cartilage cells), myocytes (muscle cells), and adipocytes (fat cells that give rise to the marrow adipose tissue).

Figure 13A:
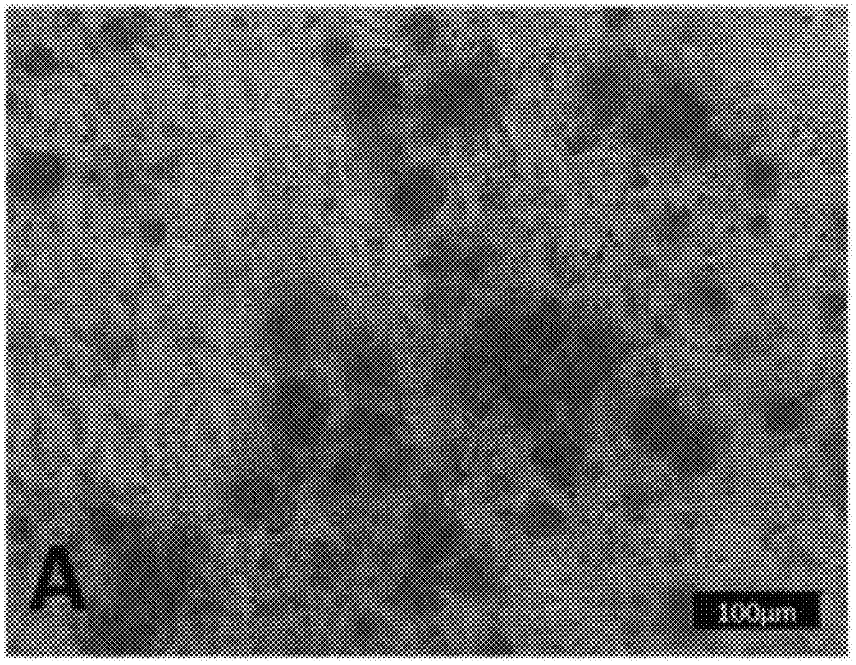
FIG. 13A-FIG. 13F show the images for Alizarin Red staining of MBA-13 osteoblasts following 10 days in culture with various medium treatments: MSCgo™ differentiation medium plus (FIG. 13A) ACC, (FIG. 13B) $CaCl_2$), (FIG. 13C) no added calcium source, (FIG. 13D). MSC-NutriStem® complete proliferation medium (negative control)
Figure 13B:
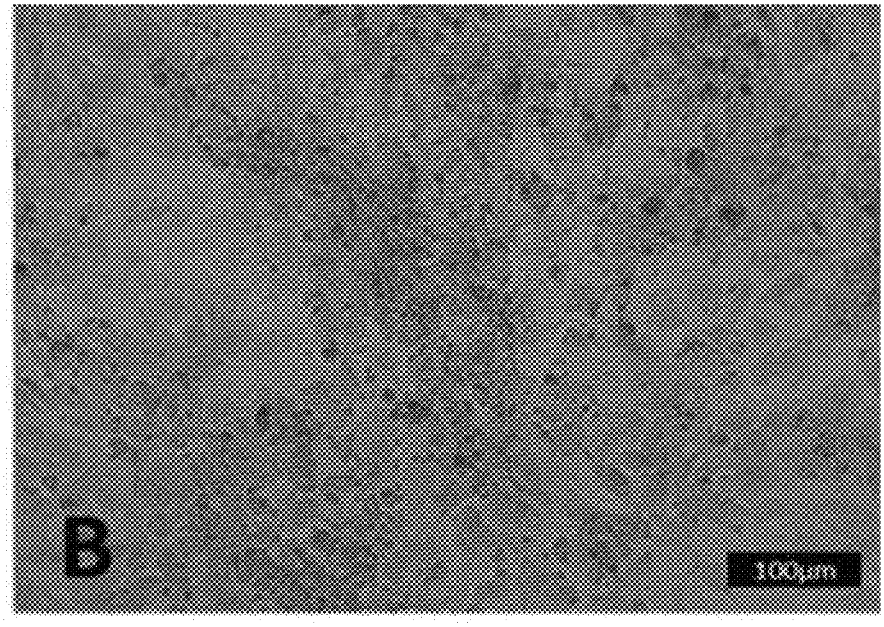
Figure 13C:
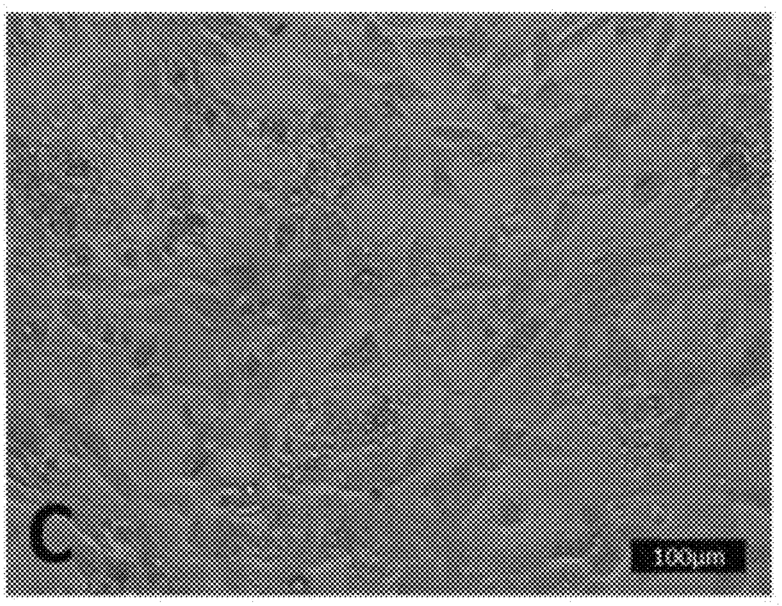
Figure 13D:
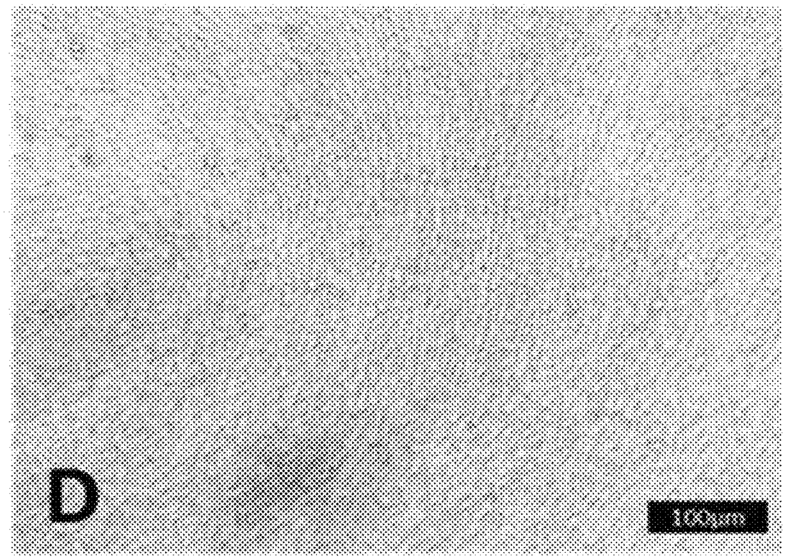
Figure 13E:
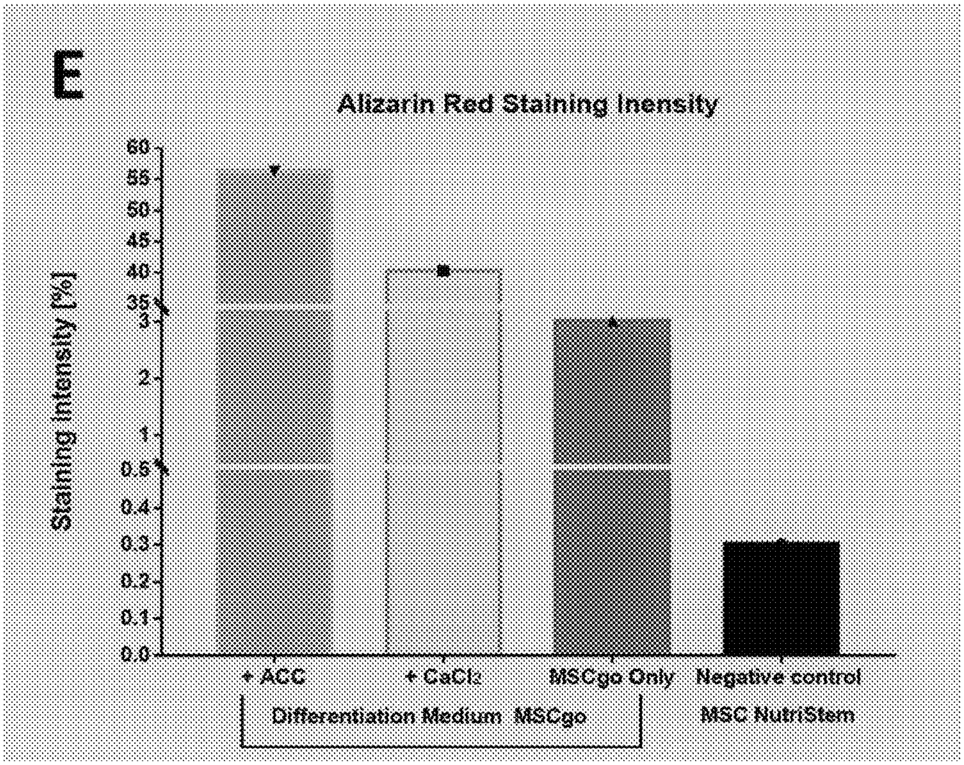
Figure 13F:
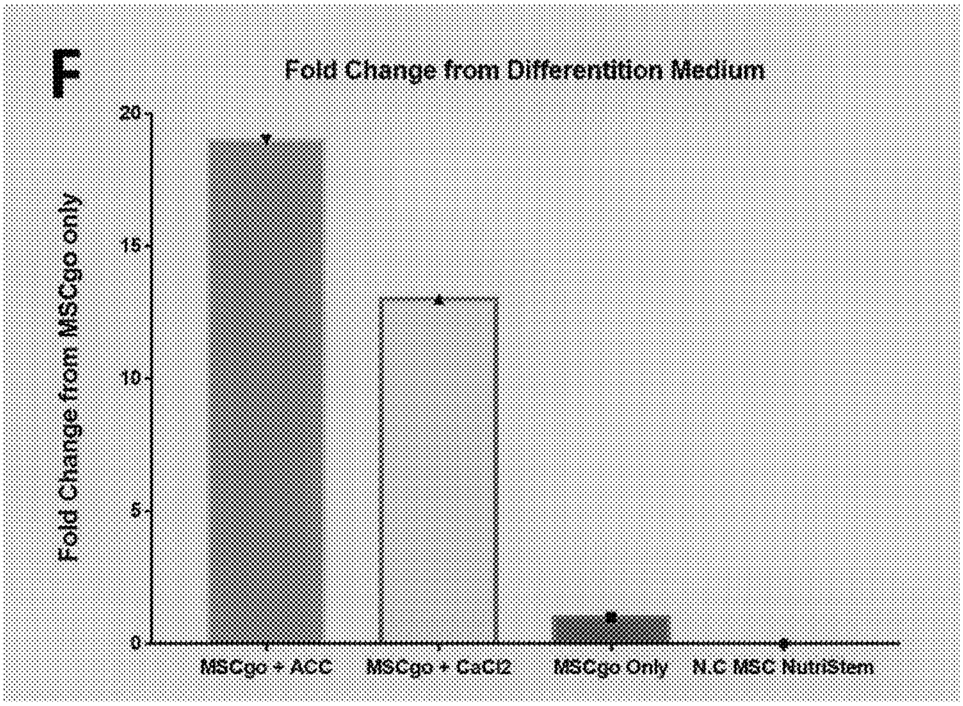

The effect of ACC on osteoblasts' functionality was studied on Earth prior to the space mission experiment by monitoring extracellular calcium deposition that is the outcome to the cell differentiation and activity. The experiments in space were performed on mouse osteoblasts (MBA-13 cells), using $CaCl_2$) as the standard calcium source in the medium serving as the control group for comparison. MDX cells were used as a negative control, as described in the Materials and Methods. Following fixation, two types of staining reagents were used to stain extracellular calcium or bone deposition to estimate the osteoblasts' functionality. Alizarin Red staining demonstrates calcium deposits (darker spots). The results revealed stronger Alizarin Red staining in osteoblast samples that were treated with ACC (FIG. 13A) compared with those treated with the $CaCl_2$) containing medium, where only weak staining was observed (FIG. 13B). In contrast, large plaques of stained calcium deposition were detected in the ACC containing culture.

Calcium deposition was not observed in cultures grown in MSC NutriStem® complete proliferation medium with ACC (negative control group). In this group, the cells were confluent, but no calcium deposition was observed. Hence, these results indicate that the ACC can affect the differentiation of MBA-13 cells into osteocytes and increase the cells' calcium deposition (i.e., their functionality).

Figure 14A:
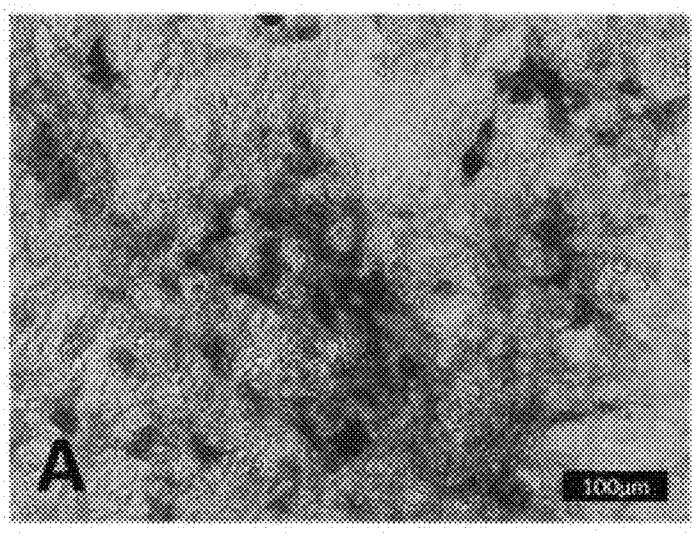
FIG. 14A-FIG. 14D show the images of alkaline phosphatase staining of MBA-13 osteoblasts following 10 days in culture with various medium treatments: MSCgo™ differentiation medium plus (FIG. 14A) ACC, (FIG. 14B) $CaCl_2$), (FIG. 14C) no added calcium, and (FIG. 14D) MSC-NutriStem® complete proliferation medium (negative control). The intense staining obtained for cells treated with medium enriched with ACC (FIG. 14A), indicating that addition of ACC accelerates bone maturation, as represented by calcium deposition.
Figure 14B:
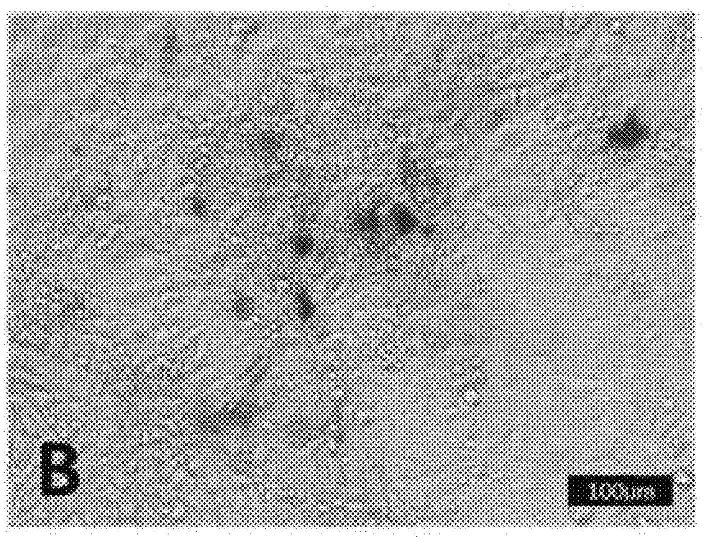
Figure 14C:
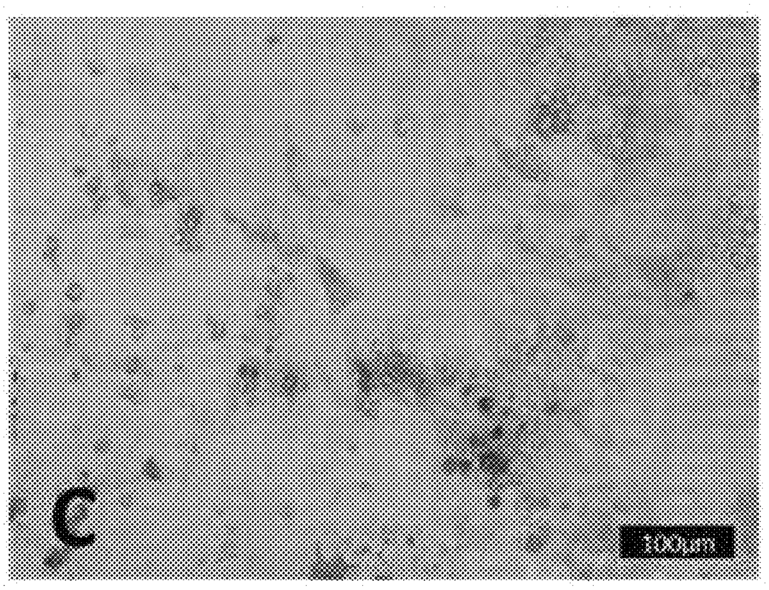
Figure 14D:
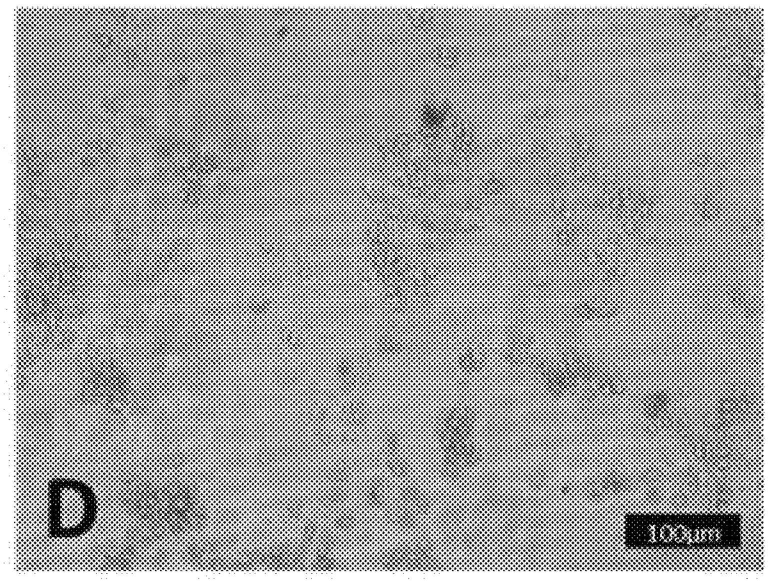

Alkaline phosphatase is another independent indicator for osteoblast differentiation. This enzyme is maximally expressed at the matrix maturation phase of cells. Therefore, we used alkaline phosphatase staining as a complementary analytical technique for detecting osteoblast differentiation and functionality in attempt to validate the calcium detection by the Alizarin Red staining (i.e., to exclude the presence of potentially unwashed ACC). Alkaline phosphatase is detected by a black color stain. As shown in FIG. 14, MBA-13 cells that were treated with ACC demonstrated more intense staining (FIG. 14A) in comparison to that of the other treatments (FIGS. 14B and 14C). Therefore, the alkaline phosphatase staining indicates that osteoblast differentiation is enhanced in cultures treated with ACC.

Figure 15A:
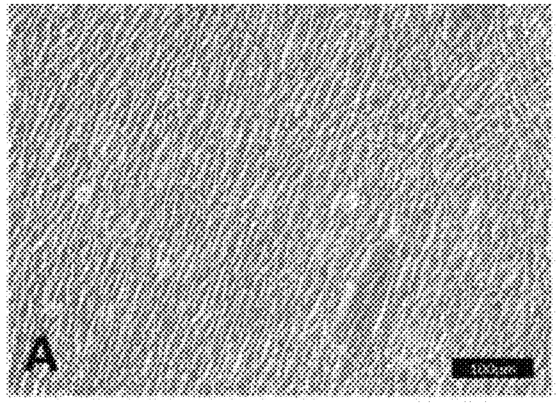
FIG. 15A-FIG. 15C shows the images of MDX cells treated with MSCgo™ differentiation medium plus (FIG. 15A) ACC, (FIG. 15B) $CaCl_2$), and (FIG. 15C) no added calcium source. Cells were stained with Alizarin Red 10 days following seeding.
Figure 15B:
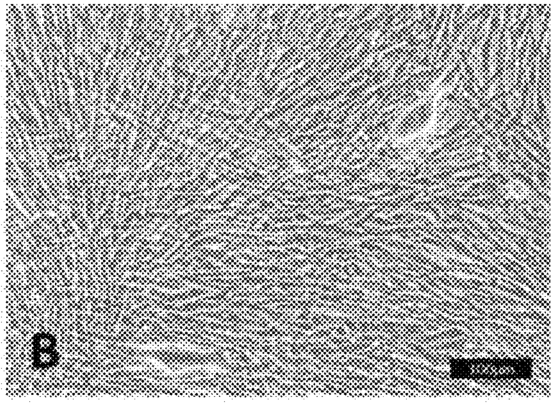
Figure 15C:
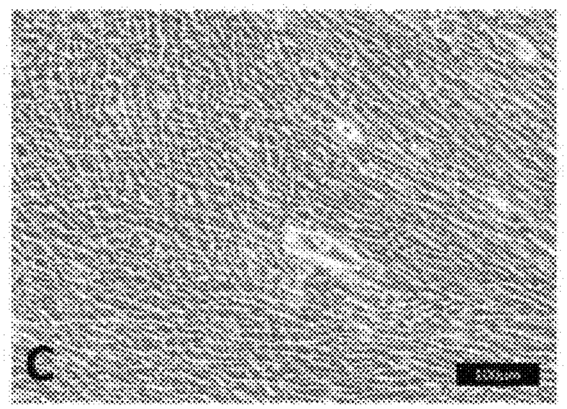

A side experiment was performed to confirm that the staining technique was not falsely indicating the presence of residual ACC. No marked differences in Alizarin Red staining of MDX cells treated with or without ACC-enriched medium 10 days following seeding were found, as shown in FIG. 15A-FIG. 15C. These results confirm that the observed Alizarin Red staining results are associated with calcium deposition by the osteoblasts and not a false staining outcome of ACC deposition itself. Similar culture experiments performed with many cell types (other than osteoblasts) demonstrated similar results.

Figure 16A:
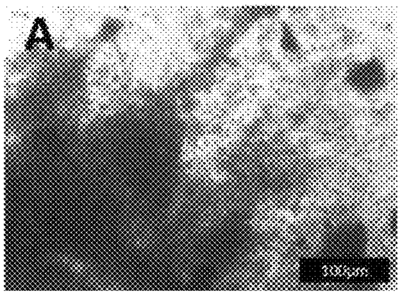
FIG. 16A-FIG. 16C shows microscope images of stained cells from cultures containing ACC in a previous experiment performed (FIG. 16A) in space and (FIG. 16B) on Earth. The differentiation period at the ISS was 2 weeks, whereas it was 3 weeks on Earth. The image intensity analysis of numerous figures obtained in the space and earth experiments is illustrated in (FIG. 16C).
Figure 16B:
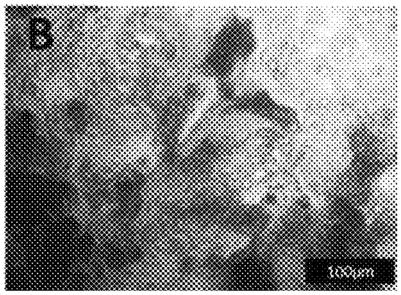
Figure 16C:
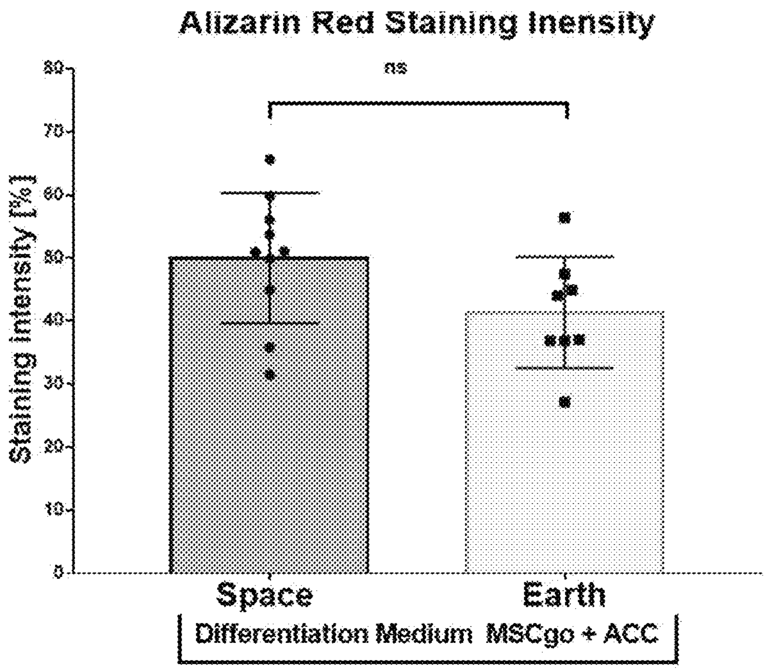

The above results correspond to those obtained in a smaller, study performed at the ISS in 2018 (NanoRacks-RSL-02). Due to severe load size and weight limitations, the first experiment was restricted to a single culture tube of BM-MSCs. Due to launching delays these cells were stored at room temperature conditions in a proliferation medium enriched with ACC for 3 weeks before being shipped to space in a special flexible tube with clamps, provided by Nanorex. The proliferation medium was separated by a clamp from a differentiation medium enriched with ACC and by another clamp from a fixation solution. The astronauts opened the first clamp after 2 weeks in space, and the cells were introduced into the differentiation medium. Two weeks after the first clamp opening, the second clamp was opened for the fixation of the cells with a PFA solution. A comparative experiment was performed simultaneously on Earth for simulation and control. The ACC treatment clearly affected the differentiation of BM-MSCs into osteocytes and significantly enhanced the cells' calcium deposition (i.e., their functionality) in direct comparison with a similar control experiment on Earth. Both the ISS and the Earth experiments demonstrated very strong staining demonstrating the formation of mature osteocytes (bone cells) with calcium deposition, as illustrated by the Alizarin staining in FIG. 16. The results obtained in the presence of ACC at extraterrestrial conditions were like those observed on Earth, or even slightly better, indicating the benefits of ACC in both microgravity and Earth conditions and a slightly better results in space. The analysis of the staining intensity determined insignificant differences in the staining intensity of the space versus the Earth experiments, both in the presence of ACC. Statistics were analyzed using Student's t-Test.

Example 25. Effects of ACC on Human BM-MSCs

Materials and Methods

Differentiation of BM-MSCs to Osteoblasts and Osteocytes

RoosterBio human mesenchymal stem/stromal cells (MSC-00, Lot #31268) were used in the differentiation experiment, which were isolated from the human bone marrow and expanded using controlled manufacturing processes. The cells were seeded in a fibronectin precoated culture flask; one ampule was thawed and seeded into four T-25 flasks and one T-75 flask containing the proliferation medium. When the cells reached confluency, they were split into 10 new flasks. A portion of the cells were frozen after one week of expansion and another portion remained to grow. The cells were seeded in duplicates at a dilution of 0.5 million cells/mL on the microfluidic chip device specifically designed for this study; two slots were established without ACC and two slots were established with ACC. The cells were grown for 4 days in the proliferation medium, prepared by aseptically mixing one bottle of RoosterBasal™-MSC (Part No. SU-005/SU-022) with one bottle of RoosterBooster™-MSC (Part No. SU-003). Five hours after arrival at the ISS, the medium was exchanged to MSCgo osteogenic differentiation medium (Sartorius cat #05-440-1B) containing factors that promote osteoblastic differentiation. MSCgo™ osteogenic differentiation medium (Sartorius cat #05-440-1B) is a serum-free, xeno-free, complete, and ready-to-use formulation developed for optimal differentiation of human MSCs to mature osteocytes.

Two slots in the microfluidic chip were supplemented with MSCgo™ with additional 1 mM calcium (total 2.5 mM calcium) originating from ACC. The two other slots were supplemented with MSCgo™ medium with additional 1 mM calcium (total 2.5 mM calcium) originating from $CaCl_2$). On day 7 after seeding (5 days in space), the medium in each treatment group was automatically refreshed at a flow rate of 17 μL/min.

Results

Figure 17A:
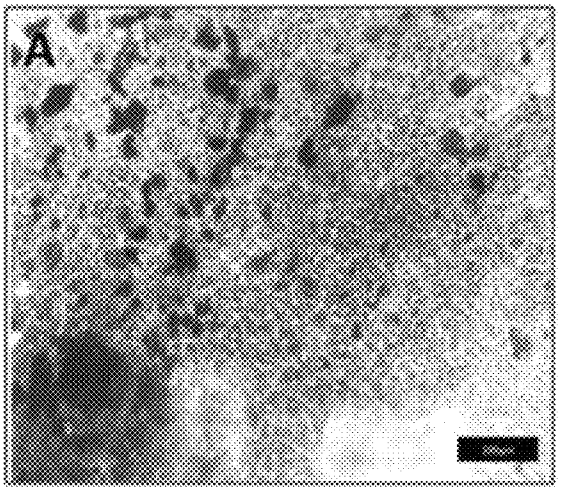
Figure 17B:
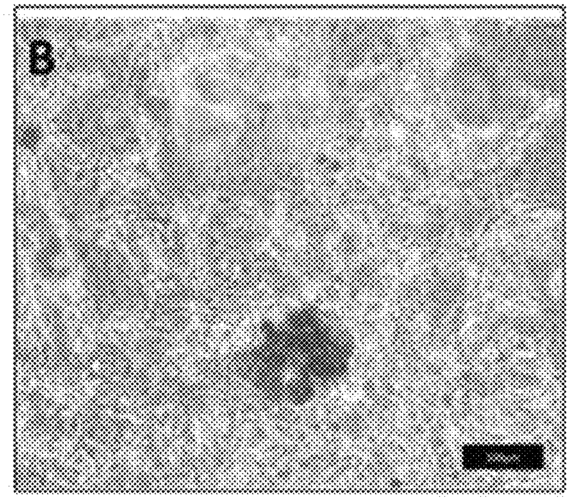
Figure 17C:
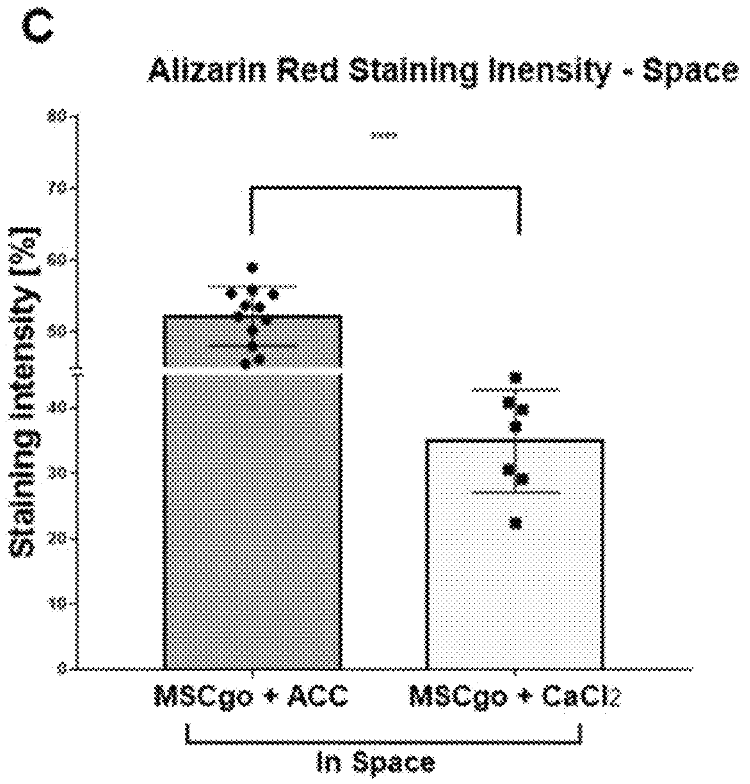

Despite the severe limitations in performing and following optimal culturing conditions and timing via a remotely controlled operation in space, the comparative microfluidic cultures at the ISS have demonstrated the efficient capability to distinguish between varied culture activities. As demonstrated in FIG. 17A-FIG. 17C, more mature bone cells (i.e., osteocytes) were obtained in the ACC-treated group in comparison to the control $CaCl_2$) group. Moreover, ACC maintained the survival of the cells in the extraterrestrial microgravity and radiation environment, matching their survival under similar conditions on Earth. Considering the muscle cells suffer from mass lost under microgravity conditions, obtaining results similar to those received on earth are in fact unexpected and represent a much better results than could have been expected. Statistically significant difference ($P<0.0001$) was achieved between the ACC-treated group (12 images) versus the control group (only 7 images since far fewer cells survived). The results confirmed the observations obtained in the previously uncontrolled spacelab study. The recent experiment further revealed that despite the short differentiation period at the ISS (only 6 days), ACC could accelerate the conversion of osteoblasts into osteocytes in space.

Figure 18A:
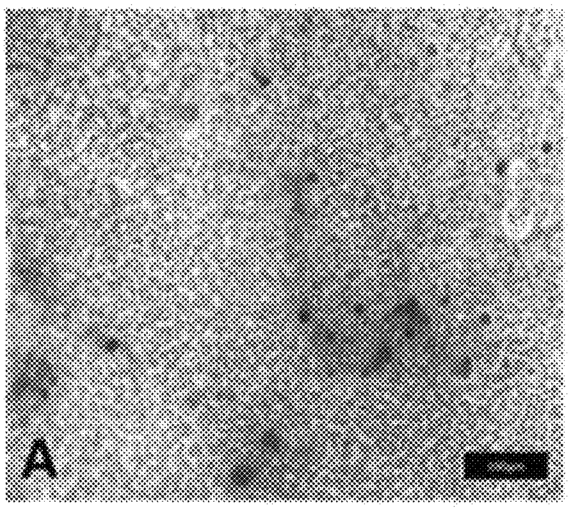
FIG. 18A-FIG. 18C show the phase-contrast microscope images illustrating the effect of ACC on human bone marrow-derived mesenchymal stem cells (BM-MSCs) cultured on Earth after Alizarin Red staining. The differentiation period was 6 days.
Figure 18B:
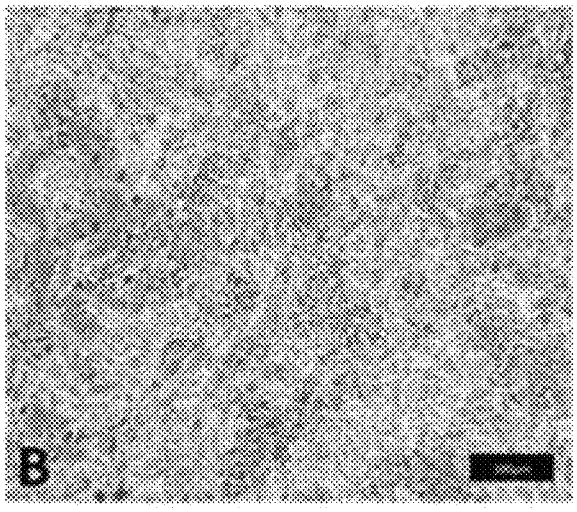
Figure 18C:
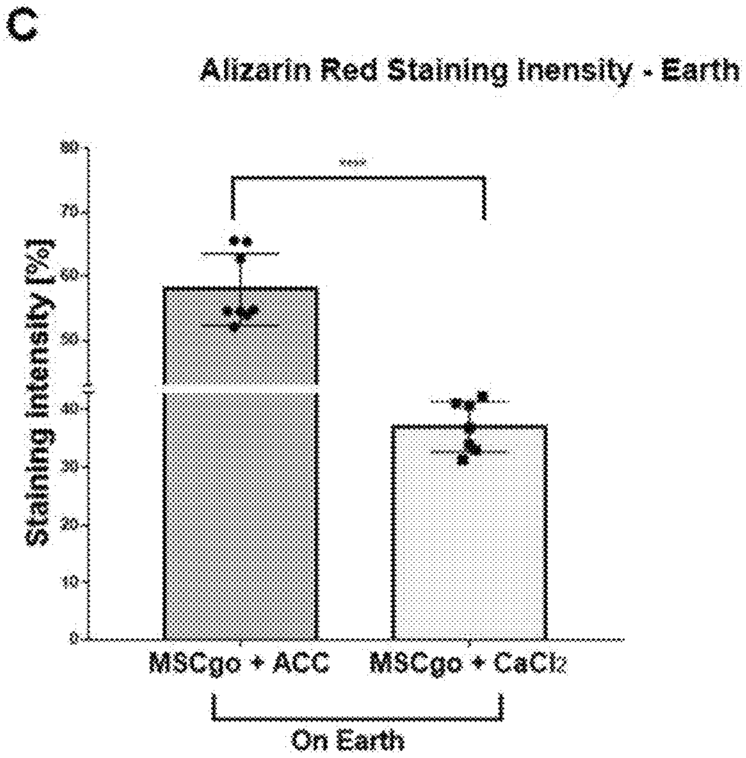
Figure 19A:
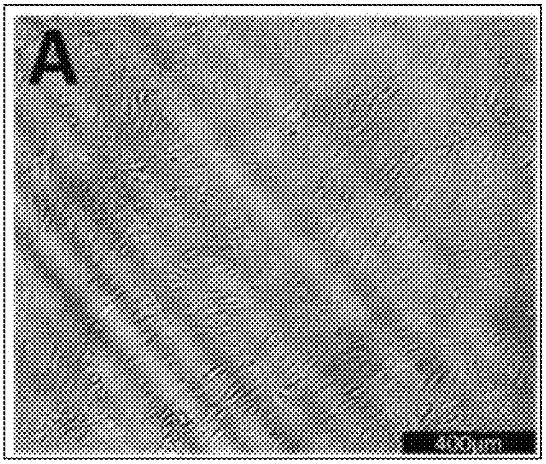
FIG. 19A-FIG. 19F show an example for images remotely taken by the embedded space microscope images tracking the effect of ACC on BM-MSC. Slot 6: BM-MSC without ACC.
Figure 19B:
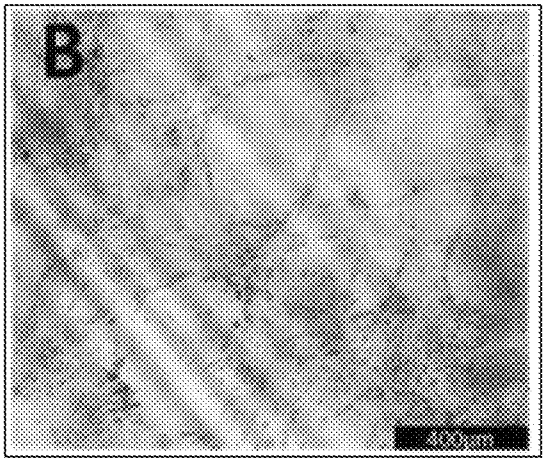
Figure 19C:
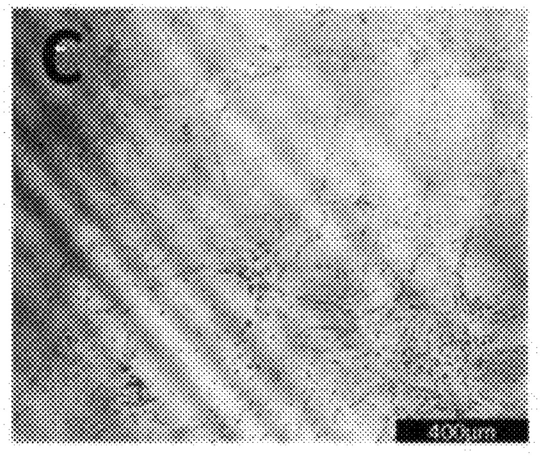
Figure 19D:
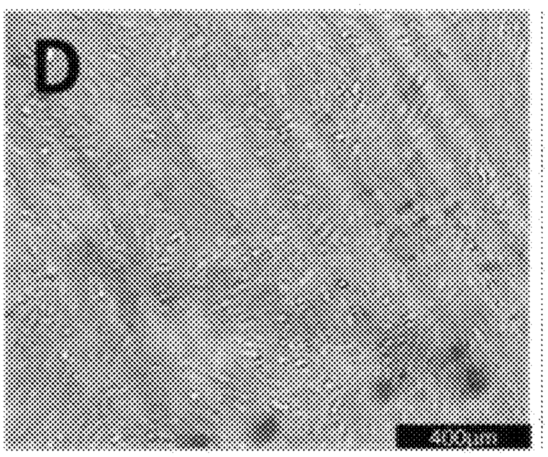
Figure 19E:
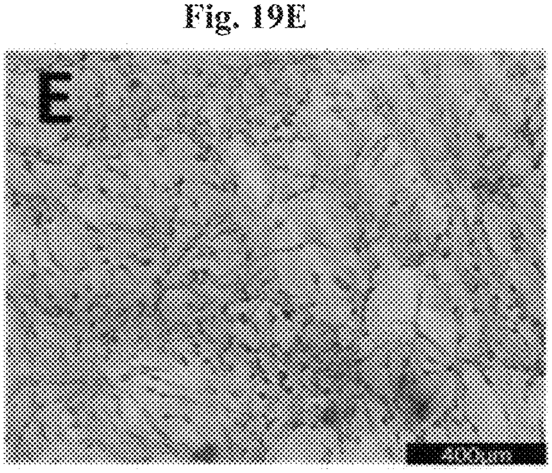
Figure 19F:
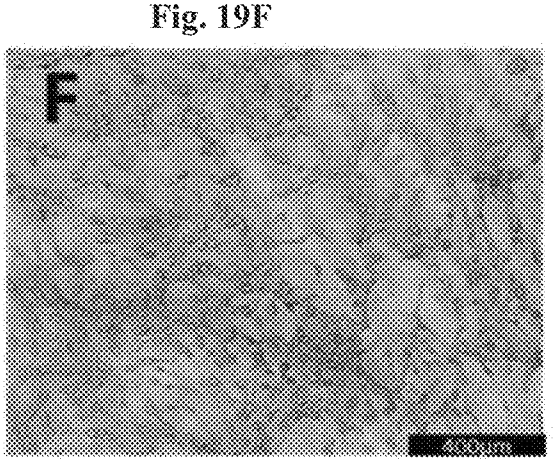

A very similar advantageous effect was also confirmed by morphological analysis (microscopy) of the same cells, cultured on Earth with ACC or $CaCl_2$) (FIG. 18C), although the cells in the control experiment on earth are differentiated better than in space and the cells survive the experiment much better than in space. Alizarin Red staining revealed very strong orange-red staining in the osteoblast culture that was supplemented with ACC (FIG. 18A) compared to that supplemented with $CaCl_2$) (FIG. 18B). Statistical mage analysis also reveals the significant enhanced activity in the presence of ACC ($P<0.0001$).

FIG. 19 demonstrates of the current capability to tract in real time culture progress in the SPAD device using the installed microscope. Although the resolution is relatively low at this stage, the cell growth and differentiation can be monitor and decisions regarding continuation or termination of in-space cultures can be effectively made.

Example 26. Effects of ACC on Primary Mouse Muscle Cells

Figure 20:
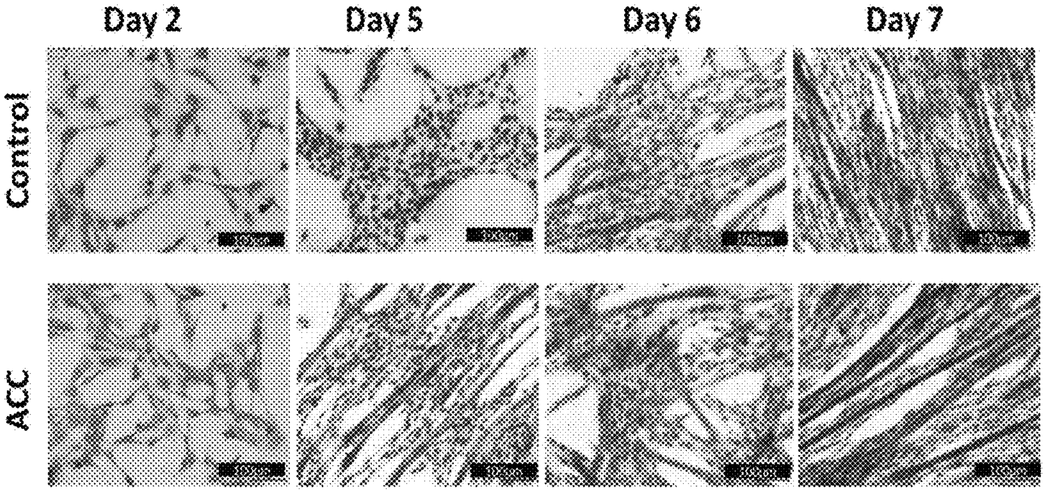
FIG. 20 shows microscope images of MDX muscle cells cultured with the addition of ACC or $CaCl_2$) (as a control). All samples contained a final calcium concentration of 2 mM. Cultures were fixed at the indicated days and stained with Giemsa. Note the enhancement in myotubes/muscle fiber formation in cultures exposed to ACC starting from day 5. The original magnification was 100×.
Figure 21A:
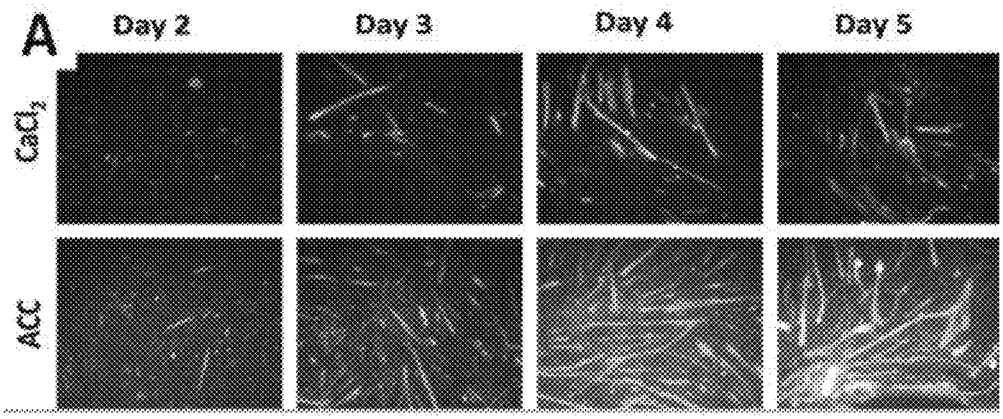
FIG. 21A and FIG. 21B show (FIG. 21A) representative fluorescence microscope images showing enhancement of myotubes formation by ACC. The enhancement in myotubes formation in cultures exposed to ACC starting from day 3. The original magnification was 100×.
Figure 21B:
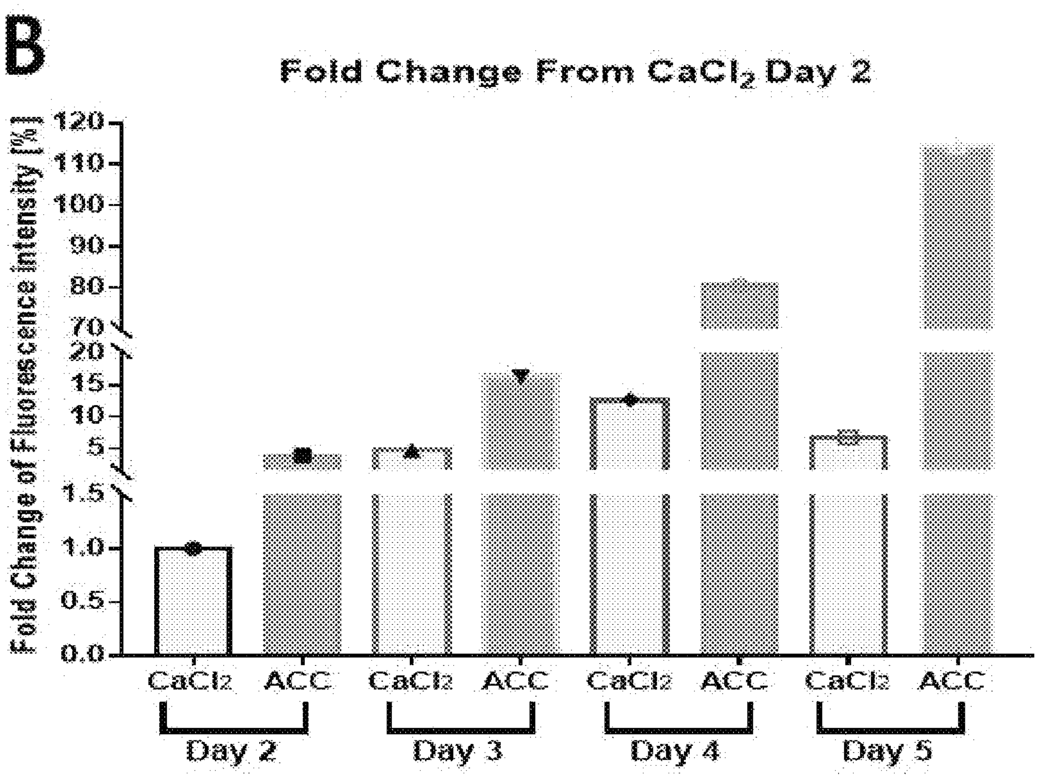

Positive effects of ACC on culturing muscle cells on Earth were explored and described in several publications, e.g. in U.S. Ser. No. 10/758,566. A higher proliferation rate of C2 cell line and primary muscle cells was demonstrated in the presence of ACC compared to a control group, in which the cells were grown in a $CaCl_2$)-enriched medium. In-vitro studies of cells extracted from newborn MDX mice have demonstrated better morphologies, higher cell counts, and earlier myotubes/muscle fiber formation when ACC was added in comparison to the incorporation of $CaCl_2$) into the control group cultures. as represented after Giemsa and myosin staining (FIG. 20). Moreover, contraction of muscle fibers appeared significantly earlier in the ACC group on Day 7 in comparison to Day 10 in the control group as shown in FIG. 21.

In this experiment the effect of ACC on the development and formation of muscle cells from primary stationary skeletal muscle in space was tested.

Skeletal Muscle Cultures

Primary stationary skeletal muscle cultures were prepared from healthy newborn (1 day old) Sprague-Dawley rats (Harlan, Israel). The posterior legs were cut out and the skin was removed. The muscle tissue was thoroughly minced and then digested with trypsin-EDTA. After 30 min, the supernatant, containing dissociated cells, was collected and fresh trypsin-EDTA was added. This procedure was repeated twice. Subsequently, all supernatants were pooled, centrifuged, and the cell pellet was resuspended in the proliferation medium. Cells were seeded in a gelatin-coated 12-well culture plate at $1\times10^5$ cells/well containing 1 mL of proliferation medium. Two days later, the medium was changed to the fusion medium, which was then exchanged twice a week. Calcium content (1 mM) was added to the medium, which originated from ACC, CCC, or $CaCl_2$) (the control group), for making a final calcium concentration of 2 mM. The cultures were daily monitored by phase-contrast microscope observations, starting 24 h after culture initiation and onward. At predetermined days, cultures were fixed in 99% methanol for 20 min and then stained with Giemsa to evaluate the number of myotubes formed over time.

Primary human skeletal muscle cells were obtained from American Type Culture Collection (PCS-950-010, Lot #70032406), which were isolated from a normal human skeletal muscle. The cells were seeded in a fibronectin precoated T-25 culture flask, at one ampule per flask, containing 5 mL of the proliferation medium. When the cells reached confluency, they were split into five new flasks. After one week of expansion, a portion of the cells was frozen, and another portion remained for further culturing. The cells were seeded at a dilution of 0.5 million cells/mL in a microfluidic chip device that was specifically designed for this study and pretested on Earth. Cells were seeded in duplicates, including two slots without ACC and two slots with ACC. The cells were grown for 3 days in the proliferation medium. Upon arrival to the ISS, the medium was automatically changed to the differentiation medium HI, just before docking. Giemsa staining was used to visually evaluate the muscle fibers formed by each cell during the experiment.

This experiment was performed bearing in mind that muscle tissue suffers for a severe loss in its mass in space.

Figure 22:
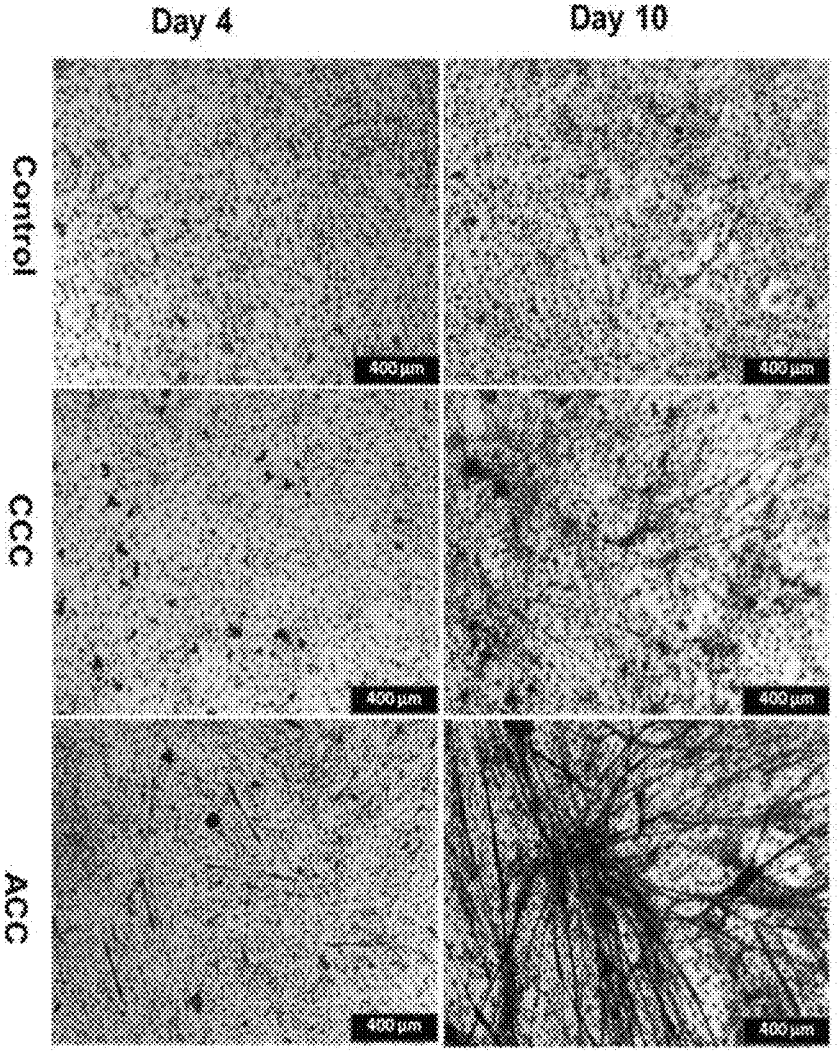
FIG. 22 shows the effect of ACC on the formation of muscle myotubes in microscope images of primary skeletal muscle cells, extracted from newborn rats. Cultures were enriched with 1 mM Ca originating from ACC, CCC, or $CaCl_2$) (control) solutions. Cultures were fixed after 4 or 10 days and stained with Giemsa. Original magnification 40×.
Figure 22:
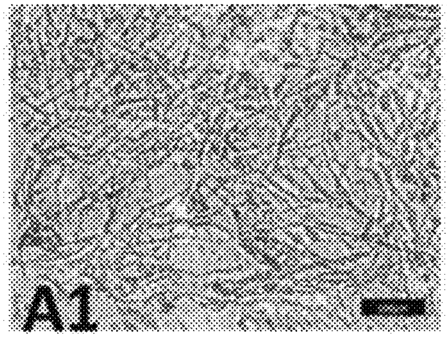
Figure 22:
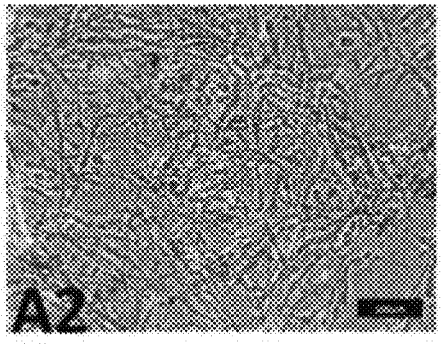

The results shown in FIG. 22 demonstrate that cultures of newborn mice's muscle cells, exhibited earlier formation of myotubes in the presence of ACC, within 4 days of cultivation, compared with the timing of myotube formation in the control groups (ACC or $CaCl_2$). After 7 days, the ACC-treated group exhibited numerous longer and thicker muscle fibers in comparison to the control groups, which developed fewer, thinner, and shorter muscle fibers. Furthermore, muscle contractions in cultures exposed to ACC were observed as early as day 7 after seeding, whereas muscle contractions appeared only after 10 days or more in cultures containing ACC or $CaCl_2$.

Example 27. Effects of ACC on Primary Skeletal Muscle Cells

Figure 2:
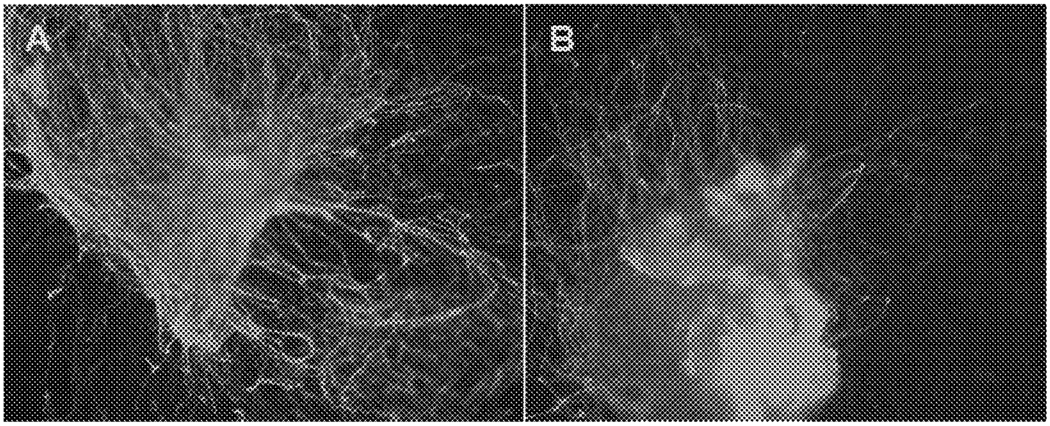
Figure 24A:
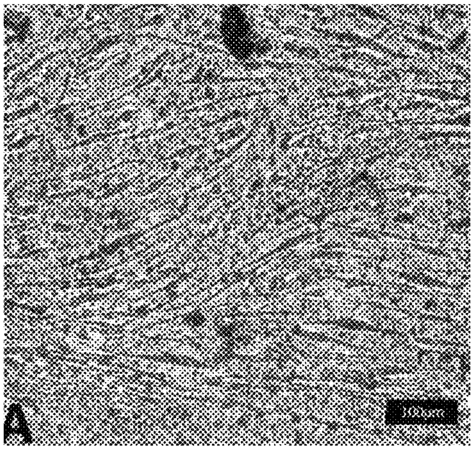
FIG. 24A-FIG. 24C show the phase-contrast microscope images illustrating the effect of ACC on human muscle cells on earth with Giemsa staining.
Figure 24B:
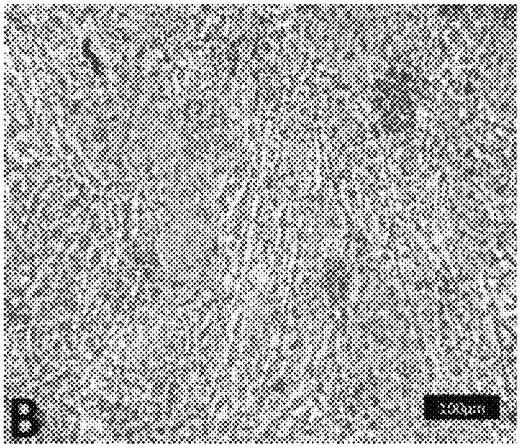
Figure 24C:
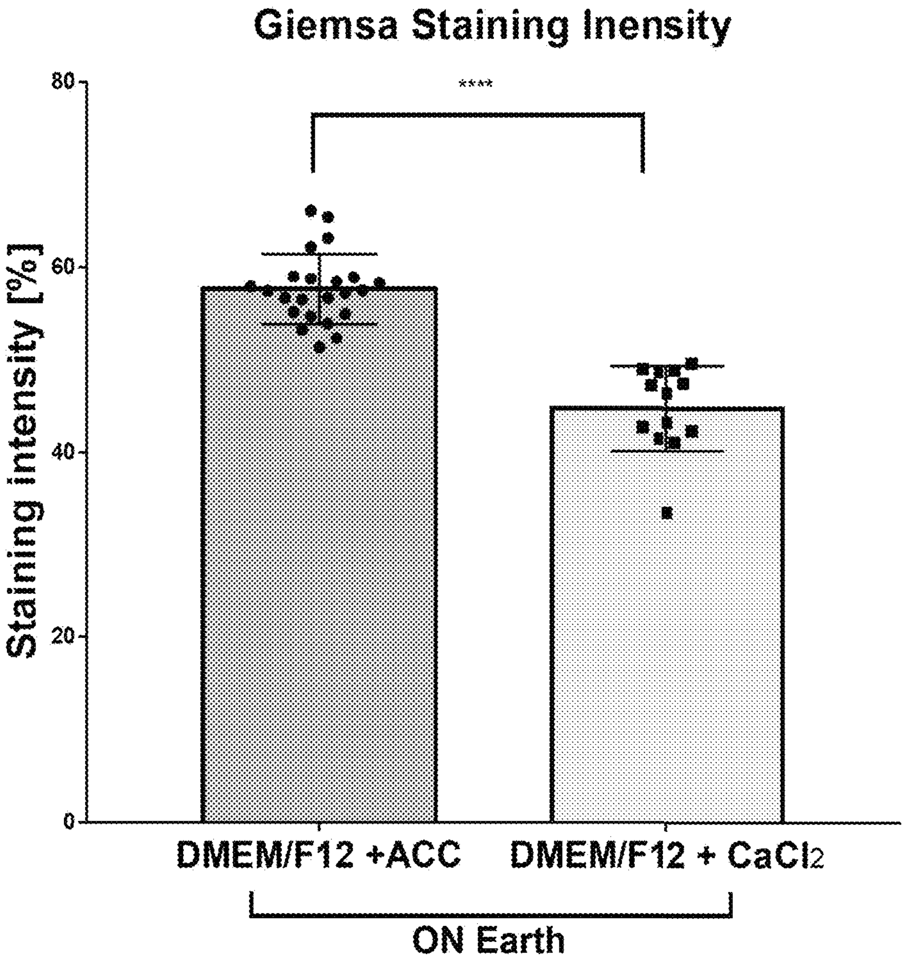
Figure 25A:
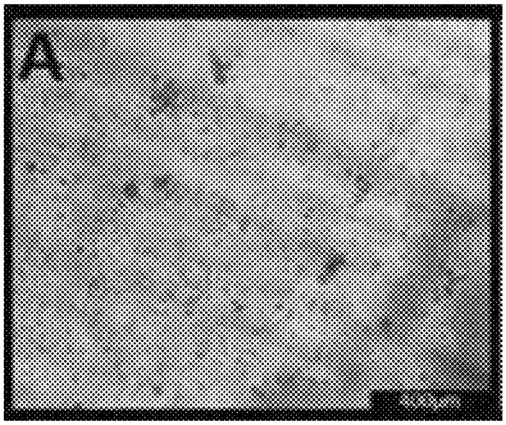
FIG. 25A-FIG. 25F shows an embedded space microscope images illustrating the effect of ACC on human muscle cells in space. The pictures were remotely captured by the microscope installed in the SPIC2 3.5U unit at the International Space Station. Slot 2 shows muscle cells without ACC in pictures taken in April 2022.
Figure 25B:
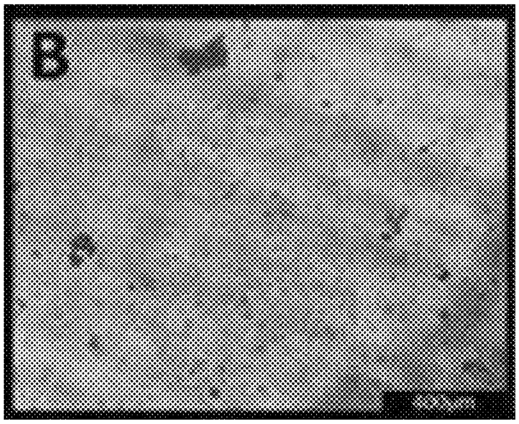
Figure 25C:
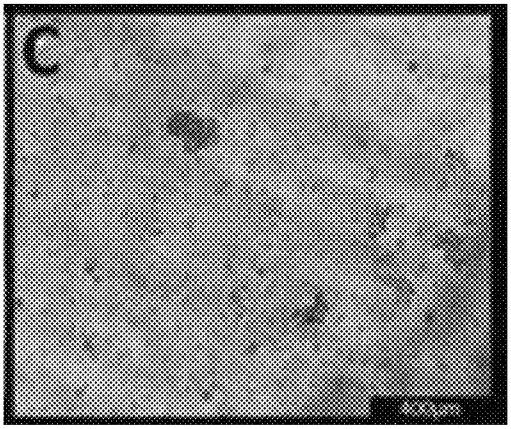
Figure 25D:
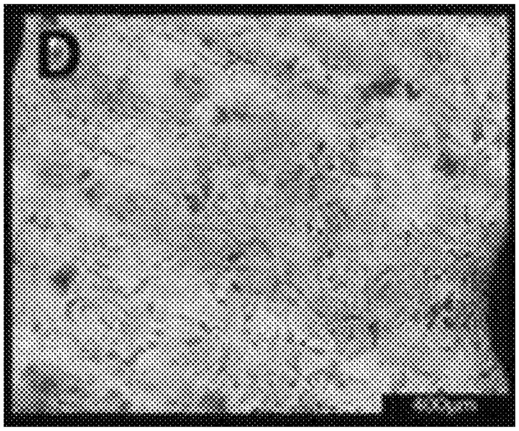
Figure 25E:
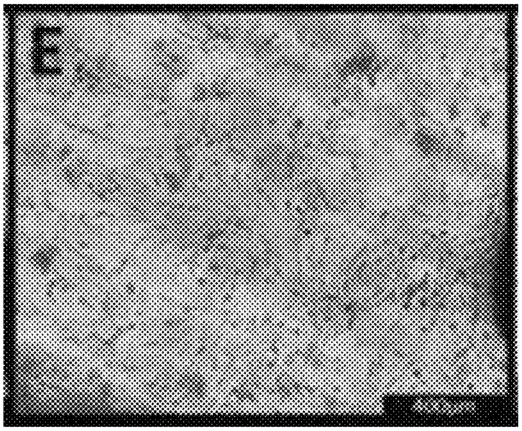
Figure 25F:
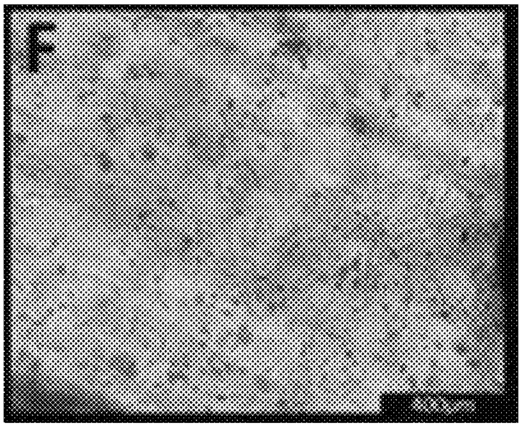

The results of the space experiment with primary muscle cells are presented in FIG. 23, representing the post-space mission analysis after Giemsa staining of the fixed culture. FIG. 23A1 and FIG. 23A2 represent the culture with ACC and FIG. 23B1 and FIG. 23B2 show the cultures with $CaCl_2$. The addition of ACC to the differentiation medium enhanced cell fusion and conversion into fiber cells significantly better than the equimolar addition of the conventional calcium ion source ($CaCl_2$). A similar effect was found in the control experiment performed on Earth (FIG. 24A-FIG. 24C). Furthermore, the presence of ACC maintained the survivability of the muscle cells in the space microgravity and radiation environment. These remarkable results were also captured by the remote microscopy performed in space (FIG. 25). In space, most of the cells cultured without ACC died, with cells surviving in only a few areas (FIG. 25A-FIG. 25C). This is contrary to cells that were grown in a medium supplemented with ACC (FIG. 25D-FIG. 25F). It should be noted that micrographs taken in space were captured at a random pre-defined location, without scanning for representative areas. It contrasts the analysis performed once the samples returned to Earth, as represented in FIG. 23.

Muscle cells growing with ACC continued to grow and form fiber cells in space, whereas the cells without ACC did not survive and most of them died, as demonstrated in FIG. 25B1 and FIG. 25B2). Overall, this experiment demonstrated improved and accelerated proliferation and differentiation of muscle cells into myotubes in the space environment in the presence of ACC, even over a short period of only 6 days. Significant differences were obtained between the two cultures ($P<0.0001$). In contrast, the muscle cells, grown in the control culture, were damaged by the microgravity environment to a greater extent than the bone cells discussed earlier. These observations coincide with previous studies showing that the loss of muscle tissue is higher than the loss of bone mass in space.

Although the present invention has been described herein above by way of preferred embodiments thereof, it can be modified, without departing from the spirit and nature of the subject invention as defined in the appended claims.

The invention claimed is:

1. A method for (i) enhancing growth of a biological culture, (ii) supporting growth of a biological culture, or (iii) both (i) and (ii) in microgravity conditions, the method comprising:

growing the biological culture in a cell culture medium comprising an amorphous calcium carbonate (ACC) stabilized by at least one stabilizer;

wherein the growth of the biological culture is performed in microgravity conditions; and wherein the ACC maintains a greater proportion of viable cells in the biological culture in microgravity compared to an equimolar concentration of calcium chloride.

2. The method of claim 1, further comprising enhancing growth of the biological culture, and wherein enhancing growth of the biological culture is selected from the group consisting of enhancing proliferation, enhancing maturation, enhancing propagation, enhancing regeneration, enhancing differentiation, enhancing development, enhancing the biological culture survival in space microgravity, enhancing the biological culture survival in radiation environment, and a combination thereof.

3. The method of claim 1, wherein the biological culture is selected from the group consisting of a culture of eukaryote or prokaryote cells.

4. The method of claim 3, wherein the culture of eukaryote cells is selected from a culture of animal cells, plant cells, or insect cells.

5. The method of claim 4, wherein at least one of:

the culture of animal cells is selected from a mammal cell culture, mammal tissue culture, organ culture, mammal stem cells, mammal gametes, mammal embryos, and a mammal organ, and wherein the mammal is human or non-human mammal;

the cell culture is the mammal cell culture selected from a nerve, muscle, epithelial, bone, adipose, stem cell, and blood cell culture; or the tissue culture is a mammal tissue culture is selected from epithelial, connective, muscular and nervous tissue culture; and the organ culture is an ovary.

6. The method of claim 5, wherein the cell culture is a primary cell culture or a cell line selected from the group consisting of a finite cell line and a continuous cell line.

7. The method of claim 6, wherein at least one of:

(i) the cell culture is a primary cell culture or a cell line selected from a finite cell line and a continuous cell line, optionally wherein said cell line is selected from bone-marrow derived MSC, MBA-13, MDX, FM3, HeLa, 293, A-549, ALC, CHO, HB54, HL60, COS-7, HEK293, VERO, BHK, CVI, MDCK, 3T3, C127 MRC-5, BAE-1, SH-SY5Y, L-929, HEP G2, NSO, U937, NAMALWA, WEHI 231, YAC 1, and U 266B1 cell line; or (ii) the epithelial tissue culture is selected from skin, stomach and intestinal lining, kidney and gland tissue culture, the muscular tissue culture is selected from smooth, skeletal and cardiac muscle tissue culture, the nervous tissue culture is selected from brain, spinal cord and nerve tissue.

8. The method of claim 5, wherein the stem cells are selected from the group consisting of embryonic, chorionic, amniotic, hematopoietic, mesenchymal, neural, nasal olfactory mucosa, glial, adult, and induced pluripotent stem cells.

9. The cell culture medium of claim 1, wherein the cell culture medium is selected from the group consisting of (i) a natural medium selected from biological fluids, tissue extracts and clots; (ii) an artificial medium selected from balanced salt solutions, basal medium and complex medium, wherein said artificial medium is optionally serum free medium, (iii) a medium suitable for growth of prokaryotes selected from YT and M9; and (iv) a medium suitable for growth of yeast, said medium selected from YPD, YPG and YPAD.

10. The cell culture medium of claim 9, wherein the cell medium is selected from the group consisting of DMEM/F-12, cleavage medium, serum free medium, DMEM, RPMI 1640, MEM, IMDM, Leibovitz's L-15 Medium, MCDB Medium, Medium 199, Schneider's *Drosophila* medium, Grace's Insect medium, Serum-free Insect Media, Shields and Sang M3 Insect Medium, TC-100 Insect Medium, TNM-FH Insect Medium, Ham's F-12, Ham's F-10, Ames' Medium, Basal Medium Eagle (BME), Claycomb medium, Click's Medium, Glasgow Minimum Essential Medium (GMEM), MegaCell Media, McCoy's 5A Modified Medium, NCTC Medium, Williams' Medium E, Waymouth Medium, TC-10 IPL-10 medium, medium for sperm separation, wash or maturation, medium for fertilization, for embryo development, and medium for embryo and gamete cryopreservation.

11. The method of claim 1, wherein said stabilizing agent is selected from the group consisting of a polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides, and derivatives thereof, proteins, phosphorylated proteins, natural and synthetic biopolymers and derivatives thereof, and any combinations thereof.

12. The method of claim 1, wherein the stabilizing agent is selected from the group consisting of phosphoserine, triphosphate, adenosine triphosphate, adenosine diphosphate, phytic acid, citric acid, etidronic acid, pyrophosphate, ethanol, hexametaphosphate, chitin, and any combination thereof.

13. The method of claim 1, wherein the average diameter of the stabilized ACC primary particles is about 10 nm to about 500 nm.

14. The method of claim 1, further comprising enhancing at least one of nerve cell regeneration;

muscle cell formation and growth;

stem cell differentiation;

oocyte or sperm cell maturation, embryo development;
embryo or gamete cryopreservation;
myotube formation;
onset for muscle cell contraction;
cell culture survival in space microgravity;
cell culture survival in radiation environment;
osteocyte formation; or
cell fusion and conversion into fiber cells.

15. A method of preventing a loss in the mass of a musculoskeletal system in space microgravity, in a subject in need thereof, the method comprising:

administering to said subject an amorphous calcium carbonate (ACC) stabilized by at least one stabilizing agent, wherein the ACC is administered in a dose that prevents bone or muscle mass loss more effectively than an equimolar dose of crystalline calcium carbonate.

16. The method of claim 15, further comprising preventing the loss of the mass of a bone and/or muscle.

17. A method of treating damages caused by exposure to microgravity conditions in a subject in need thereof, the method comprising:

administering to said subject an amorphous calcium carbonate (ACC) stabilized by at least one stabilizing agent, wherein the ACC treats said damages to a greater extent than a equimolar dose of crystalline calcium carbonate.

18. The method of claim 17, wherein the exposure comprises a staying in space about 1 month.

19. The method of claim 17, wherein the damage comprises loss of the mass of a bone and/or muscle.

* * * * *